(12) United States Patent
Li

(10) Patent No.: US 6,630,604 B1
(45) Date of Patent: Oct. 7, 2003

(54) POLYMER-SUPPORTED PHOSPHORUS LIGANDS FOR CATALYSIS

(75) Inventor: George Y. Li, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/807,279

(22) PCT Filed: Oct. 13, 1999

(86) PCT No.: PCT/US99/23509

§ 371 (c)(1),
(2), (4) Date: Apr. 9, 2001

(87) PCT Pub. No.: WO00/21663

PCT Pub. Date: Apr. 20, 2000

Related U.S. Application Data

(60) Provisional application No. 60/103,946, filed on Oct. 13, 1998.

(51) Int. Cl.$^7$ .......................... C07F 9/02; G01N 33/566; G01N 33/543
(52) U.S. Cl. ..................... 568/8; 568/17; 436/501; 436/518; 530/333; 530/335
(58) Field of Search ................... 568/8–17; 436/501; 436/518; 530/333, 335

(56) References Cited

U.S. PATENT DOCUMENTS

| 4,325,834 A | 4/1982 | Bartish | 252/429 R |
| 4,658,041 A | 4/1987 | Renga | 549/229 |
| 5,312,984 A | 5/1994 | Nicholas | 564/132 |

FOREIGN PATENT DOCUMENTS

| EP | 0040891 | 12/1981 | ............. B01J/31/06 |
| GB | 1517552 | 7/1978 | ............. C08F/8/40 |
| JP | 7853632 | 10/1976 | ............ C07C/49/76 |
| JP | 76128205 | 10/1976 | ............ C07C/49/76 |
| WO | WO 98/12202 | 3/1998 | ............. C07F/9/50 |

OTHER PUBLICATIONS

Burgess, K., et al., Accelerated Syntheses and Screening of Stereoselective Transition Metal Catalysts, *Advances in Catalytic Processes*, 2, 69–82, 1997.

Gilbertson, S. R., et al., The Combinatorial Synthesis of Chiral Phosphine Ligands, *Tetrahedron Letters*, 37, No. 36, 6475–6478, 1996.

Riegel, N., et al., Mono and Diphosphine Borane Complexes Grafted on Polypyrrole Matrix: Direct Use as Supported Ligands for Rh and Pd Catalysis, *Journal of Organometallic Chemistry*, 567, 219–233, 1998.

Holzhey, N., et al., Die Heterogen Katalysierte Co–Oligomerisation Von 1,3–Butadien Und CO2 Mit Immobilisierten Palladiumkomplexen, *Journal of Organometallic Chemistry*, 541, 243–248, 1997 (foreign article with English abstract).

Burgess, K. et al., Application of Novel Phosphine Oxazoline Ligands in Asymmetric Allylations of 4–Acyloxy–2–Pentene Derivatives, *Tetrahedron: Asymmetry*, 9, 2465–2469, 1998.

Vanleeuwen, P. W. N. M., et al., Polymer–Bound Bulky–Phosphite Modified Rhodium Hydroformylation Catalysts, *Macromol. Symp.,* 80, 241–256, 1994.

Kaye, P. T., et al., Dabco–Catalysed Reactions of Salicylaldehydes with Acrylate Derivatives, *Synthetic Communications*, 26, 11, 2085–2097, 1996.

Neckers, *J. Macromol. Sci., Chem.,* A24, 431–448, 1987.

Balkenhohl et al., Angew. Chem., Int. Ed. Engl. 1996, 35,2288–2337.

Gilbertson et al., J. Organometallics 1996, 15, 4678–4680.

Cao, X., et al., Combinatorial Method for the Synthesis of A–Hydroxy Phosphonates on Wang Resin, *Tetrahedron Letters*, 37, No. 34, 6073–6076, 1996.

*Supported Metal Complexes,* D. Reidel Publishing, 1985.

*Primary Examiner*—Jezia Riley
(74) *Attorney, Agent, or Firm*—Inna Y. Belopolsky

(57) ABSTRACT

Novel phosphine and phosphine oxide ligands are prepared using polymeric supports. These compounds can be easily cleaved from the support, and along with the corresponding supported compounds, used as ligands in the preparation of novel, metal-complexed catalysts. The ligands are obtained by combinatorial synthesis. A process for preparing coumarin by contacting salicylaldehyde with an acrylate is also provided.

22 Claims, No Drawings

POLYMER-SUPPORTED PHOSPHORUS LIGANDS FOR CATALYSIS

This application claims benefit of Ser. No. 60/103,946 filed Oct. 13, 1998.

FIELD OF INVENTION

This invention relates to the preparation of novel polymer-supported phosphine and phosphine oxide compounds and the corresponding free compounds after cleavage from support. These compounds are useful as ligands in the preparation of metal-containing catalysts.

BACKGROUND

As is generally known in prior art, chelating phosphine compounds when bound to metal atoms are useful as catalysts. To facilitate separation of the catalysts from a chemical process, phosphorus ligands have been attached to solid supports such as polymers ("Supported Metal Complexes", D. Reidel Publishing, 1985; Acta. Polymer. 1996, 47, 1; "Chem. Met.-Carbon Bond", Hartley, F. R (Ed), 1987, vol. 4, pp. 1163–1225; Neckers, *J. Macromol. Sci., Chem.* 1987, A24, 431–48). Interest in using the combinatorial "split and mix synthesis" approach to generate polymer-bound ligands which could be tested as catalysts has brought to fore the importance of new chemistry with which to attach phosphine ligands to polymer supports (Balkenhohl et al., *Angew. Chem., Int. Ed. Engl.* 1996, 35, 2288–2337; Gilbertson et al., *J. Organometallics* 1996, 15, 4678–4680; Gilbertson et al., *J. Am. Chem. Soc.* 1994, 116, 4481–4482).

Novel processes have been discovered to prepare new compositions of matter that contain chelating phosphine compounds, including compounds of asymmetric diphosphines. Phosphine compounds have been shown to be useful when combined with transition metals as catalysts for chemical processes. The processes can also be utilized in a combinatorial scheme to produce libraries of phosphine compounds.

Addition of aldehyde in salicylaldehydes to acetylenes is known, but is unknown for addition to alkenes. (Kokai Tokkyo Koho JP 7853632; JP 76128205 Kokubo et al., *J. Org. Chem.* 1997, 62, 4564–4565.) The new phosphorus compounds have been shown to be useful as ligands in catalysts for the decarbonylation of the salicylaldehyde and insertion of the alkene, followed by ring closure forming a coumarin.

SUMMARY OF THE INVENTION

This invention is directed to compositions and processes to prepare polymer supported phosphine and phosphine oxide compounds and the corresponding free compounds after their cleavage from the polymer support.

More specifically, the invention is directed to a process to prepare a supported phosphine compound selected from the group consisting of Formulae 1, 2, 3, 4, 5, 6, and 7

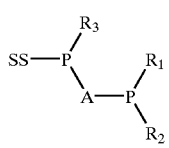

1

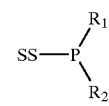

2

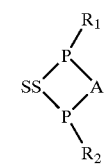

3

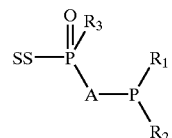

4

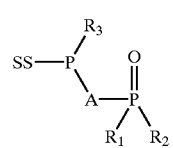

5

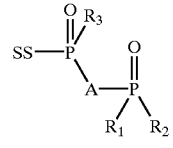

6

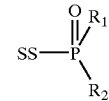

7 wherein:
SS is a solid support; A is a divalent group of 1–12 aliphatic or aromatic carbon atoms, linear or branched, optionally containing one or more heteroatoms or organometallic groups; $R_1$, $R_2$, and $R_3$ are independently selected from the group consisting of hydrogen, hydrocarbyl, substituted hydrocarbyl, heterocycle, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle, and $R_2$ and $R_3$ together, $R_1$ and $R_3$ together, or $R_1$ and $R_2$ together can optionally form a ring, the process comprising the steps of:

a) contacting (i) a phosphine selected from the group consisting of $XPR_1R_2$, $XR_3P$—A—$PR_1R_2$, $HP(=O)R_1R_2$, $HP(=O)R_3$—A—$PR_1R_2$, and $HP(=O)R_3$—A—$P(=O)R_1R_2$ wherein X is a halogen, with (ii) the solid support, resulting in at least one P in the phosphine attached indirectly or directly to the solid support via one or more covalent bonds, and b) optionally replacing one or more substituent of the group $R_1$, $R_2$, or $R_3$ with any other substituent of the group $R_1$, $R_2$, or $R_3$.

In all process and compositions embodiments of the invention, the preferred SS is selected from the group consisting of polyolefins, polyacrylates, polymethacrylates, and copolymers thereof.

The process is useful in producing the preferred supported phosphine compounds selected from the group consisting of Formulae 1A, 2A, 3A, 4A, 5A, 6A, and 7A.

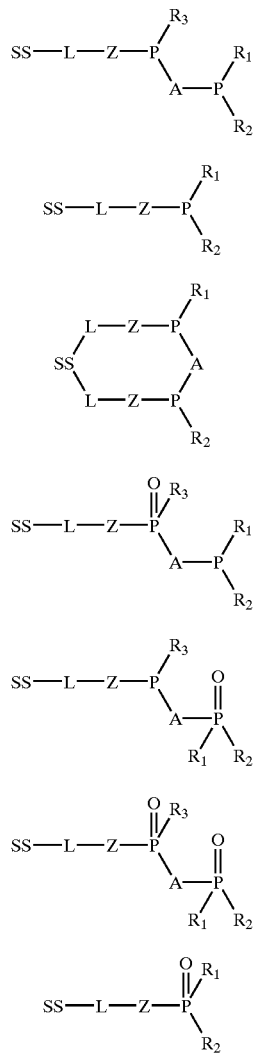

wherein:

Z is a divalent attaching group covalently attached to at least one P in the phosphine, selected from the group consisting of hydrocarbylene, substituted hydrocarbylene, —O—, —S—, and —NR$_4$—, where R$_4$ is selected from the group consisting of an optionally-substituted hydrocarbyl and halogen; and L is a divalent linking group covalently attached to Z and to SS, selected from the group consisting of optionally-substituted chains of from 1 to 12 linear, branched, and cyclic carbon atoms.

More particularly, this process to prepare supported phosphine compounds uses the supported phosphine compound of Formula 1A, where the process comprises the steps of:

a) contacting (i) at least 2 molar equivalents of a phosphine of the Formula XR$_3$P—A—PR$_1$R$_2$ wherein X is a halogen, with (ii) no more than one molar equivalent of Z, resulting in one P in the phosphine being covalently bonded to the Z, and b) optionally replacing one or more substitutent of the group R$_1$, R$_2$, and R$_3$ with any one or more of R$_1$, R$_2$, and R$_3$. In this process the SS is more preferably polystyrene; L is —CH$_2$—; A is selected from the group consisting of an optionally-substituted carbon chain of 1–3 carbon atoms and an optionally-substituted carbon ring of 6–12 carbon atoms; Z is selected from the group consisting of an optionally-substituted carbon chain of 1–10 carbon atoms, —(NR$_4$)—, and —O—; R$_4$ is selected from the group consisting of chloro, cyclohexyl, n-propyl, i-propyl, n-butyl, phenyl, and t-butyl; R$_1$, R$_2$, and R$_3$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$, and Q$_4$ are selected from the group consisting of hydrogen, hydrocarbyl, substituted hydrocarbyl, hydrocarbylamino, and heterocycle, and where R$_1$ and R$_2$ together with the P form a phosphole, aryl, or alkyl ring.

Alternatively, the process may use a supported phosphine compound of Formula 2A, with the process comprising the steps of:

a) contacting (i) a phosphine of the Formula PR$_1$R$_2$X wherein X is a halogen, with (ii) the solid support, resulting in one P in the phosphine being covalently bonded to Z, and b) optionally replacing one or both of R$_1$ and R$_2$ with any other R$_1$ or R$_2$. In this process the SS is more preferably polystyrene; is —CH$_2$—; Z is selected from the group consisting of optionally-substituted carbon chain of 1–10 carbon atoms, —(NR$_4$)—, and —O—; R$_4$ is selected from the group consisting of chloro, cyclohexyl, n-propyl, i-propyl, n-butyl, phenyl, and t-butyl; and R$_1$ and R$_2$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$, and Q$_4$ are selected from the group consisting of hydrogen, hydrocarbyl, substituted hydrocarbyl, hydrocarbylamino, and heterocycle, and where R$_1$ and R$_2$ together with the P form a phosphole, aromatic or alkyl ring.

Alternatively, this process may use the supported phosphine compound of Formula 3A, with the process comprising the steps of:

a) contacting (i) no more than one molar equivalent of a phosphine of the Formula XR$_3$P—A—PR$_1$R$_2$ wherein X is a halogen, with (ii) at least two molar equivalents of Z, resulting in both of the P in the phosphine being covalently bonded to the Z; and b) optionally replacing one or more of R$_1$ and R$_2$ with any one or more of R$_1$ and R$_2$. In this process the SS is more preferably polystyrene; L is —CH$_2$—; A is selected from the group consisting of an optionally-substituted carbon chain of 1–3 carbon atoms and an optionally-substituted carbon ring of 6–12 carbon atoms; Z is selected from the group consisting of an optionally-substituted carbon chain of 1–10 carbon atoms, —(NR$_4$)—, and —O—; R$_4$ is selected from the group consisting of chloro, cyclohexyl, n-propyl, i-propyl, n-butyl, phenyl, and t-butyl; R$_1$ and R$_2$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$, and Q$_4$ are selected from the group consisting of hydrogen, hydrocarbyl, substituted hydrocarbyl, hydrocarbylamino, and heterocycle, and where R$_1$ and R$_2$ together with the P form a phosphole, aryl, or alkyl ring.

Alternatively, this process may use the supported phosphine compound of Formula 4A, with the process comprising the steps of:

a) contacting (i) a phosphine of the Formula HP(=O)R$_3$—A—PR$_1$R$_2$ with (ii) the solid support, resulting in one P in the phosphine being covalently bonded to Z; and b) optionally replacing one or more of $R_1$, $R_2$, and $R_3$ with any one or more of $R_1$, $R_2$, and $R_3$. In this process the SS is more preferably polystyrene; L is —$CH_2$—; Z is selected from the group consisting of optionally-substituted carbon chain of 1–10 carbon atoms, —($NR_4$)—, and —O—; $R_4$ is selected from the group consisting of chloro, cyclohexyl, n-propyl, i-propyl, n-butyl, phenyl, and t-butyl; and $R_1$, $R_2$, and $R_3$ are independently selected from the group consisting of hydrogen, Cl, alkyl, alkenyl, aryl, $SQ_1$, $Q_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle, and where $R_1$ and $R_2$ together with the P form a phosphole, aryl, or alkyl ring.

Alternatively, this process may use the supported phosphine compound of Formula 5A with the process comprising the steps of:

a) contacting (i) a phosphine of the Formula HP(=O)$R_1R_2$ with (ii) a solid support of the formula

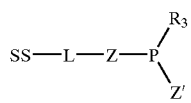

wherein the P in the solid support is covalently bonded to Z and Z' is selected from the group consisting of alkenyls, resulting in the P in the phosphine being covalently bonded to the P in the solid support via Z'; and b) optionally replacing one or more of $R_1$, $R_2$, and $R_3$ with any one or more of $R_1$, $R_2$, and $R_3$. In this process the SS more preferably is polystyrene; L is —$CH_2$—; Z is selected from the group consisting of optionally-substituted carbon chain of 1–10 carbon atoms, —($NR_4$)—, and —O—; A is selected from the group consisting of an optionally-substituted carbon chain of 1–3 carbon atoms and an optionally-substituted carbon ring of 6–12 carbon atoms; $R_4$ is selected from the group consisting of chloro, cyclohexyl, n-propyl, i-propyl, n-butyl, phenyl, and t-butyl; and $R_1$, $R_2$, and $R_3$ are independently selected from the group consisting of hydrogen, Cl, alkyl, alkenyl, aryl, $SQ_1$, $OQ_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle; and where $R_1$ and $R_2$ together with the P form a phosphole, aryl, or alkyl ring.

This invention is also directed to a process to prepare a combinatorial library of supported phosphine compounds selected from the group consisting of Formulae 1, 2, 3, 4, 5, 6, and 7

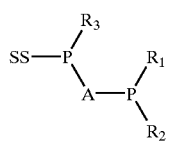

1

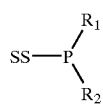

2

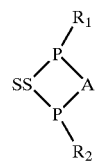

3

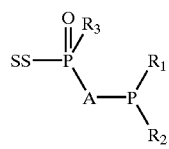

4

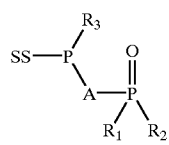

5

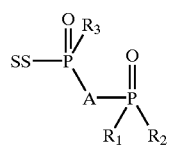

6

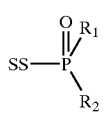

7 wherein:

SS is a solid support;

A is a divalent group of 1–12 aliphatic or aromatic carbon atoms, linear or branched, optionally containing one or more heteroatoms or organometallic groups;

$R_1$, $R_2$, and $R_3$ are independently selected from the group consisting of hydrogen, hydrocarbyl, substituted hydrocarbyl, heterocycle, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle, and $R_2$ and $R_3$ together, $R_1$ and $R_3$ together, or $R_1$ and $R_2$ together can optionally form a ring, the process comprising the steps of:

a) contacting (i) one or more phosphines selected from the group consisting of $XPR_1R_2$, $XR_3P$—A—$PR_1R_2$, HP(=O)$R_1R_2$, HP(=O)$R_3$—A—$PR_1R_2$, and HP(=O)$R_3$—A—P(=O)$R_1R_2$ wherein X is a halogen, with (ii) one or more solid supports, resulting in at least one P in each phosphine attached indirectly or directly to the solid support via one or more covalent bonds, and b) optionally replacing one or more $R_1$, $R_2$, or $R_3$ with any other $R_1$, $R_2$, or $R_3$.

The process is useful in producing a combinatorial library in which the preferred supported phosphine compounds are selected from the group consisting of Formulae 1A, 2A, 3A, 4A, 5A, 6A, and 7A

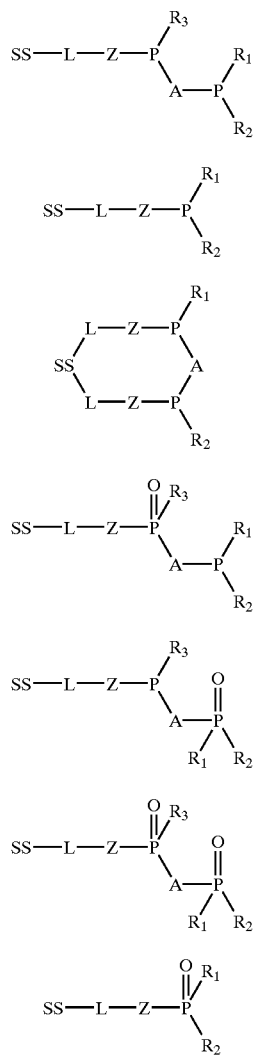

1A
2A
3A
4A
5A
6A
7A wherein:

Z is a divalent attaching group covalently attached to at least one P in the phosphine, selected from the group consisting of hydrocarbylene, substituted hydrocarbylene, —O—, —S—, and —NR$_4$—, where R$_4$ is selected from the group consisting of an optionally-substituted hydrocarbyl and halogen; and L is a divalent linking group covalently attached to Z and to SS, selected from the group consisting of optionally-substituted chains of from 1 to 12 linear, branched, and cyclic carbon atoms.

More preferably, this process to prepare a combinatorial library of supported phosphine compounds uses Formula 1A with the process comprising the steps of:

a) contacting at least 2 molar equivalents of one or more phosphines of the Formula XR$_3$P—A—PR$_1$R$_2$ wherein X is a halogen, with no more than one molar equivalent of one or more of Z, resulting in one P in each phosphine being covalently bonded to the Z; and b) optionally replacing one or more of R$_1$, R$_2$, and R$_3$ with any one or more of R$_1$, R$_2$, and R$_3$. In this process the SS more preferably is polystyrene; L is —CH$_2$—; A is selected from the group consisting of an optionally-substituted carbon chain of 1–3 carbon atoms and an optionally-substituted carbon ring of 6–12 carbon atoms; Z is selected from the group consisting of an optionally-substituted carbon chain of 1–10 carbon atoms, —(NR$_4$)—, and —O—; R$_4$ is selected from the group consisting of chloro, cyclohexyl, n-propyl, i-propyl, n-butyl, phenyl, and t-butyl; R$_1$, R$_2$, and R$_3$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$, and Q$_4$ are selected from the group consisting of hydrogen, hydrocarbyl, substituted hydrocarbyl, hydrocarbylamino, and heterocycle, and where R$_1$ and R$_2$ together with the P form a phosphole, aryl, or alkyl ring.

Alternatively, the process may use the supported phosphine compounds of Formula 2A with the process comprising the steps of:

a) contacting one or more phosphines of the Formula PR$_1$R$_2$X wherein X is a halogen, with one or more solid supports, resulting in one P in each phosphine being covalently bonded to Z; and b) optionally replacing one or both of R$_1$ and R$_2$ with any other R$_1$ or R$_2$. In this process the SS more preferably is polystyrene; L is —CH$_2$—; Z is selected from the group consisting of optionally-substituted carbon chain of 1–10 carbon atoms, —(NR$_4$)—, and —O—; R$_4$ is selected from the group consisting of chloro, cyclohexyl, n-propyl, i-propyl, n-butyl, phenyl, and t-butyl; and R$_1$ and R$_2$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$, and Q$_4$ are selected from the group consisting of hydrogen, hydrocarbyl, substituted hydrocarbyl, hydrocarbylamino, and heterocycle, and where R$_1$ and R$_2$ together with the P form a phosphole, aromatic, or alkyl ring.

Alternatively, the process may use the supported phosphine compounds of Formula 3A with the process comprising the steps of:

a) contacting no more than one molar equivalent of one or more phosphines of the Formula XR$_3$P—A—PR$_1$R$_2$ wherein X is a halogen, with at least two molar equivalents of one or more of Z, resulting in both of the P in each phosphine being covalently bonded to the Z; and b) optionally replacing one or more of R$_1$ and R$_2$ with any one or more of R$_1$ and R$_2$. In this process SS is more preferably polystyrene; L is —CH$_2$—; A is selected from the group consisting of an optionally-substituted carbon chain of 1–3 carbon atoms and an optionally-substituted carbon ring of 6–12 carbon atoms; Z is selected from the group consisting of an optionally-substituted carbon chain of 1–10 carbon atoms, —(NR$_4$)—, and —O—; R$_4$ is selected from the group consisting of chloro, cyclohexyl, n-propyl, i-propyl, n-butyl, phenyl, and t-butyl; R$_1$ and R$_2$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$, and Q$_4$ are selected from the group consisting of hydrogen, hydrocarbyl, substituted hydrocarbyl, hydrocarbylamino, and heterocycle, and where R$_1$ and R$_2$ together with the P form a phosphole, aryl or alkyl ring.

Alternatively, the process may use the supported phosphine compounds of Formula 4A with the process comprising the steps of:

a) contacting one or more phosphines of the Formula HP(=O)R$_3$—A—PR$_1$R$_2$ with one or more solid supports, resulting in one P in each phosphine being covalently bonded to Z; and b) optionally replacing one or more of $R_1$, $R_2$, and $R_3$ with any one or more of $R_1$, $R_2$, and $R_3$. In this process the SS is more preferably polystyrene; L is —$CH_2$—; Z is selected from the group consisting of optionally-substituted carbon chain of 1–10 carbon atoms, —($NR_4$)—, and —O—; $R_4$ is selected from the group consisting of chloro, cyclohexyl, n-propyl, i-propyl, n-butyl, phenyl, and t-butyl; and $R_1$, $R_2$, and $R_3$ are independently selected from the group consisting of hydrogen, Cl, alkyl, alkenyl, aryl, $SQ_1$, $OQ_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle, and where $R_1$ and $R_2$ together with the P form a phosphole, aryl, or alkyl ring.

Alternatively, the process may use the supported phosphine compounds of Formula 5A with the process comprising the steps of:

a) contacting one or more phosphines of the Formula HP(=O)$R_1R_2$ with one or more solid supports of the formula

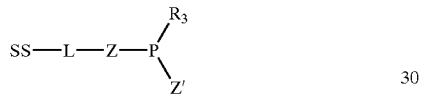

wherein the P in the solid support is covalently bonded to Z and Z' is selected from the group consisting of alkenyls, resulting in the phosphorus in each phosphine being covalently bonded to the phosphorus in the solid support via Z', and b) optionally replacing one or more of $R_1$, $R_2$, and $R_3$ with any one or more of $R_1$, $R_2$, and $R_3$. In this process the SS is more preferably polystyrene; L is —$CH_2$—; Z is selected from the group consisting of optionally-substituted carbon chain of 1–10 carbon atoms, —($NR_4$)—, and —O—; A is selected from the group consisting of an optionally-substituted carbon chain of 1–3 carbon atoms and an optionally-substituted carbon ring of 6–12 carbon atoms; $R_4$ is selected from the group consisting of chloro, cyclohexyl, n-propyl, i-propyl, n-butyl, phenyl, and t-butyl; and $R_1$, $R_2$, and $R_3$ are independently selected from the group consisting of hydrogen, Cl, alkyl, alkenyl, aryl, $SQ_1$, $OQ_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle; and where $R_1$ and $R_2$ together with the P form a phosphole, aryl, or alkyl ring.

Additionally, the invention is directed at a process to prepare a phosphine compounds of Formulae 8, 9, 10, 11, and 12

8

9

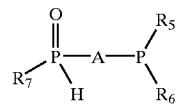
10

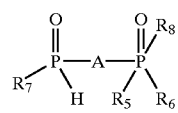
11

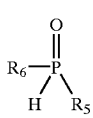
12 wherein:

A is a divalent group of 1–12 aliphatic or aromatic carbon atoms, linear or branched, optionally containing one or more heteroatoms or organometallic groups;

$R_5$, $R_6$, $R_7$, and $R_8$ are independently selected from the group consisting of hydrogen, hydrocarbyl, substituted hydrocarbyl, heterocycle, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle;

any of $R_5$, $R_6$, $R_7$, and $R_8$ can optionally together with any other of $R_5$, $R_6$, $R_7$, and $R_8$ form a ring;

the process comprising the steps of:

a) contacting (i) a supported phosphine selected from the group consisting of Formulae 1, 2, 3, 4, 5, 6, and 7

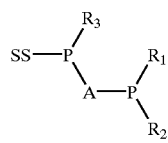
1

2

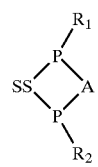
3

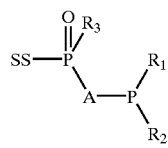
4

-continued

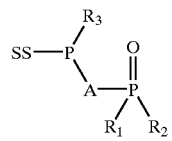
5

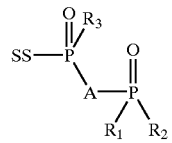
6

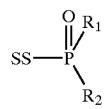
7 wherein:

SS is a solid support wherein at least one P in the phosphine is attached indirectly or directly to the solid support via one or more covalent bonds; A is a divalent group of 1–12 aliphatic or aromatic carbon atoms, linear or branched, optionally containing one or more heteroatoms or organometal groups; $R_1$, $R_2$ and $R_3$ are independently selected from the group consisting of hydrogen, hydrocarbyl, substituted hydrocarbyl, heterocycle, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle, and $R_2$ and $R_3$ together, $R_1$ and $R_3$ together, or $R_1$ and $R_2$ together can optionally form a ring with (ii) a compound of the Formula $ER_9$, wherein E is an electrophilic group and $R_9$ is selected from the group consisting of hydrogen, hydrocarbyl, substituted hydrocarbyl, heterocycle, organometal, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle; thereby forming the corresponding compound of Formulae 1, 2, 3, 4, 5, 6, and 7; and b) optionally replacing one or more substituent of the group $R_5$, $R_6$, $R_7$, and $R_8$ with any other substituent of the group $R_5$, $R_6$, $R_7$, and $R_8$.

More preferably, the process for preparing a phosphine compound uses a supported phosphine selected from the group consisting of Formulae 1A, 2A, 3A, 4A, 5A, 6A, and 7A

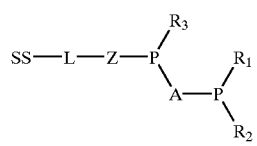
1A

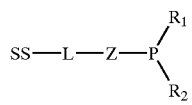
2A

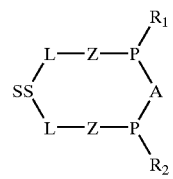
3A

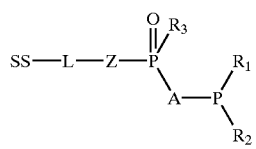
4A

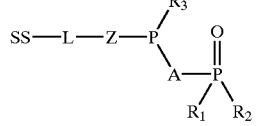
5A

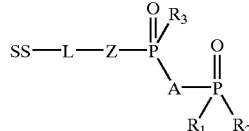
6A

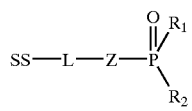
7A wherein:

Z is a divalent attaching group covalently attached to at least one P in the phosphine, selected from the group consisting of hydrocarbylene, substituted hydrocarbylene, —O—, —S—, and —$NR_4$—, where $R_4$ is selected from the group consisting of an optionally-substituted hydrocarbyl and halogen; L is a divalent linking group covalently attached to Z and to SS, selected from the group consisting of optionally-substituted chains of from 1 to 12 linear, branched, and cyclic carbon atoms; A is an optionally-substituted carbon chain of 1–3 carbon atoms; $R_5$, $R_6$, $R_7$, and $R_8$ are independently selected from the group consisting of hydrogen, Cl, alkyl, alkenyl, aryl, heterocycle, $SQ_1$, $OQ_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy; and any of $R_5$, $R_6$, $R_7$, and $R_8$ can optionally together with any other of $R_5$, $R_6$, $R_7$, and $R_8$ form a ring. Still more preferably in this process E is selected from the group consisting of hydrogen, $PCl_2$, and $SiMe_3$, and $R_5$ is a halogen.

Also in this process, the supported phosphine compound is selected from the group consisting of Formulae 1 and 3, and the phosphine compound is of Formula 8. Also in this process at least one substitutent of the group $R_5$, $R_6$, $R_7$, and $R_8$ differs from the other substitutent of the group $R_5$, $R_6$, $R_7$, and $R_8$.

Also in this process, Z is preferably selected from the group consisting of optionally-substituted carbon chain of 1–10 carbon atoms, —(NR$_4$)—, and —O—; A is preferably selected from the group consisting of an optionally-substituted carbon chain of 1–3 carbon atoms and an optionally-substituted carbon ring of 6–12 carbon atoms; R$_5$, R$_6$, R$_7$, and R$_8$ are preferably independently selected from the group consisting of hydrogen, Cl, alkyl, alkenyl, aryl, heterocycle, SQ$_1$, OQ$_2$, and PQ$_3$Q$_4$, where Q$_1$, Q$_2$, Q$_3$, and Q$_4$ are preferably independently selected from the group consisting of hydrogen, hydrocarbyl, substituted hydrocarbyl, hydrocarbylamino, alkoxy, aryloxy, and heterocycle; and any substituent of the group R$_5$, R$_6$, R$_7$, and R$_8$ can optionally together with any other substituent of the group R$_5$, R$_6$, R$_7$, and R$_8$ form a ring.

Alternatively, the process may use the supported phosphine compound of Formula 2 and the phosphine compound of Formula 9. In this process more preferably Z is selected from the group consisting of optionally-substituted carbon chain of 1–10 carbon atoms, —(NR$_4$)—, and —O—; A is selected from the group consisting of an optionally-substituted carbon chain of 1–3 carbon atoms and an optionally-substituted carbon ring of 6–12 carbon atoms; R$_5$, R$_6$, and R$_7$ are independently selected from the group consisting of hydrogen, Cl, alkyl, alkenyl, aryl, heterocycle, SQ$_1$, OQ$_2$, and PQ$_3$Q$_4$, where Q$_1$, Q$_2$, Q$_3$, and Q$_4$ are independently selected from the group consisting of hydrogen, hydrocarbyl, substituted hydrocarbyl, hydrocarbylamino, alkoxy, aryloxy, and heterocycle; and any substituent of the group R$_5$, R$_6$, and R$_7$ can optionally together with any other substituent of the group R$_5$, R$_6$, and R$_7$ form a ring.

Alternatively, the process may use the supported phosphine compound of Formula 4 and the phosphine compound of Formula 10. In this process more preferably Z is selected from the group consisting of optionally-substituted carbon chain of 1–10 carbon atoms, —(NR$_4$)—, and —O—; A is selected from the group consisting of an optionally-substituted carbon chain of 1–3 carbon atoms and an optionally-substituted carbon ring of 6–12 carbon atoms; R$_5$, R$_6$, and R$_7$ are independently selected from the group consisting of hydrogen, Cl, alkyl, alkenyl, aryl, heterocycle, SQ$_1$, OQ$_2$, and PQ$_3$Q$_4$, where Q$_1$, Q$_2$, Q$_3$, and Q$_4$ are independently selected from the group consisting of hydrogen, hydrocarbyl, substituted hydrocarbyl, hydrocarbylamino, alkoxy, aryloxy, and heterocycle; and any substituent of the group R$_5$, R$_6$, and R$_7$ can optionally together with any other substituent of the group R$_5$, R$_6$, and R$_7$ form a ring.

Alternatively, the process may use the supported phosphine compound selected from the group consisting of Formulae 3 and 5, and the phosphine compound of Formula 11. In this process more preferably Z is selected from the group consisting of optionally-substituted carbon chain of 1–10 carbon atoms, —(NR$_4$)—, and —O—; A is selected from the group consisting of an optionally-substituted carbon chain of 1–3 carbon atoms and an optionally-substituted carbon ring of 6–12 carbon atoms; R$_6$, R$_7$, and R$_8$ are independently selected from the group consisting of Cl, alkyl, alkenyl, aryl, heterocycle, SQ$_1$, OQ$_2$, and PQ$_3$Q$_4$, where Q$_1$, Q$_2$, Q$_3$, and Q$_4$ are independently selected from the group consisting of hydrogen, hydrocarbyl, substituted hydrocarbyl, hydrocarbylamino, alkoxy, aryloxy, and heterocycle; and any substituent of the group R$_6$, R$_7$, and R$_8$ can optionally together with any other substituent of the group R$_6$, R$_7$, and R$_8$ form a ring.

Alternatively, the process may use the supported phosphine compound of Formula 2 and the phosphine compound of Formula 12. I this process more preferably Z is selected from the group consisting of optionally-substituted carbon chain of 1–10 carbon atoms, —(NR$_4$)—, and —O—; A is selected from the group consisting of an optionally-substituted carbon chain of 1–3 carbon atoms and an optionally-substituted carbon ring of 6–12 carbon atoms; R$_5$ and R$_6$ are independently selected from the group consisting of hydrogen, Cl, alkyl, alkenyl, aryl, heterocycle, SQ$_1$, OQ$_2$, and PQ$_3$Q$_4$, where Q$_1$, Q$_2$, Q$_3$, and Q$_4$ are independently selected from the group consisting of hydrogen, hydrocarbyl, substituted hydrocarbyl, hydrocarbylamino, alkoxy, aryloxy, and heterocycle; and any substituent of the group R$_5$ and R$_6$ can optionally together with any other substituent of the group R$_5$ and R$_6$ form a ring.

This invention is still further directed to a process to prepare a combinatorial library of phosphine compounds selected from the group consisting of Formulae 8, 9, 10, 1 1, and 12

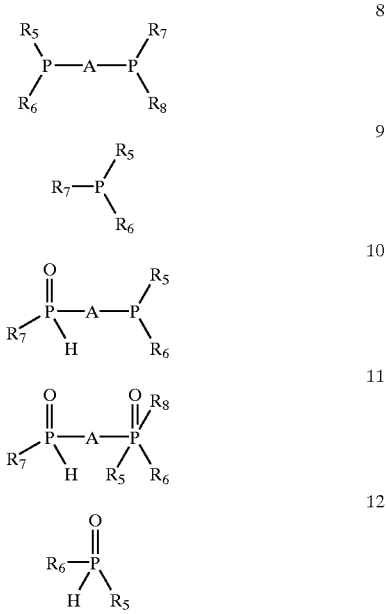

wherein:

A is a divalent group of 1–12 aliphatic or aromatic carbon atoms, linear or branched, optionally containing one or more heteroatoms or organometallic groups; R$_5$, R$_6$, R$_7$, and R$_8$ are independently selected from the group consisting of hydrogen, Cl, alkyl, alkenyl, aryl, heterocycle, SQ$_1$, OQ$_2$, and PQ$_3$Q$_4$, where Q$_1$, Q$_2$, Q$_3$, and Q$_4$ are independently selected from the group consisting of hydrogen, hydrocarbyl, substituted hydrocarbyl, hydrocarbylamino, alkoxy, aryloxy; and any of R$_5$, R$_6$, R$_7$, and R$_8$ can optionally together with any other of R$_5$, R$_6$, R$_7$, and R$_8$ form a ring;

the process comprising the steps of:
  a) contacting (i) one or more supported phosphines selected from the group consisting of Formulae 1, 2, 3, 4, 5, 6, and 7

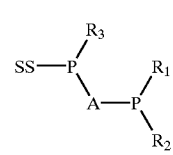

-continued

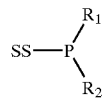
2

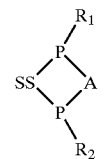
3

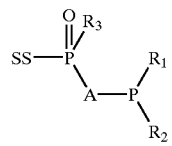
4

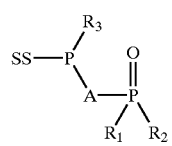
5

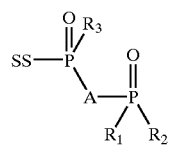
6

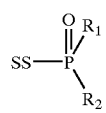
7 wherein:
SS is a solid support wherein at least one P in each phosphine is attached indirectly or directly to the solid support via one or more covalent bonds; A is a divalent group of 1–12 aliphatic or aromatic carbon atoms, linear or branched, optionally containing one or more heteroatoms or organometallic groups; $R_1$, $R_2$, and $R_3$ are independently selected from the group consisting of hydrogen, hydrocarbyl, substituted hydrocarbyl, heterocycle, organometal, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle, and $R_2$ and $R_3$ together, $R_1$ and $R_3$ together, or $R_1$ and $R_2$ together can optionally form a ring with (ii) one or more compounds of the Formula $ER_9$, wherein E is an electrophilic group and $R_9$ is selected from the group consisting of hydrogen, hydrocarbyl, substituted hydrocarbyl, heterocycle, organometal, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle; thereby forming the corresponding compounds of Formulae 1, 2, 3, 4, 5, 6, and 7; and b) optionally replacing one or more substitutents of the group $R_5$, $R_6$, $R_7$, and $R_8$ with any other substitutent of the group $R_5$, $R_6$, $R_7$, and $R_8$.

More particularly the process may use the supported phosphine compounds of the group consisting of Formulae 1A, 2A, 3A, 4A, 5A, 6A, and 7A

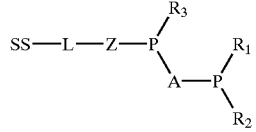
1A

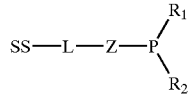
2A

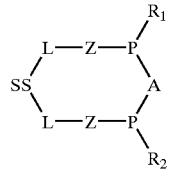
3A

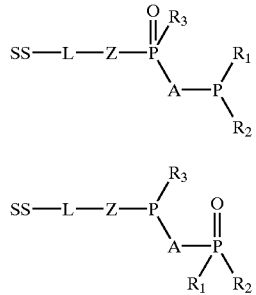
4A

5A

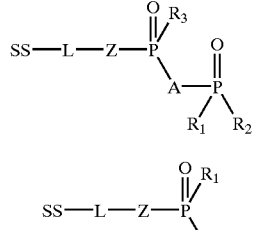
6A

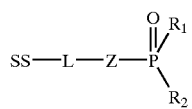
7A

wherein:
Z is a divalent attaching group covalently attached to at least one phosphorus in the phosphine, selected from the group consisting of hydrocarbylene, substituted hydrocarbylene, —O—, —S—, and —$NR_4$—, where $R_4$ is selected from the group consisting of an optionally-substituted hydrocarbyl and halogen; L is a divalent linking group covalently attached to Z and to SS, selected from the group consisting of optionally-substituted chains of from 1 to 12 linear, branched, and cyclic carbon atoms; A is an optionally-substituted carbon chain of 1–3 carbon atoms; $R_5$, $R_6$, $R_7$, and $R_8$ are independently selected from the group consisting of hydrogen, Cl, alkyl, alkenyl, aryl, heterocycle, $SQ_1$, $OQ_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy; and any of $R_5$, $R_6$, $R_7$, and $R_8$ can optionally together with any other of $R_5$, $R_6$, $R_7$, and $R_8$ form a ring.

In this process preferably E is selected from the group consisting of hydrogen, $PCl_2$, and $SiMe_3$, and $R_5$ is a halogen. Additionally in this process preferably the supported phosphine compounds are selected from the group consisting of Formulae 1 and 3, and the phosphine compound is Formula 8. More preferably in this process Z is selected from the group consisting of optionally-substituted carbon chain of 1–10 carbon atoms, —$(NR_4)$—, and —O—; A is selected from the group consisting of an optionally-substituted carbon chain of 1–3 carbon atoms and an optionally-substituted carbon ring of 6–12 carbon atoms; $R_5$, $R_6$, $R_7$, and $R_8$ are independently selected from the group consisting of hydrogen, Cl, alkyl, alkenyl, aryl, heterocycle, $SQ_1$, $OQ_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy, and heterocycle; and any of $R_5$, $R_6$, $R_7$, and $R_8$ can optionally together with any other of $R_5$, $R_6$, $R_7$, and $R_8$ form a ring.

Alternatively in this process the preferred supported phosphine compounds are of Formula 2, and the phosphine compounds are of Formula 9. More preferably in this process Z is selected from the group consisting of optionally-substituted carbon chain of 1–10 carbon atoms, —$(NR_4)$—, and —O—; A is selected from the group consisting of an optionally-substituted carbon chain of 1–3 carbon atoms and an optionally-substituted carbon ring of 6–12 carbon atoms; $R_5$, $R_6$, and $R_7$, are independently selected from the group consisting of hydrogen, Cl, alkyl, alkenyl, aryl, heterocycle, $SQ_1$, $OQ_2$, and $PQ_3Q_4$, where $Q_1$, $Q_2$ $Q_3$, and $Q_4$ are independently selected from the group consisting of hydrogen, hydrocarbyl, substituted hydrocarbyl, hydrocarbylamino, alkoxy, aryloxy, and heterocycle; and any of $R_5$, $R_6$, and $R_7$ can optionally together with any other of $R_5$, $R_6$, and $R_7$ form a ring.

Alternatively in this process the preferred supported phosphine compounds are of Formula 4 and the phosphine compounds are of Formula 10. More preferably in this process Z is selected from the group consisting of optionally-substituted carbon chain of 1–10 carbon atoms, —$(NR_4)$—, and —O—; A is selected from the group consisting of an optionally-substituted carbon chain of 1–3 carbon atoms and an optionally-substituted carbon ring of 6–12 carbon atoms; $R_5$, $R_6$, and $R_7$ are independently selected from the group consisting of hydrogen, Cl, alkyl, alkenyl, aryl, heterocycle, $SQ_1$, $OQ_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy, and heterocycle; and any of $R_5$, $R_6$, and $R_7$ can optionally together with any other of $R_5$, $R_6$, and $R_7$ form a ring.

Alternatively in this process the preferred supported phosphine compounds are selected from the group consisting of Formulae 3 and 5, and the phosphine compounds are of Formula 11. More preferably in this process Z is selected from the group consisting of optionally-substituted carbon chain of 1–10 carbon atoms, —$(NR_4)$—, and —O—; A is selected from the group consisting of an optionally-substituted carbon chain of 1–3 carbon atoms and an optionally-substituted carbon ring of 6–12 carbon atoms; $R_6$, $R_7$, and $R_8$ are independently selected from the group consisting of Cl, alkyl, alkenyl, aryl, heterocycle, $SQ_1$, $Q_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy, and heterocycle; and any of $R_6$, $R_7$, and $R_8$ can optionally together with any other of $R_6$, $R_7$, and $R_8$ form a ring.

Alternatively in this process the preferred supported phosphine compounds are of Formula 2, and the phosphine compounds are of Formula 12. More preferably in this process Z is selected from the group consisting of optionally-substituted carbon chain of 1–10 carbon atoms, —$(NR_4)$—, and —O—; A is selected from the group consisting of an optionally-substituted carbon chain of 1–3 carbon atoms and an optionally-substituted carbon ring of 6–12 carbon atoms; $R_5$ and $R_6$ are independently selected from the group consisting of hydrogen, Cl, alkyl, alkenyl, aryl, heterocycle, $SQ_1$, $O_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy, and heterocycle; and any of $R_5$ and $R_6$ can optionally together with any other of $R_5$ and $R_6$ form a ring.

This invention is still further directed to a supported phosphine compound selected from the group consisting of Formulae 1, 2, 3, 4, 5, 6, and 7

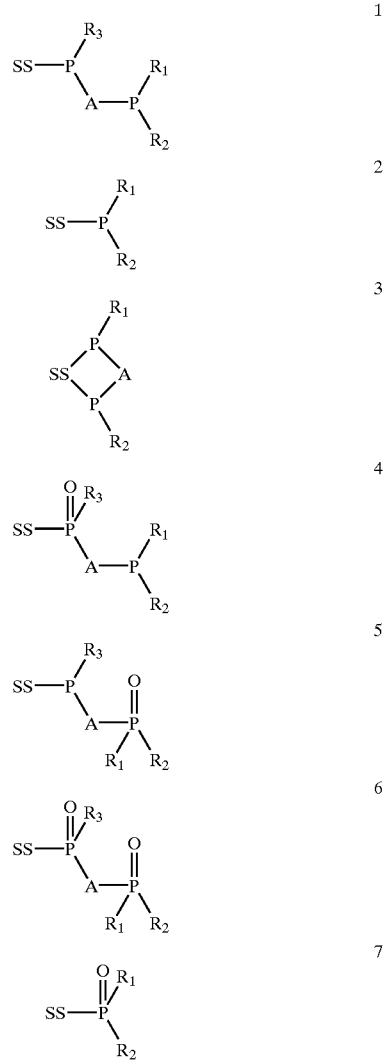

wherein:
  SS is a solid support wherein at least one P in each phosphine is attached indirectly or directly to the solid support via one or more covalent bonds; A is a divalent group of 1–12 aliphatic or aromatic carbon atoms, linear or branched, optionally containing one or more heteroatoms or organometallic groups; $R_1$, $R_2$, and $R_3$ are independently selected from the group consisting of hydrogen, hydrocarbyl, substituted hydrocarbyl, heterocycle, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle, and $R_2$ and $R_3$ together, $R_1$ and $R_3$ together, or $R_1$ and $R_2$ together can optionally form a ring.

More preferably the supported phosphine compound is selected from the group consisting of Formulae 1A, 2A, 3A, 4A, 5A, 6A, and 7A

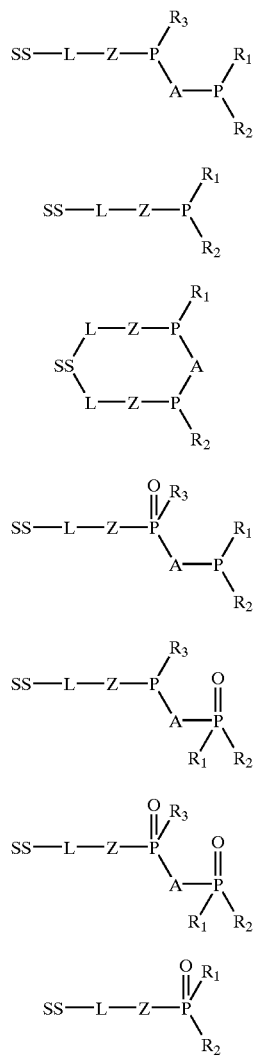

wherein:
Z is a divalent attaching group covalently attached to at least one phosphorus in the phosphine, selected from the group consisting of hydrocarbylene, substituted hydrocarbylene, —O—, —S—, and —$NR_4$—, where $R_4$ is selected from the group consisting of an optionally-substituted hydrocarbyl and halogen; and L is a divalent linking group covalently attached to Z and to SS, selected from the group consisting of optionally-substituted chains of from 1 to 12 linear, branched, and cyclic carbon atoms.

Alternatively, the preferred supported phosphine compound is Formula 1A. More preferably in this supported phosphine compound the SS is polystyrene; L is —$CH_2$—; A is selected from the group consisting of an optionally-substituted carbon chain of 1–3 carbon atoms and an optionally-substituted carbon ring of 6–12 carbon atoms; Z is selected from the group consisting of an optionally-substituted carbon chain of 1–10 carbon atoms, —($NR_4$)—, and —O—; $R_4$ is selected from the group consisting of chloro, cyclohexyl, n-propyl, i-propyl, n-butyl, phenyl, and t-butyl; $R_1$, $R_2$, and $R_3$ are independently selected from the group consisting of hydrogen, Cl, alkyl, alkenyl, aryl, $SQ_1$, $OQ_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle, and where $R_1$ and $R_2$ together with the P form a phosphole, aryl, or alkyl ring.

Alternatively, the preferred supported phosphine compound is Formula 2A. More preferably in this supported phosphine compound the SS is polystyrene; L is —$CH_2$—; Z is selected from the group consisting of optionally-substituted carbon chain of 1–10 carbon atoms, —($NR_4$)—, and —O—; $R_4$ is selected from the group consisting of chloro, cyclohexyl, n-propyl, i-propyl, n-butyl, phenyl, and t-butyl; and $R_1$ and $R_2$ are independently selected from the group consisting of hydrogen, Cl, alkyl, alkenyl, aryl, $SQ_1$, $OQ_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle, and where $R_1$ and $R_2$ together with the P form a phosphole, aromatic, or alkyl ring.

Alternatively, the preferred supported phosphine compound is Formula 3A. More preferably in this supported phosphine compound the SS is polystyrene; L is —$CH_2$—; A is selected from the group consisting of an optionally-substituted carbon chain of 1–3 carbon atoms and an optionally-substituted carbon ring of 6–12 carbon atoms; Z is selected from the group consisting of an optionally-substituted carbon chain of 1–10 carbon atoms, —($NR_4$)—, and —O—; $R_4$ is selected from the group consisting of chloro, cyclohexyl, n-propyl, i-propyl, n-butyl, phenyl, and t-butyl; $R_1$ and $R_2$ are independently selected from the group consisting of hydrogen, Cl, alkyl, alkenyl, aryl, $SQ_1$, $OQ_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle, and where $R_1$ and $R_2$ together with the P form a phosphole, aryl, or alkyl ring.

Alternatively, the preferred supported phosphine compound is Formula 4A. More preferably in the supported phosphine compound of claim 63 the SS is polystyrene; L is —CH—; Z is selected from the group consisting of optionally-substituted carbon chain of 1–10 carbon atoms, —($NR_4$)—, and —O—; $R_4$ is selected from the group consisting of chloro, cyclohexyl, n-propyl, i-propyl, n-butyl, phenyl, and t-butyl; and $R_1$, $R_2$, and $R_3$ are independently selected from the group consisting of hydrogen, Cl, alkyl, alkenyl, aryl, $SQ_1$, $OQ_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle, and where $R_1$ and $R_2$ together with the P form a phosphole, aryl, or alkyl ring.

Alternatively, the preferred supported phosphine compound is Formula 5A. More preferably in this supported phosphine compound the SS is polystyrene; L is —$CH_2$—; Z is selected from the group consisting of optionally-substituted carbon chain of 1–10 carbon atoms, —($NR_4$)—, and —O—; A is selected from the group consisting of an optionally-substituted carbon chain of 1–3 carbon atoms and an optionally-substituted carbon ring of 6–12 carbon atoms; $R_4$ is selected from the group consisting of chloro, cyclohexyl, n-propyl, i-propyl, n-butyl, phenyl, and t-butyl; and $R_1$, $R_2$, and $R_3$ are independently selected from the group consisting of hydrogen, Cl, alkyl, alkenyl, aryl, $SQ_1$, $OQ_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle; and where $R_1$ and $R_2$ together with the P form a phosphole, aryl, or alkyl ring.

This invention is still further directed to a combinatorial library of supported phosphine compounds selected from the group consisting of Formulae 1, 2, 3, 4, 5, 6, and 7

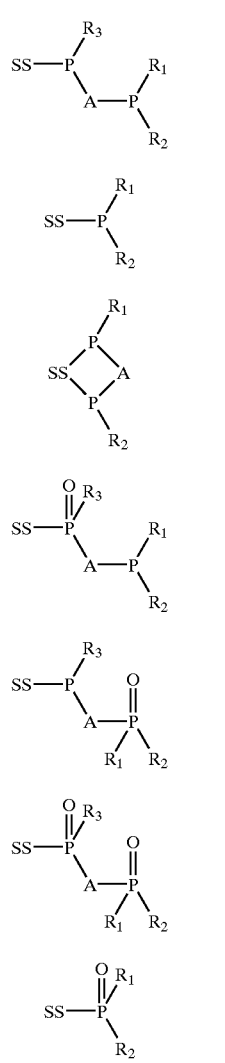

hydrogen, hydrocarbyl, substituted hydrocarbyl, hydrocarbylamino, alkoxy, aryloxy, and heterocycle, and $R_2$ and $R_3$ together, $R_1$ and $R_3$ together, or $R_1$ and $R_2$ together can optionally form a ring.

Preferably the combinatorial library of this invention uses the supported phosphine compounds selected from the group consisting of Formulae 1A, 2A, 3A, 4A, 5A, 6A, and 7A

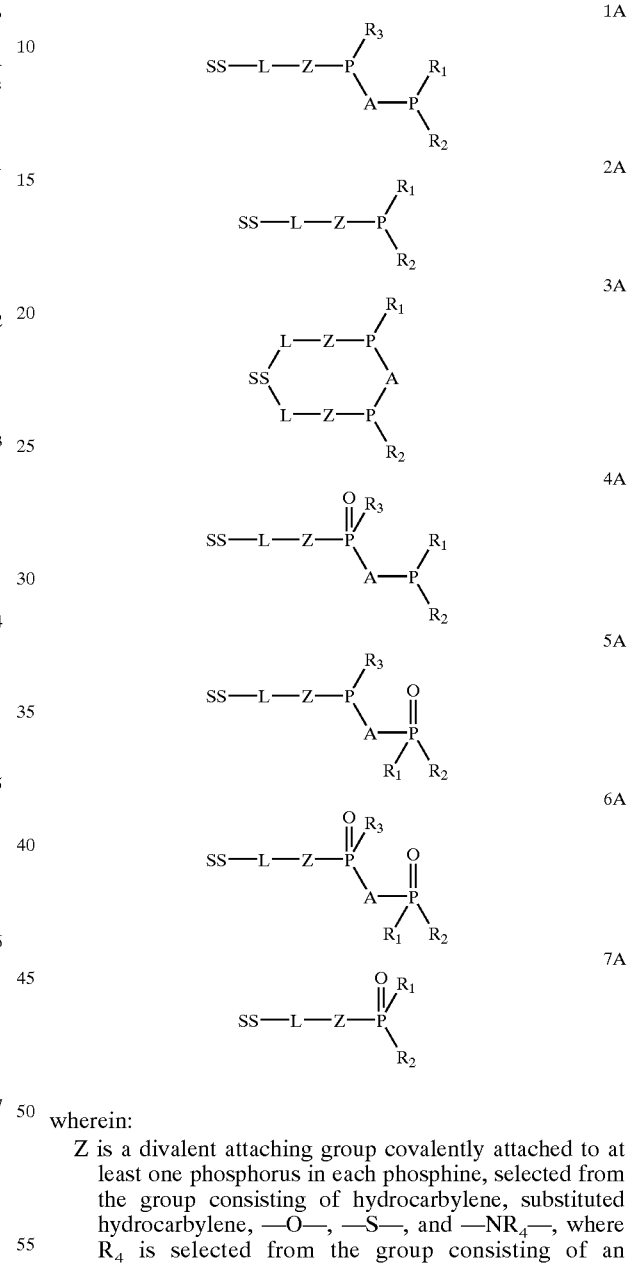

wherein:
Z is a divalent attaching group covalently attached to at least one phosphorus in each phosphine, selected from the group consisting of hydrocarbylene, substituted hydrocarbylene, —O—, —S—, and —$NR_4$—, where $R_4$ is selected from the group consisting of an optionally-substituted hydrocarbyl and halogen; and L is a divalent linking group covalently attached to Z and to SS, selected from the group consisting of optionally-substituted chains of from 1 to 12 linear, branched, and cyclic carbon atoms.

wherein:
SS is a solid support wherein at least one P in each phosphine is attached indirectly or directly to the solid support via one or more covalent bonds; A is a divalent group of 1–12 aliphatic or aromatic carbon atoms, linear or branched, optionally containing one or more heteroatoms or organometallic groups; $R_1$, $R_2$, and $R_3$ are independently selected from the group consisting of hydrogen, hydrocarbyl, substituted hydrocarbyl, heterocycle, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of Preferably, the combinatorial library uses the supported phosphine compounds of Formula 1A. More preferably in this combinatorial the SS is polystyrene; L is —$CH_2$—; A is selected from the group consisting of an optionally-substituted carbon chain of 1–3 carbon atoms and an optionally-substituted carbon ring of 6–12 carbon atoms; Z is selected from the group consisting of an optionally-substituted carbon chain of 1–10 carbon atoms, —(NR$_4$)—, and —O—; R$_4$ is selected from the group consisting of chloro, cyclohexyl, n-propyl, i-propyl, n-butyl, phenyl, and t-butyl; R$_1$, R$_2$, and R$_3$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$, and Q$_4$ are selected from the group consisting of hydrogen, hydrocarbyl, substituted hydrocarbyl, hydrocarbylamino, and heterocycle, and where R$_1$ and R$_2$ together with the P form a phosphole, aryl, or alkyl ring.

Alternatively, the combinatorial library uses the supported phosphine compounds of Formula 2A. More preferably in this combinatorial the SS is polystyrene; L is —CH$_2$—; Z is selected from the group consisting of optionally-substituted carbon chain of 1–10 carbon atoms, —(NR$_4$)—, and —O—; R$_4$ is selected from the group consisting of chloro, cyclohexyl, n-propyl, i-propyl, n-butyl, phenyl, and t-butyl; and R$_1$ and R$_2$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$, and Q$_4$ are selected from the group consisting of hydrogen, hydrocarbyl, substituted hydrocarbyl, hydrocarbylamino, and heterocycle, and where R$_1$ and R$_2$ together with the P form a phosphole, aromatic, or alkyl ring.

Alternatively, the combinatorial library uses the supported phosphine compounds of Formula 3A. More preferably in this combinatorial library the SS is polystyrene; L is —CH—; A is selected from the group consisting of an optionally-substituted carbon chain of 1–3 carbon atoms and an optionally-substituted carbon ring of 6–12 carbon atoms; Z is selected from the group consisting of an optionally-substituted carbon chain of 1–10 carbon atoms, —(NR$_4$)—, and —O—; R$_4$ is selected from the group consisting of chloro, cyclohexyl, n-propyl, i-propyl, n-butyl, phenyl, and t-butyl; R$_1$ and R$_2$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$, and Q$_4$ are selected from the group consisting of hydrogen, hydrocarbyl, substituted hydrocarbyl, hydrocarbylamino, and heterocycle, and where R$_1$ and R$_2$ together with the P form a phosphole, aryl, or alkyl ring.

Alternatively, the combinatorial library uses the supported phosphine compounds of Formula 4A. More preferably in this combinatorial library the SS is polystyrene; L is —CH$_2$—; Z is selected from the group consisting of optionally-substituted carbon chain of 1–10 carbon atoms, —(NR$_4$)—, and —O—; R$_4$ is selected from the group consisting of chloro, cyclohexyl, n-propyl, i-propyl, n-butyl, phenyl, and t-butyl; and R$_1$, R$_2$, and R$_3$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$, and Q$_4$ are selected from the group consisting of hydrogen, hydrocarbyl, substituted hydrocarbyl, hydrocarbylamino, and heterocycle, and where R$_1$ and R$_2$ together with the P form a phosphole, aryl, or alkyl ring.

Alternatively, the combinatorial library uses the supported phosphine compounds of Formula 5A, more preferably in this combinatorial library the SS is polystyrene; L is —CH—; Z is selected from the group consisting of optionally-substituted carbon chain of 1–10 carbon atoms, —(NR$_4$)—, and —O—; A is selected from the group consisting of an optionally-substituted carbon chain of 1–3 carbon atoms and an optionally-substituted carbon ring of 6–12 carbon atoms; R$_4$ is selected from the group consisting of chloro, cyclohexyl, n-propyl, i-propyl, n-butyl, phenyl, and t-butyl; and R$_1$, R$_2$, and R$_3$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$, and Q$_4$ are selected from the group consisting of hydrogen, hydrocarbyl, substituted hydrocarbyl, hydrocarbylamino, and heterocycle; and where R$_1$ and R$_2$ together with the P form a phosphole, aryl, or alkyl ring.

The invention is still further directed to a combinatorial library of phosphine compounds selected from the group consisting of Formulae 8, 9, 10, 11, and 12

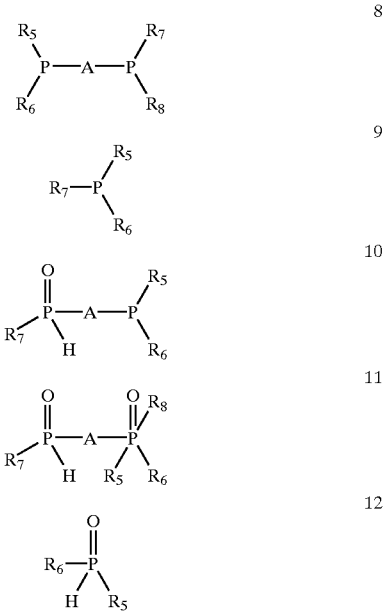

wherein:

A is a divalent group of 1–12 aliphatic or aromatic carbon atoms, linear or branched, optionally containing one or more heteroatoms or organometallic groups; R$_5$, R$_6$, R$_7$, and R$_8$ are independently selected from the group consisting of hydrocarbyl, substituted hydrocarbyl, heterocycle, organometal, Cl, Br, I, SQ$_1$, OQ$_2$, PQ$_3$Q$_4$, and NQ$_5$Q$_6$, where Q$_1$, Q$_2$, Q$_3$, Q$_4$, Q$_5$, and Q$_6$ are independently selected from the group consisting of hydrogen, hydrocarbyl, substituted hydrocarbyl, hydrocarbylamino, alkoxy, aryloxy, and heterocycle; R$_5$, R$_6$, R$_7$, and R$_8$ are independently selected from the group consisting of hydrocarbyl, substituted hydrocarbyl, heterocycle, organometal, Cl, Br, I, SQ , OQ$_2$, PQ$_3$Q$_4$, and NQ$_5$Q$_6$, where Q$_1$, Q$_2$, Q$_3$, Q$_4$, Q$_5$, and Q$_6$ are independently selected from the group consisting of hydrogen, hydrocarbyl, substituted hydrocarbyl, hydrocarbylamino, alkoxy, aryloxy, and heterocycle; and any substituent of the group R$_5$, R$_6$, R$_7$, and R$_8$ can optionally together with any other substituent of the group R$_5$, R$_6$, R$_7$, and R$_8$ form a ring.

Preferably in this combinatorial library of phosphine compounds A is an optionally-substituted carbon chain of 1–3 carbon atoms; R$_5$, R$_6$, R$_7$, and R$_8$ are independently selected from the group consisting of hydrogen, Cl, alkyl, alkenyl, aryl, heterocycle, SQ$_1$, OQ$_2$, and PQ$_3$Q$_4$, where Q$_1$, Q$_2$, Q$_3$, and Q$_4$ are independently selected from the group consisting of hydrogen, hydrocarbyl, substituted hydrocarbyl, hydrocarbylamino, alkoxy, aryloxy, and heterocycle; and any of R$_5$, R$_6$, R$_7$, and R$_8$ can optionally together with any other of R$_5$, R$_6$, R$_7$, and R$_8$ form a ring.

Preferably in this combinatorial library the phosphine compounds are of Formula 8. More preferably in this combinatorial library at least one of the substitutents of the group R$_5$, R$_6$, R$_7$, and R$_8$ differs from the other substituents of the group R$_5$, R$_6$, R$_7$, and R$_8$.

Alternatively in this combinatorial library of phosphine compounds A is an optionally-substituted carbon chain of 1–3 carbon atoms; $R_5$, $R_6$, $R_7$, and $R_8$ are independently selected from the group consisting of hydrogen, Cl, alkyl, alkenyl, aryl, heterocycle, $SQ_1$, $OQ_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy, and heterocycle; and any substituent of the group $R_5$, $R_6$, $R_7$, and $R_8$ can optionally together with any other substituent of the group $R_5$, $R_6$, $R_7$, and $R_8$ form a ring.

Preferably in this combinatorial library the phosphine compounds are of Formula 9. More preferably in this combinatorial library A is an optionally-substituted carbon chain of 1–3 carbon atoms; $R_5$, $R_6$, and $R_7$ are independently selected from the group consisting of hydrogen, Cl, alkyl, alkenyl, aryl, heterocycle, $SQ_1$, $OQ_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy, and heterocycle; and any substituent of the group $R_5$, $R_6$, and $R_7$ can optionally together with any other substituent of the group $R_5$, $R_6$, and $R_7$ form a ring.

Preferably in this combinatorial library the phosphine compounds are of Formula 10. More preferably in this combinatorial library A is an optionally-substituted carbon chain of 1–3 carbon atoms; $R_5$, $R_6$, and $R_7$ are independently selected from the group consisting of hydrogen, Cl, alkyl, alkenyl, aryl, heterocycle, $SQ_1$, $OQ_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy, and heterocycle; and any substituent of the group $R_5$, $R_6$, and $R_7$ can optionally together with any other substituent of the group $R_5$, $R_6$, and $R_7$ form a ring.

Preferably in this combinatorial library the phosphine compounds are of Formula 11. More preferably in this combinatorial library A is an optionally-substituted carbon chain of 1–3 carbon atoms; $R_6$, $R_7$, and $R_8$ are independently selected from the group consisting of Cl, alkyl, alkenyl, aryl, heterocycle, $SQ_1$, $OQ_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy, and heterocycle; and any substituent of the group $R_6$, $R_7$, and $R_8$ can optionally together with any other substituent of the group $R_6$, $R_7$, and $R_8$ form a ring.

Preferably in this combinatorial library the phosphine compounds are of Formula 12. More preferably in this combinatorial library A is an optionally-substituted carbon chain of 1–3 carbon atoms; $R_5$ and $R_6$ are independently selected from the group consisting of hydrogen, Cl, alkyl, alkenyl, aryl, heterocycle, $SQ_1$, $OQ_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy, and heterocycle; and any of $R_5$ and $R_6$ can optionally together with any other of $R_5$ and $R_6$ form a ring.

This invention is still further directed to a coordination compound comprising one or more transition metals complexed to a ligand selected from the group consisting of Formulae 1, 2, 3, 4, 5, 6, and 7

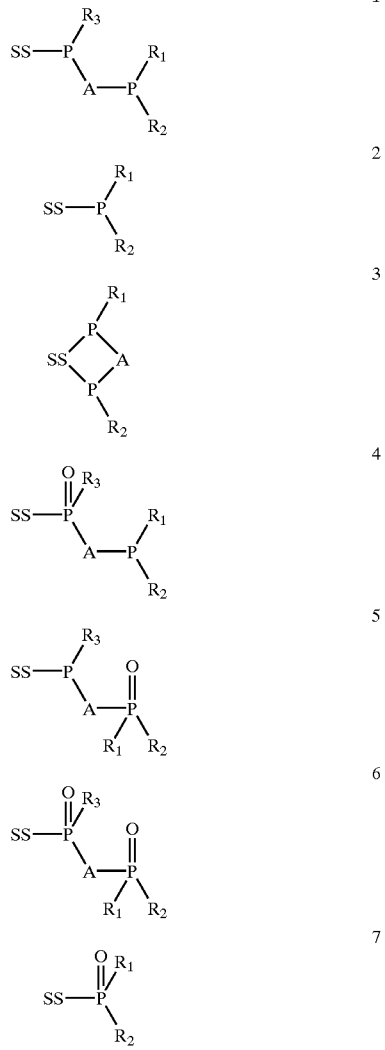

wherein:

SS is a solid support wherein at least one P in each phosphine is attached indirectly or directly to the solid support via one or more covalent bonds; A is a divalent group of 1–12 aliphatic or aromatic carbon atoms, linear or branched, optionally containing one or more heteroatoms or organometal groups; $R_1$, $R_2$, and $R_3$ are independently selected from the group consisting of hydrogen, hydrocarbyl, substituted hydrocarbyl, heterocycle, organometal, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle, and $R_2$ and $R_3$ together, $R_1$ and $R_3$ together, or $R_1$ and $R_2$ together can optionally form a ring.

Preferably the transition metal is selected from Periodic Group VIII.

Preferably the coordination compound is selected from the group consisting of Formulae 1A, 2A, 3A, 4A, 5A, 6A, and 7A

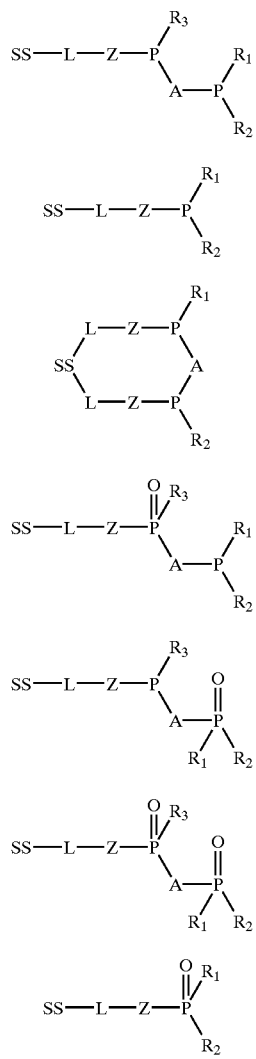

1A
2A
3A
4A
5A
6A
7A wherein:

Z is a divalent attaching group covalently attached to at least one phosphorus in the phosphine, selected from the group consisting of hydrocarbylene, substituted hydrocarbylene. —O—, —S—, and —NR$_4$—, where R$_4$ is selected from the group consisting of an optionally-substituted hydrocarbyl and halogen; and L is a divalent linking group covalently attached to Z and to SS, selected from the group consisting of optionally-substituted chains of from 1 to 12 linear, branched, and cyclic carbon atoms.

More preferably the coordination compound is Formula 1A. In this coordination compound still more preferably the SS is polystyrene; L is —CH$_2$—; A is selected from the group consisting of an optionally-substituted carbon chain of 1–3 carbon atoms and an optionally-substituted carbon ring of 6–12 carbon atoms; Z is selected from the group consisting of an optionally-substituted carbon chain of 1–10 carbon atoms, —(NR$_4$)—, and —O—; R$_4$ is selected from the group consisting of chloro, cyclohexyl, n-propyl, i-propyl, n-butyl, phenyl, and t-butyl; R$_1$, R$_2$, and R$_3$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$, and Q$_4$ are selected from the group consisting of hydrogen, hydrocarbyl, substituted hydrocarbyl, hydrocarbylamino, and heterocycle, and where R$_1$ and R$_2$ together with the P form a phosphole, aryl or alkyl ring; and the transition metal is Rh.

Most preferably the coordination compound is polymer-bound 1-(1,1-di-n-propylphosphino)-2-n-propylphosphinoethane and (1,5-cyclooctadiene)-rhodium (I) chloride dimer.

This invention is still further directed to a combinatorial library of coordination compounds comprising one or more transition metals complexed to one or more ligands selected from the group consisting of Formulae 1, 2, 3, 4, 5, 6, and 7

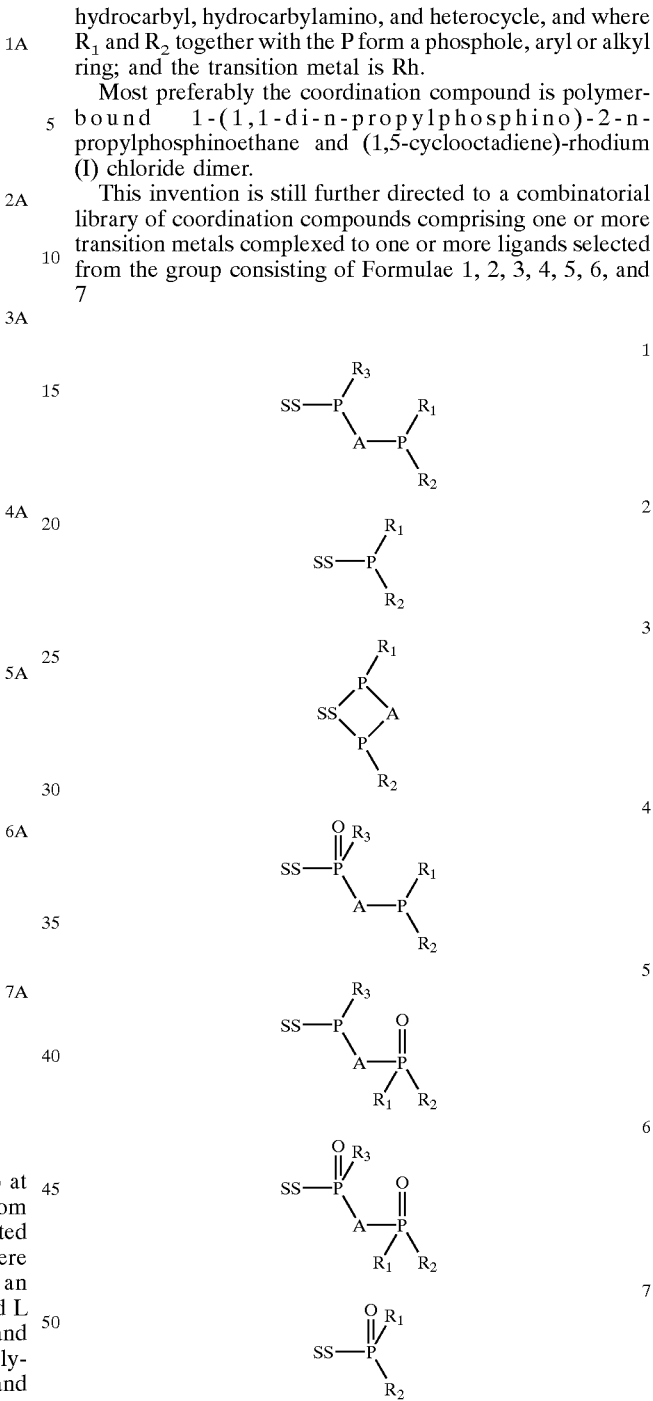

1
2
3
4
5
6
7 wherein:

SS is a solid support wherein at least one P in each phosphine is attached indirectly or directly to the solid support via one or more covalent bonds; A is a divalent group of 1–12 aliphatic or aromatic carbon atoms, linear or branched, optionally containing one or more heteroatoms or organometallic groups; R$_1$, R$_2$, and R$_3$ are independently selected from the group consisting of hydrogen, hydrocarbyl, substituted hydrocarbyl, heterocycle, organometal, Cl, Br, I, SQ$_1$, OQ$_2$, PQ$_3$Q$_4$, and NQ$_5$Q$_6$, where Q$_1$, Q$_2$, Q$_3$, Q$_4$, Q$_5$, and Q$_6$ are independently selected from the group consisting of hydrogen, hydrocarbyl, substituted hydrocarbyl, hydrocarbylamino, alkoxy, aryloxy, and heterocycle, and $R_2$ and $R_3$ together, $R_1$ and $R_3$ together, or $R_1$ and $R_2$ together can optionally form a ring.

Preferably the transition metal is selected from Periodic Group VIII.

More preferably the combinatorial library is selected from the group consisting of Formulae 1A, 2A, 3A, 4A, 5A, 6A, and 7A

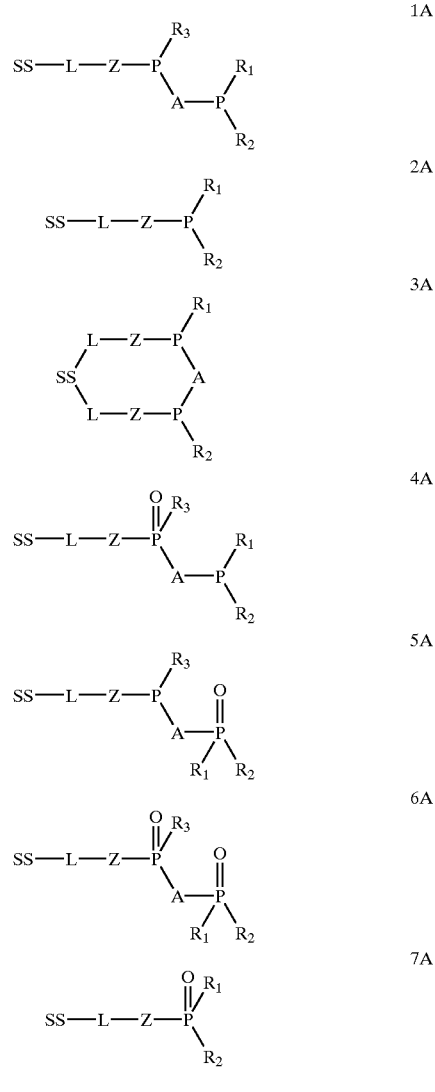

wherein:
Z is a divalent attaching group covalently attached to at least one phosphorus in the phosphine, selected from the group consisting of hydrocarbylene, substituted hydrocarbylene, —O—, —S—, and —$NR_4$—, where $R_4$ is selected from the group consisting of an optionally-substituted hydrocarbyl and halogen; and L is a divalent linking group covalently attached to Z and to SS, selected from the group consisting of optionally-substituted chains of from 1 to 12 linear, branched, and cyclic carbon atoms.

More preferably the combinatorial library of coordination compounds is Formula 1A. In this combinatorial library of coordination compounds the SS is polystyrene; L is —CH—; A is selected from the group consisting of an optionally-substituted carbon chain of 1–3 carbon atoms and an optionally-substituted carbon ring of 6–12 carbon atoms; Z is selected from the group consisting of an optionally-substituted carbon chain of 1–10 carbon atoms, —($NR_4$)—, and —O—; $R_4$ is selected from the group consisting of chloro, cyclohexyl, n-propyl, i-propyl, n-butyl, phenyl, and t-butyl; $R_1$, $R_2$, and $R_3$ are independently selected from the group consisting of hydrogen, Cl, alkyl, alkenyl, aryl, $SQ_1$, $OQ_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle, and where $R_1$ and $R_2$ together with the P form a phosphole, aryl, or alkyl ring; and the transition metal is Rh.

This invention is still further directed to a combinatorial library of coordination compounds comprising one or more transition metals complexed to one or more ligands selected from the group consisting of Formulae 8, 9, 10, 11, and 12

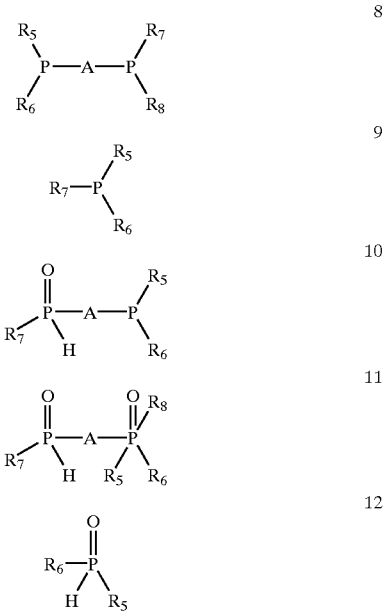

wherein:
A is a divalent group of 1–12 aliphatic or aromatic carbon atoms, linear or branched, optionally containing one or more heteroatoms or organometallic groups; $R_5$, $R_6$, $R_7$, and $R_8$ are independently selected from the group consisting of hydrogen, hydrocarbyl, substituted hydrocarbyl, heterocycle, organometal, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle; and any of the substituents of the group $R_5$, $R_6$, $R_7$, and $R_8$ can optionally together with any other of the substituents of the group $R_5$, $R_6$, $R_7$, and $R_8$ form a ring.

More preferably in the combinatorial library A is an optionally-substituted carbon chain of 1–3 carbon atoms; $R_5$, $R_6$, $R_7$, and $R_8$ are independently selected from the group consisting of hydrogen, Cl, alkyl, alkenyl, aryl, heterocycle, $SQ_1$, $OQ_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy, and heterocycle; and any of $R_5$, $R_6$, $R_7$, and $R_8$ can optionally together with any other of $R_5$, $R_6$, $R_7$, and $R_8$ form a ring; and the transition metals are selected from Periodic Group VIII.

Still more preferably in the combinatorial library the ligands are of Formula 8. Still more preferably in the combinatorial library at least one substituent of the group $R_5$, $R_6$, $R_7$, and $R_8$ differs from the other substituents of the group $R_5$, $R_6$, $R_7$, and $R_8$.

Alternatively, in this combinatorial library of coordination compounds A is an optionally-substituted carbon chain of 1–3 carbon atoms; $R_5$, $R_6$, $R_7$, and $R_8$ are independently selected from the group consisting of hydrogen, Cl, alkyl, alkenyl, aryl, heterocycle, $SQ_1$, $OQ_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy, and heterocycle; and any substituent of the group $R_5$, $R_6$, $R_7$, and $R_8$ can optionally together with any other substituent of the group $R_5$, $R_6$, $R_7$, and $R_8$ form a ring; and the transition metal is Pd.

This invention is still further directed to a process to prepare coumarin comprising contacting salicylaldehyde with an acrylate of the formula

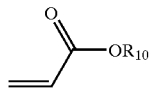

wherein $R_{10}$ is an alkyl group of 1–6 carbons. Preferably, the process to prepare coumarin is performed in the presence of a catalytic amount of a coordination compound comprising one or more transition metals complexed to a ligand selected from the group consisting of Formulae 1, 2, 3, 4, 5, 6, and 7

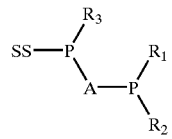

1

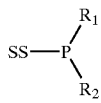

2

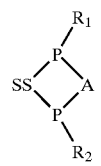

3

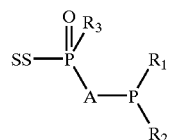

4

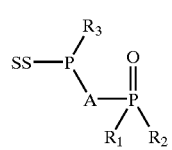

5

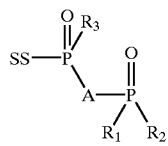

6

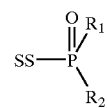

7 wherein:
SS is a solid support wherein at least one P in each phosphine is attached indirectly or directly to the solid support via one or more covalent bonds; A is a divalent group of 1–12 aliphatic or aromatic carbon atoms, linear or branched, optionally containing one or more heteroatoms or organometallic groups; $R_1$, $R_2$ and $R_3$ are independently selected from the group consisting of hydrogen, hydrocarbyl, substituted hydrocarbyl, heterocycle, organometal, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle, and $R_2$ and $R_3$ together, $R_1$ and $R_3$ together, or $R_1$ and $R_2$ together can optionally form a ring.

Preferably, the process for preparing coumarin uses a transition metal selected from Periodic Group VIII.

Preferably in the process to prepare coumarin, the ligand is Formula 1A:

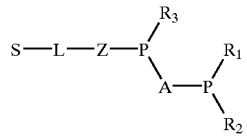

1A wherein:
Z is a divalent attaching group covalently attached to at least one phosphorus in the phosphine, selected from the group consisting of hydrocarbylene, substituted hydrocarbylene, —O—, —S—, and —$NR_4$—, where $R_4$ is selected from the group consisting of an optionally-substituted hydrocarbyl and halogen; and L is a divalent linking group covalently attached to Z and to SS, selected from the group consisting of optionally-substituted chains of from 1 to 12 linear, branched, and cyclic carbon atoms.

More preferably in the process to prepare coumarin, L is —$CH_2$—; A is selected from the group consisting of an optionally-substituted carbon chain of 1–3 carbon atoms and an optionally-substituted carbon ring of 6–12 carbon atoms; Z is selected from the group consisting of an optionally-substituted carbon chain of 1–10 carbon atoms, —($NR_4$)—, and —O—; $R_4$ is selected from the group consisting of chloro, cyclohexyl, n-propyl, i-propyl, n-butyl, phenyl, and t-butyl; $R_1$, $R_2$, and $R_3$ are independently selected from the group consisting of hydrogen, Cl, alkyl, alkenyl, aryl, $SQ_1$, $OQ_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle, and where $R_1$ and $R_2$ together with the P form a phosphole, aryl, or alkyl ring; and the transition metal is Rh.

DETAILED DESCRIPTION OF THE INVENTION

The present invention provides for a process to prepare novel, covalently attached phosphine ligands on polymer supports. These phosphine ligands are useful as catalysts when combined with a transition metal precursor. The present invention also allows synthesis of new free phosphine ligands by chemical cleavage from the solid support.

The invention provides for novel supported phosphine compositions of Formulae 1–7:

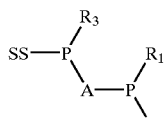

1

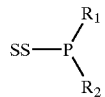

2

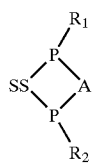

3

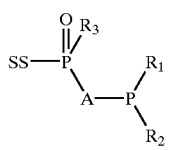

4

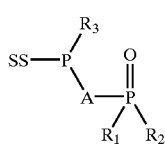

5

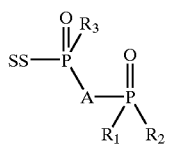

6

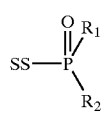

7 wherein SS is a solid support wherein at least one P in each phosphine is attached indirectly or directly to the solid support via one or more covalent bonds;

A is a divalent group of 1–12 aliphatic or aromatic carbon atoms, linear or branched, optionally containing one or more heteroatoms or organometallic groups; $R_1$, $R_2$, and $R_3$ are independently selected from the group consisting of hydrogen, hydrocarbyl, substituted hydrocarbyl, heterocycle, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle, and $R_2$ and $R_3$ together, $R_1$ and $R_3$ together, or $R_1$ and $R_2$ together can optionally form a ring.

By hydrocarbyl is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, cyclopentyl, methylcyclopentyl, cyclohexyl, methylcyclohexyl, benzyl, phenyl, o-tolyl, m-tolyl, p-tolyl, xylyl, vinyl, allyl, butenyl, cyclohexenyl, cyclooctenyl, cyclooctadienyl, and butynyl. Examples of substituted hydrocarbyl groups include methoxy, phenoxy, toluyl, chlorobenzyl, fluoroethyl, p-$CH_3$—S—$C_6H_5$, 2-methoxypropyl, and $(CH_3)_3SiCH_2$.

Virtually any solid material may be used as a support in the context of this invention as long as it meets the following criteria:

The material is insoluble in organic, aqueous, or inorganic solvents. Organic polymer supports are acceptable in this regard but they generally need to be crosslinked. Inorganic support, such as metal oxides ($SiO_2$, $Al_2O_3$, $TiO_2$, $ZrO_2$, etc.), clays, and zeolites, and modified carbons are generally insoluble in these solvents and also may be used as supports.

The support contains reactive sites, which can be used for the covalent attachment of the phosphorus.

The reactive sites are isolated to prevent additional crosslinking during further chemical transformations.

The reactive sites are exposed to the reaction medium. With a polymer resin support this is achieved through the use of a resin which swells in a reaction solvent or is sufficiently porous to allow transport of the reaction medium through the polymer matrix.

The term "solid support" refers to a material having a rigid or semi-rigid surface that contains or can be derivatized to contain functionality, which covalently links a compound to the surface thereof. Other modifications may be made in order to achieve desired physical properties. Such materials are well known in the art and include, by way of example, polystyrene supports, polyacrylamide supports, polyethyleneglycol supports, metal oxides such as silica, and the like. Such supports will preferably take the form of small beads, pellets, disks, films, or other conventional forms, although other forms may be used.

A preferred solid support is an organic or inorganic polymer, to which the phosphorus can be covalently attached through a side chain or pendant group of the polymeric backbone. The polymer may be crosslinked or modified. Suitable preferred polymers useful in the preparation of a supported phosphine compound or a combinatorial library of supported phosphine compounds, include polyolefins, polyacrylates, polymethacrylates, and copolymers thereof that meet the general criteria described above. A more preferred polymeric support is polystyrene wherein the phosphorus is attached to a pendant phenyl group on the polystyrene backbone. Most preferred is polystyrene, crosslinked with divinylbenzene. Specifically, polystyrenes commonly used for solid phase synthesis have been used. These particular resins are crosslinked with from 1 to 10 wt % divinylbenzene. The styrene moieties are substituted in the para or meta positions. Only a portion of the styrene moieties are substituted, typically resulting in functional group loadings of approximately 0.2 to 2.0 mmole per gram of resin, although this value may be higher or lower.

Preferred embodiments for the novel supported phosphine compositions and for combinatorial libraries of supported phosphine compounds are selected from the group of Formulae 1A–7A:

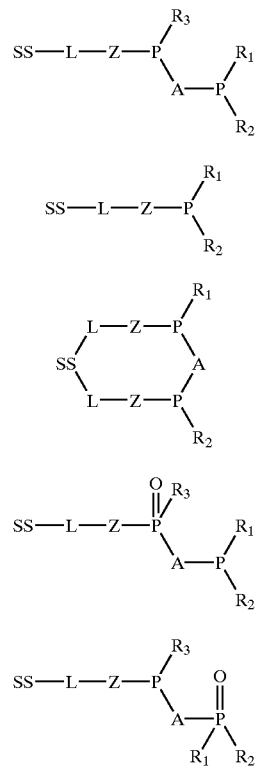

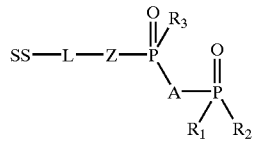

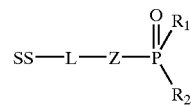

where Z is a divalent attaching group covalently attached to at least one phosphorus in the phosphine, selected from the group consisting of hydrocarbylene, substituted hydrocarbylene, —O—, —S—, and —NR$_4$—, where R$_4$ is selected from the group consisting of an optionally-substituted hydrocarbyl and halogen; and L is a divalent linking group covalently attached to Z and to SS, selected from the group consisting of optionally-substituted chains of from 1 to 12 linear, branched, and cyclic carbon atoms.

Preferred compounds include those where L is —CH$_2$—. Also preferred are those where A is selected from the group consisting of an optionally-substituted carbon chain of 1–3 carbon atoms and an optionally-substituted carbon ring of 6–12 carbon atoms; Z is selected from the group consisting of an optionally-substituted carbon chain of 1–10 carbon atoms, —(NR$_4$)—, and —O—; R$_4$ is selected from the group consisting of chloro, cyclohexyl, n-propyl, i-propyl, n-butyl, phenyl and t-butyl; R$_1$, R$_2$, and R$_3$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$ and Q$_4$ are selected from the group consisting of hydrogen, hydrocarbyl, substituted hydrocarbyl, hydrocarbylamino, and heterocycle, and where R$_1$ and R$_2$ together with the P form a phosphole, aryl, or alkyl ring.

Most preferred compounds are those where the solid support is polystyrene (crosslinked with divinylbenzene) and where L=CH$_2$ and Z, A, R$_1$, R$_2$, and R$_3$ are as shown in Tables 1–5 below.

TABLE 1

Formula 1A

| Z | A | R$_1$ | R$_2$ | R$_3$ |
|---|---|---|---|---|
| N(t-butyl) | (CH$_2$)$_2$ | chloro | chloro | chloro |
| O | (CH$_2$)$_2$ | chloro | chloro | chloro |
| (CH$_2$)$_5$ | (CH$_2$)$_2$ | chloro | chloro | chloro |
| N(t-butyl) | (CH$_2$)$_2$ | 4-methylphenyl | 4-methylphenyl | 4-methylphenyl |
| N(t-butyl) | (CH$_2$)$_2$ | 4-chlorophenyl | 4-chlorophenyl | 4-chlorophenyl |
| N(t-butyl) | (CH$_2$)$_2$ | 4-butylphenyl | 4-butylphenyl | 4-butylphenyl |
| N(t-butyl) | (CH$_2$)$_2$ | ethynyl | ethynyl | ethynyl |
| N(t-butyl) | (CH$_2$)$_2$ | propynyl | propynyl | propynyl |
| N(t-butyl) | (CH$_2$)$_2$ | 4-fluorophenyl | 4-fluorophenyl | 4-fluorophenyl |
| N(t-butyl) | (CH$_2$)$_2$ | vinyl | vinyl | vinyl |
| N(t-butyl) | (CH$_2$)$_2$ | cyclopentyl | cyclopentyl | cyclopentyl |
| N(t-butyl) | (CH$_2$)$_2$ | decyl | decyl | decyl |
| N(t-butyl) | (CH$_2$)$_2$ | 3,4-difluorophenyl | 3,4-difluorophenyl | 3,4-difluorophenyl |
| N(t-butyl) | (CH$_2$)$_2$ | 4-butylphenyl | 4-butylphenyl | 4-butylphenyl |
| N(t-butyl) | (CH$_2$)$_2$ | 3-fluoromethyl-phenyl | 3-fluoromethyl-phenyl | 3-fluoromethyl-phenyl |
| N(t-butyl) | (CH$_2$)$_2$ | 4-methylthiophenyl | 4-methylthiophenyl | 4-methyl-thiophenyl |
| N(t-butyl) | (CH$_2$)$_2$ | 3-methoxyphenyl | 3-methoxyphenyl | 3-methoxy-phenyl |

TABLE 1-continued

Formula 1A

| Z | A | R₁ | R₂ | R₃ |
|---|---|----|----|----|
| N(t-butyl) | (CH$_2$)$_2$ | 3-fluoromethylphenyl | 3-fluoromethylphenyl | 3-fluoromethylphenyl |
| N(t-butyl) | (CH$_2$)$_2$ | 4-methoxyphenyl | 4-methoxyphenyl | 4-methoxyphenyl |
| N(t-butyl) | (CH$_2$)$_2$ | mesityl | mesityl | mesityl |
| N(t-butyl) | (CH$_2$)$_2$ | 2-phenylethyl | 2-phenylethyl | 2-phenylethyl |
| N(t-butyl) | (CH$_2$)$_2$ | 3,4,5-trifluorophenyl | 3,4,5-trifluorophenyl | 3,4,5-trifluorophenyl |
| N(t-butyl) | (CH$_2$)$_2$ | phenethyl | phenethyl | phenethyl |
| N(t-butyl) | (CH$_2$)$_2$ | o-tolyl | o-tolyl | o-tolyl |
| N(t-butyl) | (CH$_2$)$_2$ | 3,5-difluorophenyl | 3,5-difluorophenyl | 3,5-difluorophenyl |
| N(t-butyl) | (CH$_2$)$_2$ | 2-thienyl | 2-thienyl | 2-thienyl |
| N(t-butyl) | (CH$_2$)$_2$ | 2,3,4,5-tetramethylphospholyl | chloro | |
| N(t-butyl) | (CH$_2$)$_2$ | methyl | methyl | chloro |
| N(t-butyl) | (CH$_2$)$_2$ | 2,3,4,5-tetramethylphospholyl | 2,4,6-trimethylphenyl | |
| N(t-butyl) | (CH$_2$)$_2$ | phenoxy | phenoxy | phenoxy |
| (CH$_2$)$_5$ | (CH$_2$)$_2$ | methyl | methyl | methyl |
| (CH$_2$)$_5$ | (CH$_2$)$_2$ | ethyl | ethyl | ethyl |
| (CH$_2$)$_5$ | (CH$_2$)$_2$ | n-propyl | n-propyl | n-propyl |
| (CH$_2$)$_5$ | (CH$_2$)$_2$ | isopropyl | isopropyl | isopropyl |
| (CH$_2$)$_5$ | (CH$_2$)$_2$ | butyl | butyl | butyl |
| (CH$_2$)$_5$ | (CH$_2$)$_2$ | iso-butyl | iso-butyl | iso-butyl |
| (CH$_2$)$_5$ | (CH$_2$)$_2$ | 2-butyl | 2-butyl | 2-butyl |
| (CH$_2$)$_5$ | (CH$_2$)$_2$ | cyclopentyl | cyclopentyl | cyclopentyl |
| (CH$_2$)$_5$ | (CH$_2$)$_2$ | cyclohexyl | cyclohexyl | cyclohexyl |
| (CH$_2$)$_5$ | (CH$_2$)$_2$ | dodecyl | dodecyl | dodecyl |
| (CH$_2$)$_5$ | (CH$_2$)$_2$ | pentadecyl | pentadecyl | pentadecyl |
| (CH$_2$)$_5$ | (CH$_2$)$_2$ | phenyl | phenyl | phenyl |
| (CH$_2$)$_5$ | (CH$_2$)$_2$ | 2-methyl-2-phenylpropyl | 2-methyl-2-phenylpropyl | 2-methyl-2-phenylpropyl |
| (CH$_2$)$_5$ | (CH$_2$)$_2$ | o-tolyl | o-tolyl | o-tolyl |
| (CH$_2$)$_5$ | (CH$_2$)$_2$ | m-tolyl | m-tolyl | m-tolyl |
| (CH$_2$)$_5$ | (CH$_2$)$_2$ | p-tolyl | p-tolyl | p-tolyl |
| (CH$_2$)$_5$ | (CH$_2$)$_2$ | 4-butylphenyl | 4-butylphenyl | 4-butylphenyl |
| (CH$_2$)$_5$ | (CH$_2$)$_2$ | 4-fluorophenyl | 4-fluorophenyl | 4-fluorophenyl |
| (CH$_2$)$_5$ | (CH$_2$)$_2$ | 3-bis(trimethylsilyl)aminophenyl | 3-bis(trimethylsilyl)aminophenyl | 3-bis(trimethylsilyl)aminophenyl |
| (CH$_2$)$_5$ | (CH$_2$)$_2$ | 2,6-dimethylphenyl | 2,6-dimethylphenyl | 2,6-dimethylphenyl |
| (CH$_2$)$_5$ | (CH$_2$)$_2$ | 3,4-difluorophenyl | 3,4-difluorophenyl | 3,4-difluorophenyl |
| (CH$_2$)$_5$ | (CH$_2$)$_2$ | 3-fluoro-methylphenyl | 3-fluoro-methylphenyl | 3-fluoro-methylphenyl |
| (CH$_2$)$_5$ | (CH$_2$)$_2$ | 4-methylthiophenyl | 4-methylthiophenyl | 4-methylthiophenyl |
| (CH$_2$)$_5$ | (CH$_2$)$_2$ | 3-methoxyphenyl | 3-methoxyphenyl | 3-methoxyphenyl |
| (CH$_2$)$_5$ | (CH$_2$)$_2$ | 3-fluoromethylphenyl | 3-fluoromethylphenyl | 3-fluoromethylphenyl |
| (CH$_2$)$_5$ | (CH$_2$)$_2$ | 2-methoxyphenyl | 2-methoxyphenyl | 2-methoxyphenyl |
| (CH$_2$)$_5$ | (CH$_2$)$_2$ | 4-methoxyphenyl | 4-methoxyphenyl | 4-methoxyphenyl |
| (CH$_2$)$_5$ | (CH$_2$)$_2$ | 4-phenoxyphenyl | 4-phenoxyphenyl | 4-phenoxyphenyl |
| (CH$_2$)$_5$ | (CH$_2$)$_2$ | 2,4-difluorophenyl | 2,4-difluorophenyl | 2,4-difluorophenyl |
| (CH$_2$)$_5$ | (CH$_2$)$_2$ | 2-naphthyl | 2-naphthyl | 2-naphthyl |
| (CH$_2$)$_5$ | (CH$_2$)$_2$ | 2-thiophenyl | 2-thiophenyl | 2-thiophenyl |
| (CH$_2$)$_5$ | (CH$_2$)$_2$ | 4-dimethylaminophenyl | 4-dimethylaminophenyl | 4-dimethylaminophenyl |
| N(t-butyl) | C$_6$H$_4$ | chloro | chloro | chloro |
| N(t-butyl) | C$_6$H$_4$ | methylphenyl | 4-methylphenyl | 4-methylphenyl |
| N(t-butyl) | C$_6$H$_4$ | chloro | 3,5-difluorophenyl | 3,5-difluorophenyl |
| (CH$_2$)$_5$ | (CH$_2$)$_2$ | chloro | chloro | cyclohexyl |
| N(t-butyl) | (CH$_2$)$_2$ | phenoxy | phenoxy | cyclohexyl |
| N(t-butyl) | (CH$_2$)$_2$ | n-propyl | n-propyl | n-propyl |
| O | (CH$_2$)$_2$ | chloro | chloro | chloro |
| O | (CH$_2$)$_2$ | i-propyl | i-propyl | i-propyl |
| N(n-propyl) | (CH$_2$)$_2$ | phenyl | phenyl | phenyl |
| N(t-butyl) | (CH$_2$)$_2$ | methyl | phenyl | phenyl |
| N(n-propyl) | (CH$_2$)$_2$ | 2-(diphenylphosphinyl)ethyl | phenyl | phenyl |
| N(n-propyl) | (CH$_2$)$_2$ | 2-(methylphenylphosphinyl)ethyl | phenyl | methyl |
| N(t-butyl) | (CH$_2$)$_2$ | methyl | methyl | 3,5-difluorophenyl |
| N(t-butyl) | (CH$_2$)$_2$ | 3,5-difluorophenyl | 3,5-difluorophenyl | chloro |

TABLE 2

Formula 2A

| Z | $R_1$ | $R_2$ |
|---|---|---|
| N(t-butyl) | chloro | chloro |
| N(t-butyl) | chloro | phenyl |
| N(t-butyl) | vinyl | phenyl |
| N(t-butyl) | phenyl | phenyl |
| N(t-butyl) | mesityl | phenyl |
| N(t-butyl) | ethyl | phenyl |
| N(t-butyl) | allyl | phenyl |
| N(t-butyl) | isopropyl | phenyl |
| N(t-butyl) | vinyl | vinyl |
| N(t-butyl) | mesityl | mesityl |
| N(t-butyl) | isopropyl | isopropyl |
| N(n-propyl) | chloro | chloro |
| N(n-propyl) | chloro | phenyl |
| N(n-propyl) | vinyl | phenyl |
| N(n-propyl) | vinyl | vinyl |
| N(n-propyl) | allyl | phenyl |
| N(n-propyl) | allyl | allyl |
| N(ethyl) | chloro | phenyl |
| N(chloro) | chloro | phenyl |
| N(phenyl) | chloro | phenyl |
| N(i-propyl) | isopropyl | phenyl |
| N(phenyl) | cyclohexyl | cyclohexyl |
| N(n-propyl) | phenyl | 2-methoxyphenyl |
| N(n-propyl) | phenyl | 2,4-dimethoxyphenyl |
| N(t-butyl) | phenyl | 2-methoxyphenyl |
| N(n-propyl) | phenyl | 2-thiomethyphenyl |
| N(n-propyl) | phenyl | 8-(dimethylamino)1-naphthalenyl |
| N(t-butyl) | phenyl | 2-thienyl |
| N(n-propyl) | phenyl | 2-thiazole |
| N(phenyl) | phenyl | 2-diethyl sulfide |
| N(n-propyl) | 2-furyl | 2-thienyl |
| N(n-propyl) | 2-methylthiophenyl | 2-methylthiophenyl |
| N(n-propyl) | 2-methoxyphenyl | 2-methoxyphenyl |
| N(n-propyl) | 8-(dimethylamino)1-naphthalenyl | 8-(dimethylamino)1-naphthalenyl |
| N(phenyl) | ethyl | chloro |
| N(phenyl) | chloro | chloro |
| N(phenyl) | isopropyl | isopropyl |
| N(n-propyl) | phenyl | 2-pyridyl |
| N(n-propyl) | H | phenyl |
| N(n-propyl) | bromo | furyl |
| N(n-propyl) | pyridyl | pyridyl |
| N(n-propyl) | phenyl | 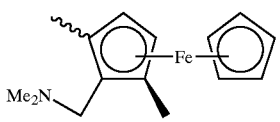 |
| N(phenyl) | ethyl | 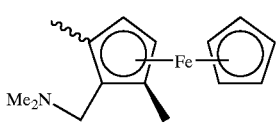 |

TABLE 3

Formula 3A

| Z | A | $R_1$ | $R_2$ |
|---|---|---|---|
| N(n-propyl) | $(CH_2)_2$ | chloro | chloro |
| N(n-propyl) | $(CH_2)_2$ | n-butyl | n-butyl |
| N(n-propyl) | $(CH_2)_2$ | t-butyl | t-butyl |
| N(n-propyl) | $(CH_2)_2$ | | n-heptyl |
| N(n-propyl) | $(CH_2)_2$ | 2-methyl-2-phenylpropyl | 2-methyl-2-phenylpropyl |
| N(n-propyl) | $(CH_2)_2$ | phenyl | phenyl |
| N(n-propyl) | $(CH_2)_2$ | 4-t-butylphenyl | 4-t-butylphenyl |
| N(n-propyl) | $(CH_2)_2$ | mesityl | mesityl |
| N(n-propyl) | $(CH_2)_2$ | 1S, 2S-trans-1,2-cyclohexanediol | |
| N(t-butyl) | $(CH_2)_2$ | chloro | chloro |
| N(t-butyl) | $(CH_2)_2$ | 4-chlorophenyl | 4-chlorophenyl |
| N(t-butyl) | $(CH_2)_2$ | phenethyl | phenethyl |
| N(t-butyl) | $(CH_2)_2$ | i-propyl | i-propyl |
| N(t-butyl) | $(CH_2)_2$ | phenoxy | phenoxy |
| N(cyclohexyl) | $(CH_2)_2$ | chloro | chloro |
| N(cyclohexyl) | $(CH_2)_2$ | | n-heptyl |
| N(n-propyl) | $(CH_2)_2$ | n-heptyl | n-heptyl |

TABLE 4

Formula 4A

| Z | A | $R_1$ | $R_2$ | $R_3$ |
|---|---|---|---|---|
| CH(OH) | $(CH_2)_2$ | i-propyl | i-propyl | i-propyl |

TABLE 5

Formula 5A

| Z | A | $R_1$ | $R_2$ | $R_3$ |
|---|---|---|---|---|
| N(t-butyl) | $(CH_2)_2$ | phenyl | mesityl | phenyl |

Another aspect of this invention is a combinatorial library of supported phosphine compounds selected from the group consisting of Formulae 1, 2, 3, 4, 5, 6, and 7 wherein SS is a solid support wherein at least one P in each phosphine is attached indirectly or directly to the solid support via one or more covalent bonds;

A is a divalent group of 1–12 aliphatic or aromatic carbon atoms, linear or branched, optionally containing one or more heteroatoms or organometallic groups; $R_1$, $R_2$, and $R_3$ are independently selected from the group consisting of hydrogen, hydrocarbyl, substituted hydrocarbyl, heterocycle, organometal, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle, and $R_2$ and $R_3$ together, $R_1$ and $R_3$ together, or $R_1$ and $R_2$ together can optionally form a ring.

As used herein, a combinatorial library is an intentionally created collection of a plurality of differing molecules which can be prepared by selected synthetic means and screened for a desired activity or characteristic in a variety of formats (e.g., libraries of soluble molecules, libraries of compounds attached to resin beads, silica chips, or other solid supports). The libraries are generally prepared such that the compounds are in approximately equimolar quantities, and are prepared by combinatorial synthesis. Combinatorial synthesis refers to the parallel synthesis of diverse compounds by sequential additions of multiple choices of reagents which leads to the generation of large chemical libraries containing related molecules having molecular diversity. Screening methods for libraries vary greatly and are dependent upon a desired activity, the size of library, and the class of compounds in the library.

The libraries of the instant invention can be of any type. These types include but are not limited to arrays and mixtures. Arrays are libraries in which the individual compounds are simultaneously synthesized in spatially segregated locations, typically identified by their location on a grid. Mixture libraries contain a mixture of compounds that are simultaneously synthesized and assayed. Identification of the most active compound is then performed by any of several techniques well known in the combinatorial art, such as deconvolution.

A preferred solid support for the combinatorial libraries of the instant invention is an organic or inorganic polymer as described above, to which the phosphorus can be covalently attached through a side chain or pendant group of the polymeric backbone.

Preferred embodiments for the novel combinatorial libraries of phosphine compositions are shown in Formulae 1A–7A where Z is a divalent attaching group covalently attached to at least one phosphorus in each phosphine, selected from the group consisting of hydrocarbylene, substituted hydrocarbylene, —O—, —S—, and —$NR_4$—, where $R_4$ is selected from the group consisting of an optionally-substituted hydrocarbyl and halogen; and L is a divalent linking group covalently attached to Z and to SS, selected from the group consisting of optionally-substituted chains of from 1 to 12 linear, branched, and cyclic carbon atoms.

Preferred compounds include those where L is —$CH_2$—. Also preferred are those where A is selected from the group consisting of an optionally-substituted carbon chain of 1–3 carbon atoms and an optionally-substituted carbon ring of 6–12 carbon atoms; Z is selected from the group consisting of an optionally-substituted carbon chain of 1–10 carbon atoms, —($NR_4$)—, and —O—; $R_4$ is selected from the group consisting of chloro, cyclohexyl, n-propyl, i-propyl, n-butyl, phenyl and t-butyl; $R_1$, $R_2$, and $R_3$ are independently selected from the group consisting of hydrogen, Cl, alkyl, alkenyl, aryl, $SQ_1$, $OQ_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle, and where $R_1$ and $R_2$ together with the P form a phosphole, aryl, or alkyl ring.

Most preferred libraries are those where the solid support is polystyrene (crosslinked with divinylbenzene) and where L, Z, A, $R_1$, $R_2$, and $R_3$ are as shown in Tables 6–7 below.

TABLE 6

Formula 1A
Mixed libraries $R_1$, $R_2$, $R_3$
L = $CH_2$ Z = N(t-butyl) A = $(CH_2)_2$ n-propyl
3,5-difluorophenyl
n-propyl
cyclopentyl
t-butyl
phenyl
4-t-butylphenyl
2,4,6-trimethylphenyl
4-anisole
3-anisole
2-anisole
4-fluorophenyl
3,4-difluorophenyl
3,5-difluorophenyl
o-tolyl
2-thienyl
3,5-difluorophenyl

TABLE 7

Formula 1A
Array library
L = $CH_2$, Z = $(CH_2)_5$, A = $(CH_2)_2$

| $R_1$ | $R_2$ | $R_3$ |
|---|---|---|
| phenyl | phenyl | phenyl |
| isopropyl | isopropyl | isopropyl |
| butyl | butyl | butyl |
| isobutyl | isobutyl | isobutyl |
| 2-butyl | 2-butyl | 2-butyl |
| cyclopentyl | cyclopentyl | cyclopentyl |
| cyclohexyl | cyclohexyl | cyclohexyl |
| dodecyl | dodecyl | dodecyl |
| pentadecyl | pentadecyl | pentadecyl |
| phenyl | phenyl | phenyl |
| 2-methylphenylpropyl | 2-methylphenylpropyl | 2-methylphenylpropyl |
| o-tolyl | o-tolyl | o-tolyl |
| m-tolyl | m-tolyl | m-tolyl |
| p-tolyl | p-tolyl | p-tolyl |
| 4-butylphenyl | 4-butylphenyl | 4-butylphenyl |
| 4-fluorophenyl | 4-fluorophenyl | 4-fluorophenyl |
| 3-bis(trimethylsilyl)amino-phenyl | 3-bis(trimethylsilyl)amino-phenyl | 3-bis(trimethylsilyl)amino-phenyl |
| 2,6-dimethylphenyl | 2,6-dimethylphenyl | 2,6-dimethylphenyl |
| 3,4-difluorophenyl | 3,4-difluorophenyl | 3,4-difluorophenyl |
| 3-fluoro-methylphenyl | 3-fluoro-methylphenyl | 3-fluoro-methylphenyl |
| 4-methylthiophenyl | 4-methylthiophenyl | 4-methylthiophenyl |
| 3-methoxyphenyl | 3-methoxyphenyl | 3-methoxyphenyl |
| 3-fluoro-methylphenyl | 3-fluoro-methylphenyl | 3-fluoro-methylphenyl |
| 2-methoxyphenyl | 2-methoxyphenyl | 2-methoxyphenyl |
| 4-methoxyphenyl | 4-methoxyphenyl | 4-methoxyphenyl |
| 4-phenoxyphenyl | 4-phenoxyphenyl | 4-phenoxyphenyl |
| 2,4-difluorophenyl | 2,4-difluorophenyl | 2,4-difluorophenyl |
| 2-naphthyl | 2-naphthyl | 2-naphthyl |
| 2-thiophenyl | 2-thiophenyl | 2-thiophenyl |
| 4-dimethylaminophenyl | 4-dimethylaminophenyl | 4-dimethylaminophenyl |

Any reaction in which the phosphorus is covalently attached to the solid support may be used to prepare the compounds and libraries represented by Formula 1–7, such as those described in *Encyclopedia of Inorganic Chemistry*, John Wiley & Sons, Vol. 6, pg. 3149–3213, herein incorporated by reference.

One such scheme, another aspect of this invention, comprises the steps of contacting (i) a phosphine selected from the group consisting of $XPR_1R_2$, $XR_3P$—A—$PR_1R_2$, HP(=O)$R_1R_2$, HP(=O)$R_3$—A—$PR_1R_2$, and HP(=O)$R_3$—A—P(=O)$R_1R_2$ wherein X is a halogen, with (ii) a solid support, resulting in at least one P in the phosphine attached indirectly or directly to the solid support via one or more covalent bonds, and optionally replacing one or more of $R_1$, $R_2$ or $R_3$ with any other $R_1$, $R_2$ or $R_3$ defined above. To create a library, one or more phosphines are reacted with one or more solid supports, generating a plurality of supported phosphine compounds.

One embodiment of attaching the P to the solid support is via the reaction of the halogen or hydrogen bonded to the phosphorus in the phosphine with a nucleophilic group that is covalently attached to a solid support. The term nucleophilic group is a term well recognized in the art and refers to chemical moieties having a reactive pair of electrons. This scheme can easily be adapted for combinatorial synthesis.

When using diphosphines to prepare the compounds of the instant invention, the ratio of the reagents determines whether the product has one P in each phosphine or both P in each phosphine attached covalently to the solid support. When at least 2 molar equivalents of a phosphine of the Formula XR$_3$P—A—PR$_1$R$_2$ is contacted with no more than one molar equivalent of the nucleophilic group attached to the solid support, the resulting product will have one P in the phosphine covalently bonded to the solid support. When no more than one molar equivalent of a phosphine of the Formula XR$_3$P—A—PR$_1$R$_2$ is contacted with at least 2 molar equivalents of the nucleophilic group attached to the solid support, the resulting product will have both P in the phosphine covalently bonded to the solid support.

Other preferred processes of the instant invention to prepare a supported phosphine compound or a library of supported phosphine compounds include where: (1) the supported phosphine compound is of Formula 1A and the process comprises the steps of contacting at least 2 molar equivalents of a phosphine of the Formula XR$_3$P—A—PR$_1$R$_2$ with no more than one molar equivalent of Z, resulting in one P in the phosphine being covalently bonded to the Z; (2) the supported phosphine compound is of Formula 2A and the process comprises the steps of contacting a phosphine of the Formula PR$_1$R$_2$X with the solid support, resulting in one P in the phosphine being covalently bonded to Z; (3) the supported phosphine compound is of Formula 3A and the process comprises the steps of contacting no more than one molar equivalent of a phosphine of the Formula XR$_3$P—A—PR$_1$R$_2$ with at least two molar equivalents of Z, resulting in both of the P in the phosphine being covalently bonded to the Z; (4) the supported phosphine compound is of Formula 4A and the process comprises the steps of contacting a phosphine of the Formula HP(=O)R$_3$—A—PR$_1$R$_2$ with the solid support, resulting in one P in the phosphine being covalently bonded to Z, and (5) where the supported phosphine compound is of Formula 5A and the process comprises the steps of contacting a phosphine of the Formula HP(=O)R$_1$R$_2$ with a solid support of the formula

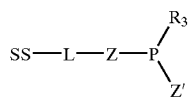

wherein the P in the solid support is covalently bonded to Z and Z' is selected from the group consisting of alkenyls, resulting in the P in the phosphine being covalently bonded to the P in the solid support via Z'.

More preferred is where SS is polystyrene, L is —CH$_2$—, Z is selected from the group consisting of optionally-substituted carbon chain of 1–10 carbon atoms, —(NR$_4$)— and —O—, A is selected from the group consisting of an optionally-substituted carbon chain of 1–3 carbon atoms and an optionally-substituted carbon ring of 6–12 carbon atoms, R$_4$ is selected from the group consisting of chloro, cyclohexyl, n-propyl, i-propyl, n-butyl, phenyl, and t-butyl, and R$_1$, R$_2$, and R$_3$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$, and Q$_4$ are selected from the group consisting of hydrogen, hydrocarbyl, substituted hydrocarbyl, hydrocarbylamino, and heterocycle; and where R$_1$ and R$_2$ together with the P form a phosphole, aryl, or alkyl ring.

Examples of reactions to prepare the compounds are shown but not limited to those in Scheme 1 below, where X is a halogen, M is any metal, R can be one or more of R$_1$, R$_2$, or R$_3$, and R$_1$, R$_2$, R$_3$, R$_4$, Z, and A are as defined above. The Z, O, S, and N substituents are covalently attached to the solid support.

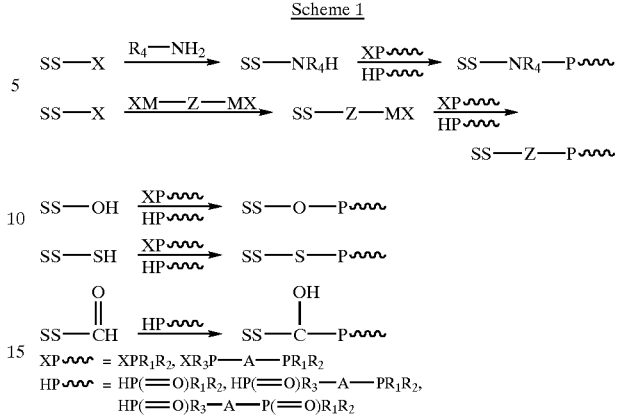

Any of the substituents in the above compounds may be replaced by other functional groups using any procedure known in the art. One or all of the substituents can be reacted in a single reaction, depending on the choice of reactants and reaction conditions. These reactions can easily be adapted for combinatorial processes. Examples of suitable procedures are shown by but not limited to those depicted in Scheme 2 below, where X, M, and A are as defined above, and R indicates any of R$_1$, R$_2$, or R$_3$, as defined above. Examples of suitable definitions for M include Mg, Li, and Zn. Y is any linking group with the proper orientation or with enough flexibility to allow the reaction to proceed. The choice of Y will determine whether the ring is formed between two phosphorus atoms or on one phosphorus atom. Examples of suitable linking groups include hydrocarbylene, substituted hydrocarbylene, and organometallic compounds.

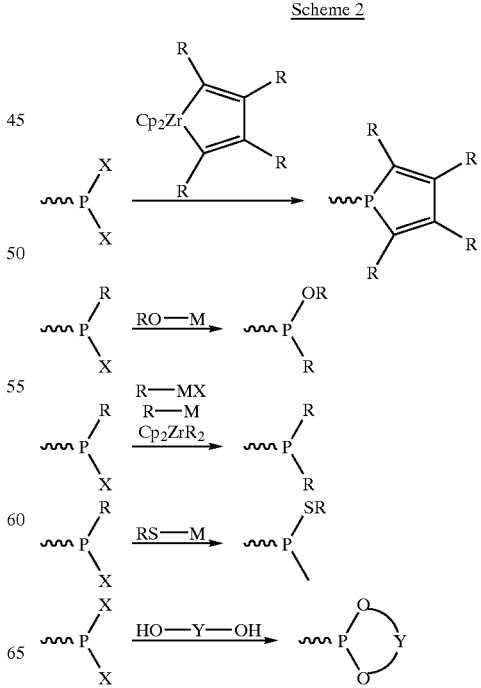

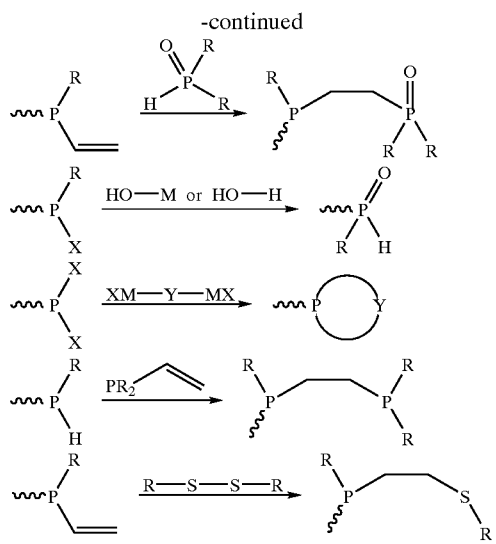

The processes of the instant invention and of Schemes 1–2 are preferably performed under dry, inert atmosphere with dry, deoxygenated solvents. Any solvent is suitable provided that it is inert to all reagents and products. Optimum temperatures are about −80 to about 200° C., preferably about −80 to about 150° C.

The invention provides for novel phosphine compositions of Formulae 8–12:

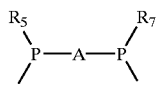

8

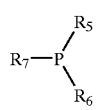

9

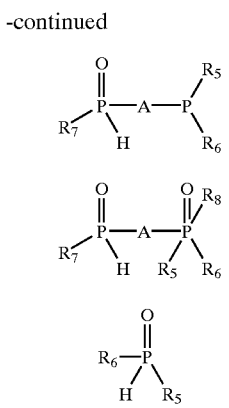

where A is a divalent group of 1–12 aliphatic or aromatic carbon atoms, linear or branched, optionally containing one or more heteroatoms or organometallic groups; $R_5$, $R_6$, $R_7$, and $R_8$ are independently selected from the group consisting of hydrogen, hydrocarbyl, substituted hydrocarbyl, heterocycle, organometal, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle; and any of $R_5$, $R_6$, $R_7$, and $R_8$ can optionally together with any other of $R_5$, $R_6$, $R_7$, and $R_8$ form a ring.

Preferred embodiments for these phosphine compositions are where A is an optionally-substituted carbon chain of 1–3 carbon atoms; $R_5$, $R_6$, $R_7$, and $R_8$ are independently selected from the group consisting of hydrogen, Cl, alkyl, alkenyl, aryl, heterocycle, $SQ_1$, $OQ_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy, and heterocycle; and any of $R_5$, $R_6$, $R_7$, and $R_8$ can optionally together with any other $R_5$, $R_6$, $R_7$, and $R_8$ form a ring. More preferred embodiments for Formula 8 are where at least one of $R_5$, $R_6$, $R_7$, and $R_8$ are different from the rest. Most preferred embodiments are shown in Tables 8–12 below.

TABLE 8

Formula 8
$A = (CH_2)_2$

| $R_5$ | $R_6$ | $R_7$ | $R_8$ |
|---|---|---|---|
| chloro | 3,5-difluorophenyl | 3,5-difluorophenyl | 3,5-difluorophenyl |
| chloro | phenoxy | phenoxy | phenoxy |
| ethoxy | phenyl | phenyl | phenyl |
| ethoxy | ethyl | ethyl | ethyl |
| ethoxy | isobutyl | isobutyl | isobutyl |
| ethoxy | 4-fluorophenyl | 4-fluorophenyl | 4-fluorophenyl |
| methoxy | 4-chlorophenyl | 4-chlorophenyl | 4-chlorophenyl |
| methoxy | mesityl | mesityl | mesityl |
| methoxy | phenethyl | phenethyl | phenethyl |
| 1-propylthio | phenyl | phenyl | phenyl |
| 1-propylthio | isopropyl | isopropyl | isopropyl |
| 1-propylthio | 3,4,5-trifluorophenyl | 3,4,5-trifluorophenyl | 3,4,5-trifluorophenyl |
| diethylamino | isopropyl | isopropyl | isopropyl |
| chloro | o-tolyl | o-tolyl | o-tolyl |
| chloro | 2-thienyl | 2-thienyl | 2-thienyl |
| H | 3,5-difluorophenyl | 3,5-difluorophenyl | 3,5-difluorophenyl |
| phenyl | 3,5-difluorophenyl | 3,5-difluorophenyl | 3,5-difluorophenyl |
| o-tolyl | 3,5-difluorophenyl | 3,5-difluorophenyl | 3,5-difluorophenyl |
| m-tolyl | 3,5-difluorophenyl | 3,5-difluorophenyl | 3,5-difluorophenyl |
| p-tolyl | 3,5-difluorophenyl | 3,5-difluorophenyl | 3,5-difluorophenyl |
| 4-(t-butyl)phenyl | 3,5-difluorophenyl | 3,5-difluorophenyl | 3,5-difluorophenyl |

TABLE 8-continued

Formula 8
A = (CH$_2$)$_2$

| R$_5$ | R$_6$ | R$_7$ | R$_8$ |
|---|---|---|---|
| mesityl | 3,5-difluorophenyl | 3,5-difluorophenyl | 3,5-difluorophenyl |
| 2,5-dimethylphenyl | 3,5-difluorophenyl | 3,5-difluorophenyl | 3,5-difluorophenyl |
| 3-methyl-4-fluoro-phenyl | 3,5-difluorophenyl | 3,5-difluorophenyl | 3,5-difluorophenyl |
| 3,4,5-trifluorophenyl | 3,5-difluorophenyl | 3,5-difluorophenyl | 3,5-difluorophenyl |
| methyl | 3,5-difluorophenyl | 3,5-difluorophenyl | 3,5-difluorophenyl |
| ethyl | 3,5-difluorophenyl | 3,5-difluorophenyl | 3,5-difluorophenyl |
| n-propyl | 3,5-difluorophenyl | 3,5-difluorophenyl | 3,5-difluorophenyl |
| cyclopentyl | 3,5-difluorophenyl | 3,5-difluorophenyl | 3,5-difluorophenyl |
| n-heptyl | 3,5-difluorophenyl | 3,5-difluorophenyl | 3,5-difluorophenyl |
| cyclohexyl | 3,5-difluorophenyl | 3,5-difluorophenyl | 3,5-difluorophenyl |
| phenylmethyl | 3,5-difluorophenyl | 3,5-difluorophenyl | 3,5-difluorophenyl |
| 2-butyl | 3,5-difluorophenyl | 3,5-difluorophenyl | 3,5-difluorophenyl |
| t-butyl | 3,5-difluorophenyl | 3,5-difluorophenyl | 3,5-difluorophenyl |
| n-pentadecyl | 3,5-difluorophenyl | 3,5-difluorophenyl | 3,5-difluorophenyl |
| 3,5-phenyl | 3,5-difluorophenyl | 3,5-difluorophenyl | 3,5-difluorophenyl |
| i-propyl | 3,5-difluorophenyl | 3,5-difluorophenyl | 3,5-difluorophenyl |
| 3-chloro-4-fluoro-phenyl | 3,5-difluorophenyl | 3,5-difluorophenyl | 3,5-difluorophenyl |
| phenethyl | 3,5-difluorophenyl | 3,5-difluorophenyl | 3,5-difluorophenyl |
| i-butyl | 3,5-difluorophenyl | 3,5-difluorophenyl | 3,5-difluorophenyl |
| 2-methyl-2-phenyl-propyl | 3,5-difluorophenyl | 3,5-difluorophenyl | 3,5-difluorophenyl |
| n-decyl | 3,5-difluorophenyl | 3,5-difluorophenyl | 3,5-difluorophenyl |
| 3,4-dimethoxyphenyl | 3,5-difluorophenyl | 3,5-difluorophenyl | 3,5-difluorophenyl |
| 2-methoxy-4-fluoro-phenyl | 3,5-difluorophenyl | 3,5-difluorophenyl | 3,5-difluorophenyl |
| 2-methoxy | 3,5-difluorophenyl | 3,5-difluorophenyl | 3,5-difluorophenyl |
| 4-phenoxyphenyl | 3,5-difluorophenyl | 3,5-difluorophenyl | 3,5-difluorophenyl |
| allyl | 3,5-difluorophenyl | 3,5-difluorophenyl | 3,5-difluorophenyl |
| thiophenyl | 3,5-difluorophenyl | 3,5-difluorophenyl | 3,5-difluorophenyl |
| phenoxy | 3,5-difluorophenyl | 3,5-difluorophenyl | 3,5-difluorophenyl |
| H | o-tolyl | o-tolyl | o-tolyl |
| phenyl | o-tolyl | o-tolyl | o-tolyl |
| o-tolyl | o-tolyl | o-tolyl | o-tolyl |
| m-tolyl | o-tolyl | o-tolyl | o-tolyl |
| p-tolyl | o-tolyl | o-tolyl | o-tolyl |
| 4-(t-butyl)phenyl | o-tolyl | o-tolyl | o-tolyl |
| mesityl | o-tolyl | o-tolyl | o-tolyl |
| 2,5-dimethylphenyl | o-tolyl | o-tolyl | o-tolyl |
| 3-methyl-4-fluoro-phenyl | o-tolyl | o-tolyl | o-tolyl |
| 3,4,5-trifluorophenyl | o-tolyl | o-tolyl | o-tolyl |
| methyl | o-tolyl | o-tolyl | o-tolyl |
| ethyl | o-tolyl | o-tolyl | o-tolyl |
| n-propyl | o-tolyl | o-tolyl | o-tolyl |
| cyclopentyl | o-tolyl | o-tolyl | o-tolyl |
| n-heptyl | o-tolyl | o-tolyl | o-tolyl |
| cyclohexyl | o-tolyl | o-tolyl | o-tolyl |
| phenylmethyl | o-tolyl | o-tolyl | o-tolyl |
| 2-butyl | o-tolyl | o-tolyl | o-tolyl |
| t-butyl | o-tolyl | o-tolyl | o-tolyl |
| n-pentadecyl | o-tolyl | o-tolyl | o-tolyl |
| 3,5-phenyl | o-tolyl | o-tolyl | o-tolyl |
| i-propyl | o-tolyl | o-tolyl | o-tolyl |
| 3-chloro-4-fluoro-phenyl | o-tolyl | o-tolyl | o-tolyl |
| phenethyl | o-tolyl | o-tolyl | o-tolyl |
| i-butyl | o-tolyl | o-tolyl | o-tolyl |
| 2-methyl-2-phenyl-propyl | o-tolyl | o-tolyl | o-tolyl |
| n-decyl | o-tolyl | o-tolyl | o-tolyl |
| 3,4-dimethoxyphenyl | o-tolyl | o-tolyl | o-tolyl |
| 2-methoxy-4-fluoro-phenyl | o-tolyl | o-tolyl | o-tolyl |
| 2-methoxy | o-tolyl | o-tolyl | o-tolyl |
| 4-phenoxyphenyl | o-tolyl | o-tolyl | o-tolyl |
| allyl | o-tolyl | o-tolyl | o-tolyl |
| thiophenyl | o-tolyl | o-tolyl | o-tolyl |
| phenoxy | o-tolyl | o-tolyl | o-tolyl |
| H | 2-thienyl | 2-thienyl | 2-thienyl |
| phenyl | 2-thienyl | 2-thienyl | 2-thienyl |
| o-tolyl | 2-thienyl | 2-thienyl | 2-thienyl |
| m-tolyl | 2-thienyl | 2-thienyl | 2-thienyl |

TABLE 8-continued

Formula 8
A = (CH$_2$)$_2$

| R$_5$ | R$_6$ | R$_7$ | R$_8$ |
|---|---|---|---|
| p-tolyl | 2-thienyl | 2-thienyl | 2-thienyl |
| 4-(t-butyl)phenyl | 2-thienyl | 2-thienyl | 2-thienyl |
| mesityl | 2-thienyl | 2-thienyl | 2-thienyl |
| 2,5-dimethylphenyl | 2-thienyl | 2-thienyl | 2-thienyl |
| 3-methyl-4-fluoro-phenyl | 2-thienyl | 2-thienyl | 2-thienyl |
| 3,4,5-trifluorophenyl | 2-thienyl | 2-thienyl | 2-thienyl |
| methyl | 2-thienyl | 2-thienyl | 2-thienyl |
| ethyl | 2-thienyl | 2-thienyl | 2-thienyl |
| n-propyl | 2-thienyl | 2-thienyl | 2-thienyl |
| cyclopentyl | 2-thienyl | 2-thienyl | 2-thienyl |
| n-heptyl | 2-thienyl | 2-thienyl | 2-thienyl |
| cyclohexyl | 2-thienyl | 2-thienyl | 2-thienyl |
| phenylmethyl | 2-thienyl | 2-thienyl | 2-thienyl |
| 2-butyl | 2-thienyl | 2-thienyl | 2-thienyl |
| t-butyl | 2-thienyl | 2-thienyl | 2-thienyl |
| n-pentadecyl | 2-thienyl | 2-thienyl | 2-thienyl |
| 3,5-phenyl | 2-thienyl | 2-thienyl | 2-thienyl |
| i-propyl | 2-thienyl | 2-thienyl | 2-thienyl |
| 3-chloro-4-fluoro-phenyl | 2-thienyl | 2-thienyl | 2-thienyl |
| phenethyl | 2-thienyl | 2-thienyl | 2-thienyl |
| i-butyl | 2-thienyl | 2-thienyl | 2-thienyl |
| 2-methyl-2-phenyl-propyl | 2-thienyl | 2-thienyl | 2-thienyl |
| n-decyl | 2-thienyl | 2-thienyl | 2-thienyl |
| 3,4-dimethoxyphenyl | 2-thienyl | 2-thienyl | 2-thienyl |
| 2-methoxy-4-fluoro-phenyl | 2-thienyl | 2-thienyl | 2-thienyl |
| 2-methoxy | 2-thienyl | 2-thienyl | 2-thienyl |
| 4-phenoxyphenyl | 2-thienyl | 2-thienyl | 2-thienyl |
| allyl | 2-thienyl | 2-thienyl | 2-thienyl |
| thiophenyl | 2-thienyl | 2-thienyl | 2-thienyl |
| phenoxy | 2-thienyl | 2-thienyl | 2-thienyl |
| chloro | phenyl | chloro | phenyl |
| phenyl | chloro | chloro | phenyl |
| chloro | H | chloro | H |
| H | chloro | chloro | H |
| chloro | mesityl | chloro | mesityl |
| mesityl | chloro | chloro | mesityl |
| methoxy | 4-chlorophenyl | methoxy | 4-chlorophenyl |
| 4-chlorophenyl | methoxy | methoxy | 4-chlorophenyl |
| n-heptyl | methoxy | n-heptyl | methoxy |
| methoxy | n-heptyl | n-heptyl | methoxy |
| chloro | chloro | 1S,2S-trans-1,2-cyclohexanediol | |
| chloro | chloro | n-heptyl | |
| phenyl | phenoxy | phenyl | phenoxy |
| phenoxy | phenyl | phenyl | phenoxy |
| 2-methyl-2-phenyl-propyl | 3,5-difluorophenoxy | 2-methyl-2-phenyl-propyl | 3,5-difluorophenoxy |
| 3,5-difluorophenoxy | 2-methyl-2-phenyl-propyl | 2-methyl-2-phenyl-propyl | 3,5-difluorophenoxy |
| thiopropyl | phenyl | thiopropyl | phenyl |
| thiopropyl | phenyl | phenyl | thiopropyl |
| diethylamino | chloro | chloro | chloro |
| chloro | phenyl | phenyl | phenyl |
| ethoxy | n-propyl | n-propyl | n-propyl |
| ethoxy | 3,5-difluorophenyl | 3,5-difluorophenyl | 3,5-difluorophenyl |
| ethoxy | n-propyl | 3,5-difluorophenyl | 3,5-difluorophenyl |
| ethoxy | n-propyl | n-propyl | 3,5-difluorophenyl |
| ethoxy | 3,5-difluorophenyl | n-propyl | n-propyl |
| ethoxy | 3,5-difluorophenyl | n-propyl | 3,5-difluorophenyl |

TABLE 8-continued

Formula 8
A = (CH₂)₂

| R₅ | R₆ | R₇ | R₈ |
|---|---|---|---|
| 3,5-difluorophenyl | 3,5-difluorophenyl | | |

(structure: binaphthyl bis-O linked)

TABLE 9

Formula 9

| R₇ | R₅ | R₆ |
|---|---|---|
| chloro | phenyl | phenyl |
| thiopropyl | phenyl | phenyl |
| ethoxy | i-propyl | i-propyl |
| i-propyl | i-propyl | i-propyl |
| thiopropyl | mesityl | mesityl |
| thiopropyl | phenyl | i-propyl |
| chloro | cyclohexyl | cyclohexyl |
| chloro | vinyl | phenyl |
| chloro | phenyl | 2-methoxyphenyl |
| chloro | phenyl | 2,4-dimethoxyphenyl |
| chloro | phenyl | 2-methoxyphenyl |
| chloro | phenyl | 2-thiomethyphenyl |
| chloro | phenyl | 2-thienyl |
| chloro | phenyl | 2-thiazole |
| chloro | phenyl | 2-diethyl sulfide |
| chloro | 2-methylthiophenyl | 2-methylthiophenyl |
| chloro | 2-methoxyphenyl | 2-methoxyphenyl |

TABLE 10

Formula 10
A = (CH₂)₂

| R₇ | R₅ | R₆ |
|---|---|---|
| methyl | methyl | methyl |
| ethyl | ethyl | ethyl |
| n-propyl | n-propyl | n-propyl |
| i-propyl | i-propyl | i-propyl |
| phenyl | phenyl | phenyl |
| 3,5-difluorophenyl | 3,5-difluorophenyl | 3,5-difluorophenyl |
| mesityl | mesityl | mesityl |
| phenyl | phenyl | methyl |
| 2-(diphenylphosphinyl)ethyl | phenyl | phenyl |
| 2-(methylphenylphosphinyl)ethyl | phenyl | methyl |

TABLE 11

Formula 11
A = (CH₂)₂

| R₆ | R₇ | R₈ |
|---|---|---|
| phenyl | phenyl | H |
| | heptyl | H |

TABLE 11-continued

Formula 11
A = (CH₂)₂

| R₆ | R₇ | R₈ |
|---|---|---|
| phenyl | phenyl | mesityl |
| phenethyl | phenethyl | H |

TABLE 12

Formula 12

| R₆ | R₅ |
|---|---|
| i-propyl | i-propyl |
| mesityl | phenyl |
| i-propyl | phenyl |
| 2-thienyl | 2-furyl |
| 8-(dimethylamino)1-naphthalenyl | 8-(dimethylamino)1-naphthalenyl |
| phenyl | 8-(dimethylamino)1-naphthalenyl |
| phenyl | 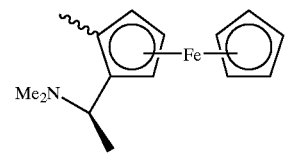 |
| phenyl | 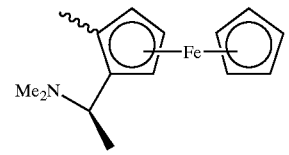 |

The invention also provides for combinatorial libraries of the phosphine compositions of Formulae 8–12 where A is a divalent group of 1–12 aliphatic or aromatic carbon atoms, linear or branched, optionally containing one or more heteroatoms or organometallic groups; $R_5$, $R_6$, $R_7$, and $R_8$ are independently selected from the group consisting of hydrogen, hydrocarbyl, substituted hydrocarbyl, heterocycle, organometal, Cl, Br, I, $SQ_1$, $OQ_2$, $PQ_3Q_4$ and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle; and any of $R_5$, $R_6$, $R_7$, and $R_8$ can optionally together with any other of $R_5$, $R_6$, $R_7$, and $R_8$ form a ring. The libraries can be including arrays and any type of mixtures.

Preferred embodiments for these libraries are where A is an optionally-substituted carbon chain of 1–3 carbon atoms; $R_5$, $R_6$, $R_7$, and $R_8$ are independently selected from the group consisting of hydrogen, Cl, alkyl, alkenyl, aryl, heterocycle, $SQ_1$, $OQ_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy, and heterocycle; and any of $R_5$, $R_6$, $R_7$, and $R_8$ can optionally together with any other of $R_5$, $R_6$, $R_7$, and $R_8$ form a ring. More preferred embodiments for Formula 8 are where at least one of $R_5$, $R_6$, $R_7$, and $R_8$ are different from the rest. Most preferred embodiments are shown in Tables 13–14 below.

TABLE 13

Formula 8
Array library
A = $(CH_2)_2$

| $R_5$ | $R_6$ | $R_7$ |
|---|---|---|
| o-tolyl | o-tolyl | o-tolyl |
| 2-thienyl | 2-thienyl | 2-thienyl |
| 3,5-difluorophenyl | 3,5-difluorophenyl | 3,5-difluorophenyl |

| $R_8$ |
|---|
| H |
| phenyl |
| o-tolyl |
| m-tolyl |
| p-tolyl |
| 4-(t-butyl)phenyl |
| mesityl |
| 2,5-dimethylphenyl |
| 3-methyl-4-fluorophenyl |
| 3,4,5-trifluorophenyl |
| methyl |
| ethyl |
| n-propyl |
| cyclopentyl |
| n-heptyl |
| cyclohexyl |
| phenylmethyl |
| 2-butyl |
| t-butyl |
| n-pentadecyl |
| 3,5-phenyl |
| i-propyl |
| 3-chloro-4-fluorophenyl |
| phenethyl |
| i-butyl |
| 2-methyl-2-phenylpropyl |
| n-decyl |
| 3,4-dimethoxyphenyl |
| 2-methoxy-4-fluorophenyl |
| 2-methoxy |
| 4-phenoxyphenyl |
| allyl |
| thiophenyl |
| phenoxy |

TABLE 14

Formula 8
Mixed library
A = $(CH_2)_2$

| $R_5$ |
|---|
| ethoxy |

| $R_6$, $R_7$, $R_8$ |
|---|
| n-propyl |
| 3,5-difluorophenyl |

Another aspect of this invention is a process to prepare the phosphine compound of Formulae 8–12 or a combinatorial library of phosphine compounds of Formulae 8–12 where A is a divalent group of 1–12 aliphatic or aromatic carbon atoms, linear or branched, optionally containing one or more heteroatoms or organometallic groups; $R_5$, $R_6$, $R_7$, and $R_8$ are independently selected from the group consisting of hydrogen, hydrocarbyl, substituted hydrocarbyl, heterocycle, organometal, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle; and any of $R_5$, $R_6$, $R_7$, and $R_8$ can optionally together with any other of $R_5$, $R_6$, $R_7$, and $R_8$ form a ring. The process comprises the steps of:

(a) contacting (i) a supported phosphine selected from the group consisting of Formulae 1, 2, 3, 4, 5, 6, and 7 where SS is a solid support wherein at least one P in the phosphine is attached indirectly or directly to the solid support via one or more covalent bonds; A is a divalent group of 1–12 aliphatic or aromatic carbon atoms, linear or branched, optionally containing one or more heteroatoms or organometallic groups; $R_1$, $R_2$, and $R_3$ are independently selected from the group consisting of hydrogen, hydrocarbyl, substituted hydrocarbyl, heterocycle, organometal, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle, and $R_2$ and $R_3$ together, $R_1$ and $R_3$ together, or $R_1$ and $R_2$ together can optionally form a ring; with (ii) a compound of the Formula $ER_9$, wherein E is an electrophilic group and $R_9$ is selected from the group consisting of hydrogen, hydrocarbyl, substituted hydrocarbyl, heterocycle, organometal, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle; thereby forming the corresponding compound of Formulae 1, 2, 3, 4, 5, 6, and 7; and (b) optionally replacing one or more of $R_5$, $R_6$, $R_7$, and $R_8$ with any $R_5$, $R_6$, $R_7$, and $R_8$.

To create a library, one or more supported phosphines are reacted with one or more compounds of the Formula $ER_9$, generating a plurality of phosphine compounds.

A preferred process is where the phosphine or the library of phosphines produced by the above process is substituted asymmetrically; such compounds are difficult to prepare by techniques previously known in the art. The solid support serves essentially as a protecting group, facilitating the attachment of at least one substituent on a phosphorus that is different than the others. The process operates without any complicated separation or purification steps needed.

When the bisphosphine compounds of the present invention are unsymmetrically substituted, whether they are supported or unsupported, two isomers are present, cis and trans, as illustrated below.

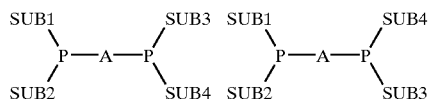

The processes described herein prepare a 50/50 mixture of these two isomers. The isomers can be isolated by standard techniques such as recrystallization.

In the above process, E is any electrophilic group that will cleave the covalent bond attaching the phosphorus to the solid support. The term electrophilic group is a term well recognized in the art and refers to chemical moieties, which can accept a pair of electrons from a nucleophilic group as defined above. Suitable electrophilic groups include —OH, trimethylsilyl, $PCl_2$, halogens, and protons donated from compounds such as acids, alcohols, or amines.

In the instance where $ER_5$ is water, the resulting POH group would rearrange to yield to form the compounds of Formula 10, 11, or 12. These compounds can also be formed from any other of Formulae 8–12 via the replacement of one or more of $R_5$, $R_6$, $R_7$, and $R_8$ with an —OH group using any method known in the art. An equivalent rearrangement occurs when a PSH group is present.

Preferred processes for the preparation of the phosphine compounds or the library of phosphine compounds of the instant invention include those wherein the supported phosphine is selected from the group consisting of Formulae 1A, 2A, 3A, 4A, 5A, 6A, and 7A where Z is a divalent attaching group covalently attached to at least one phosphorus in the phosphine, selected from the group consisting of hydrocarbylene, substituted hydrocarbylene, —O—, —S—, and —$NR_4$—, where $R_4$ is selected from the group consisting of an optionally-substituted hydrocarbyl and halogen; and L is a divalent linking group covalently attached to Z and to SS, selected from the group consisting of optionally-substituted chains of from 1 to 12 linear, branched, and cyclic carbon atoms; A is an optionally-substituted carbon chain of 1–3 carbon atoms; $R_5$, $R_6$, $R_7$, and $R_8$ are independently selected from the group consisting of hydrogen, Cl, alkyl, alkenyl, aryl, heterocycle, $SQ_1$, $OQ_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy, and heterocycle; and any of $R_5$, $R_6$, $R_7$, and $R_8$ can optionally together with any other of $R_5$, $R_6$, $R_7$, and $R_8$ form a ring.

Also preferred is where E is selected from the group consisting of hydrogen, $PCl_2$, and $SiMe_3$, and where $R_5$ is a halogen.

After cleavage from the solid support, $R_5$, $R_6$, $R_7$, and $R_8$ may be replaced with any other substituent using any method known in the art, in order to prepare a further range of compounds.

The process is preferably performed under dry, inert atmosphere with dry, deoxygenated solvents. Any solvent is suitable provided that it is inert to all reagents and products. Optimum temperatures are about −80 to about 200° C., preferably about −80 to about 150° C.

Preferred versions of the process to prepare the phosphine compounds or the library of phosphine compounds of the instant invention include those where the supported phosphine compound is selected from the group consisting of Formulae 1 and 3 and the corresponding phosphine compound is of Formula 8, the supported phosphine compound is of Formula 2 and the corresponding phosphine compound is of Formula 9; the supported phosphine compound is of Formula 4 and the phosphine compound is of Formula 10, the supported phosphine compound is selected from the group consisting of Formulae 3 and 5 and the phosphine compound is of Formula 11, and the supported phosphine compound is of Formula 2, and the phosphine compound is of Formula 12. More preferred is where Z is selected from the group consisting of optionally-substituted carbon chain of 1–10 carbon atoms, —($NR_4$)—, and —O—, A is selected from the group consisting of an optionally-substituted carbon chain of 1–3 carbon atoms and an optionally-substituted carbon ring of 6–12 carbon atoms, $R_5$, $R_6$, $R_7$, and $R_8$ are independently selected from the group consisting of hydrogen, Cl, alkyl, alkenyl, aryl, heterocycle, $SQ_1$, $OQ_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy, and heterocycle, and any of $R_5$, $R_6$, $R_7$, and $R_8$ can optionally together with any other of $R_5$, $R_6$, $R_7$, and $R_8$ form a ring.

The phosphorus compounds and libraries described herein, both supported and unsupported, can be utilized as ligands for catalytic compounds.

Another aspect of the instant invention is a coordination compound comprising one or more transition metals complexed to a ligand selected from the group consisting of Formulae 1, 2, 3, 4, 5, 6, and 7 where SS is a solid support wherein at least one P in each phosphine is attached indirectly or directly to the solid support via one or more covalent bonds, A is a divalent group of 1–12 aliphatic or aromatic carbon atoms, linear or branched, optionally containing one or more heteroatoms or organometallic groups, $R_1$, $R_2$, and $R_3$ are independently selected from the group consisting of hydrogen, hydrocarbyl, substituted hydrocarbyl, heterocycle, organometal, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle, and $R_2$ and $R_3$ together, $R_1$ and $R_3$ together, or $R_1$ and $R_2$ together can optionally form a ring.

"Coordination compound" refers to a compound formed by the union of a metal ion (usually a transition metal) with a non-metallic ion or molecule called a ligand or complexing agent.

The transition metals are hereby defined as metals of atomic weight 21 through 83. Preferably, the transition metal is from Periodic Group VIII, hereby defined as Fe, Co, Ni, Ru, Rh, Pd, Os, Ir, and Pt. Preferred is Rh. The complex can be made by any synthetic method known in the art, either through direct reaction or via the use of a transition metal precursor. Many of these techniques are described in Hartley, ibid.

A preferred embodiment for the coordination compound is where SS is selected from the group consisting of polyolefins, polyacrylates, polymethacrylates, and copolymers thereof, and wherein the transition metals are selected from Periodic Group VIII.

Another preferred embodiment of the coordination compound is where the ligand is selected from the group consisting of Formulae 1A, 2A, 3A, 4A, 5A, 6A, and 7A where Z is a divalent attaching group covalently attached to at least one phosphorus in the phosphine, selected from the group consisting of hydrocarbylene, substituted hydrocarbylene, —O—, —S—, and —$NR_4$— where $R_4$ is selected from the group consisting of an optionally-substituted hydrocarbyl and halogen, and L is a divalent linking group covalently attached to Z and to SS, selected from the group consisting of optionally-substituted chains of from 1 to 12 linear, branched, and cyclic carbon atoms.

More preferred is where the ligand is Formula 1A where SS is polystyrene, L is —$CH_2$—, A is selected from the group consisting of an optionally-substituted carbon chain of 1–3 carbon atoms and an optionally-substituted carbon ring of 6–12 carbon atoms, Z is selected from the group consisting of an optionally-substituted carbon chain of 1–10 carbon atoms, —($NR_4$)—, and —O—, $R_4$ is selected from the group consisting of chloro, cyclohexyl, n-propyl, i-propyl, n-butyl, phenyl and t-butyl, $R_1$, $R_2$, and $R_3$ are independently selected from the group consisting of hydrogen, Cl, alkyl, alkenyl, aryl, $SQ_1$, $OQ_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle, and where $R_1$ and $R_2$ together with the P form a phosphole, aryl or alkyl ring, and the transition metal is Rh. Most preferred is where the ligand is polymer-bound 1-(1,1-di-n-propylphosphino)-2-n-propyl phospinioethane.

Most preferred is where the ligand is Formula 1A, L is $(CH_2)$, Z is N(t-butyl), A is $(CH_2)_2$, R is n-propyl, $R_2$ is n-propyl, $R_3$ is n-propyl, and M is Rh.

Another aspect of the invention is a combinatorial library of coordination compounds comprising one or more transition metals complexed to one or more ligands selected from the group consisting of Formulae 1, 2, 3, 4, 5, 6, and 7 where SS is a solid support wherein at least one P in each phosphine is attached indirectly or directly to the solid support via one or more covalent bonds, A is a divalent group of 1–12 aliphatic or aromatic carbon atoms, linear or branched, optionally containing one or more heteroatoms or organometallic groups, $R_1$, $R_2$, and $R_3$ are independently selected from the group consisting of hydrogen, hydrocarbyl, substituted hydrocarbyl, heterocycle, organometal, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle, and $R_2$ and $R_3$ together, $R_1$ and $R_3$ together, or $R_1$ and $R_2$ together can optionally form a ring.

A preferred embodiment is where SS is selected from the group consisting of polyolefins, polyacrylates, polymethacrylates, and copolymers thereof, and wherein the transition metals are selected from Periodic Group VIII.

Also preferred is where the ligand is selected from the group consisting of Formulae 1A, 2A, 3A, 4A, 5A, 6A, and 7A where Z is a divalent attaching group covalently attached to at least one phosphorus in the phosphine, selected from the group consisting of hydrocarbylene, substituted hydrocarbylene, —O—, —S—, and —NR$_4$—, where R$_4$ is selected from the group consisting of an optionally-substituted hydrocarbyl and halogen, and L is a divalent linking group covalently attached to Z and to SS, selected from the group consisting of optionally-substituted chains of from 1 to 12 linear, branched, and cyclic carbon atoms.

More preferred is where the ligand is Formula 1A, SS is polystyrene, L is —CH$_2$—, A is selected from the group consisting of an optionally-substituted carbon chain of 1–3 carbon atoms and an optionally-substituted carbon ring of 6–12 carbon atoms, Z is selected from the group consisting of an optionally-substituted carbon chain of 1–10 carbon atoms, —(NR$_4$)—, and —O—, R$_4$ is selected from the group consisting of chloro, cyclohexyl, n-propyl, i-propyl, n-butyl, phenyl, and t-butyl, $R_1$, $R_2$, and $R_3$ are independently selected from the group consisting of hydrogen, Cl, alkyl, alkenyl, aryl, $SQ_1$, $OQ_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle, and where $R_1$ and $R_2$ together with the P form a phosphole, aryl, or alkyl ring, and the transition metal is Rh.

Another aspect of the instant invention are novel combinatorial libraries of coordination compounds comprising one or more transition metals complexed to one or more ligands selected from the group consisting of Formulae 8, 9, 10, 11, and 12 where A is a divalent group of 1–12 aliphatic or aromatic carbon atoms, linear or branched, optionally containing one or more heteroatoms or organometallic groups, $R_5$, $R_6$, $R_7$, and $R_8$ are independently selected from the group consisting of hydrogen, hydrocarbyl, substituted hydrocarbyl, heterocycle, organometal, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle, and any of $R_5$, $R_6$, $R_7$, and $R_8$ can optionally together with any other of $R_5$, $R_6$, $R_7$, and $R_8$ form a ring.

Preferred is the combinatorial library where A is an optionally-substituted carbon chain of 1–3 carbon atoms, $R_5$, $R_6$, $R_7$, and $R_8$ are independently selected from the group consisting of hydrogen, Cl, alkyl, alkenyl, aryl, heterocycle, $SQ_1$, $OQ_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy, and heterocycle, and any of $R_5$, $R_6$, $R_7$, and $R_8$ can optionally together with any other of $R_5$, $R_6$, $R_7$, and $R_8$ form a ring, and the transition metals are selected from Periodic Group VIII.

Also preferred is where the ligands are of Formula 8, and where at least one of $R_5$, $R_6$, $R_7$, and $R_8$ are different from the rest.

More preferred is where A is an optionally-substituted carbon chain of 1–3 carbon atoms, $R_5$, $R_6$, $R_7$, and $R_8$ are independently selected from the group consisting of hydrogen, Cl, alkyl, alkenyl, aryl, heterocycle, $SQ_1$, $OQ_2$, and $PQ_3Q_4$, where $Q_1$, $Q_2$, $Q_3$, and $Q_4$ are independently selected from the group consisting of hydrogen, hydrocarbyl, substituted hydrocarbyl, hydrocarbylamino, alkoxy, aryloxy, and heterocycle, and any of $R_5$, $R_6$, $R_7$, and $R_8$ can optionally together with any other of $R_5$, $R_6$, $R_7$, and $R_8$ form a ring, and the transition metal is Pd.

Most preferred is where the ligand is of Formula 8, A=$(CH_2)_2$, and where $R_5$, $R_6$, $R_7$, $R_8$, and M are shown below:

| $R_5$ | $R_6$ | $R_7$ | $R_8$ | M |
|---|---|---|---|---|
| thiopropyl | phenyl | thiopropyl | phenyl | Pd |
| thiopropyl | phenyl | phenyl | thiopropyl | Pd |

The phosphine coordination compounds and libraries of phosphine coordination compounds can be prepared by any method known in the art, but preferably by those described herein.

Another aspect of the instant invention is a novel reaction to prepare coumarin, useful as an intermediate in pharmaceutical preparations, by contacting salicylaldehyde with an acrylate of the formula

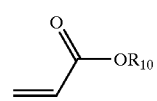

Formula 13 wherein $R_{10}$ is an alkyl group of 1–6 carbons. Preferred is where $R_{10}$ is n-butyl. Salicylaldehyde is converted via decarbonylation and insertion of an acrylate, followed by ring closure, as shown in Scheme 3.

Scheme 3

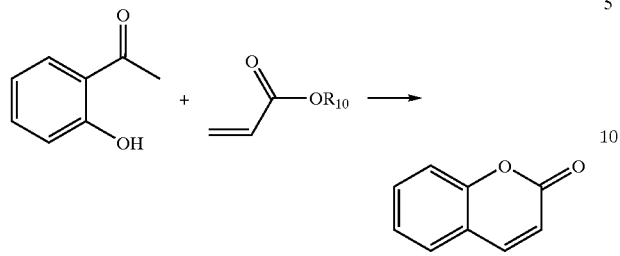

A preferred process is where the reaction is performed in the presence of a catalytic amount of the novel, phosphine coordination compounds of the instant invention, described above. Preferred is where the coordination compounds comprise a ligand selected from the group consisting of Formulae 1–7. Most preferred is where the metal is Rh, and the ligand is of Formula 1A where wherein SS is polystyrene, L is —$CH_2$—, A is selected from the group consisting of an optionally-substituted carbon chain of 1–3 carbon atoms and an optionally-substituted carbon ring of 6–12 carbon atoms, Z is selected from the group consisting of an optionally-substituted carbon chain of 1–10 carbon atoms, —($NR_4$)—, and —O—, $R_4$ is selected from the group consisting of chloro, cyclohexyl, n-propyl, i-propyl, n-butyl, phenyl, and t-butyl, $R_1$, $R_2$, and $R_3$ are independently selected from the group consisting of hydrogen, Cl, alkyl, alkenyl, aryl, $SQ_1$, $OQ_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle, and where $R_1$ and $R_2$ together with the P form a phosphole, aryl, or alkyl ring. Most preferred is where SS is polystyrene, A is $(CH_2)_2$, Z is N(t-butyl), and $R_1$, $R_2$, and $R_3$ are n-propyl.

Any solvent is suitable for this process provided that it is inert to all reagents and products. Optimum temperatures are about −80 to about 200° C., preferably about −80 to about 150° C.

EXAMPLES

The following non-limiting Examples are meant to illustrate the invention but are not intended to limit it in any way.

Materials and Methods

All manipulations of air-sensitive materials were carried out with rigorous exclusion of oxygen and moisture in flame-dried Schlenk-type glassware on a dual manifold Schlenk line, interfaced to a high-vacuum ($10^{-4}$–$10^{-5}$ Torr) line, or in a nitrogen-filled Vacuum Atmospheres glovebox with a high-capacity recirculator (1–2 ppm of $O_2$). Before use, all solvents were distilled under dry nitrogen over appropriate drying agents (such as sodium benzophenone ketyl and metal hydrides except for chlorinated solvents). Deuterium oxide, THF-$D_8$, $C_6D_6$ and chloroform-d were purchased from Cambridge Isotopes (Andover, Mass.). All organic and inorganic starting materials were purchased from Aldrich Chemical Co. (Milwaukee Wis.), Farchan Laboratories Inc. (Gainesville, Fla.), Strem Chemicals (Newburyport, Mass.), Calbiochem-NovaBiochem Corp. (San Diego, Calif.), Rieke Metals, Inc. (Lincoln, Nebr.), or Lancaster Synthesis Inc. (Windham, N.H.), and when appropriate were distilled prior to use. The substrates zirconium metallacycles 2,3,4,5-tetramethylphospholylchloride, 2,3,4,5-tetraethylphospholyl-chloride, and 1,7-di-tert-butyl-1,6-bicyclo[3,3]heptadiynylphospholylchloride were synthesized via modifications of literature methods (Fagan et al., *J. Am. Chem. Soc.* 1988, 110, pp. 2310–2312).

Physical and Analytical Measurements

NMR spectra were recorded on either a Nicolet NMC-300 wide-bore (FT, 300 MHz, $^1$H; 75 MHz, $^{13}$C, 121 MHz $^{31}$P), or GE QM-300 narrow-bore (FT, 300 MHz, $^1$H) instrument. Chemical shifts (δ) for $^1$H, $^{13}$C are referenced to internal solvent resonances and reported relative to $SiMe_4$. $^{31}$P NMR shifts are reported relative to external phosphoric acid. Analytical gas chromatography was performed on a Varian Model 3700 gas chromatograph with FID detectors and a Hewlett-Packard 3390A digital recorder/integrator using a 0.125 in. i.d. column with 3.8% w/w SE-30 liquid phase on Chromosorb W support. GC/MS studies were conducted on a VG 70-250 SE instrument with 70 eV electron impact ionization.

Example 1

Reaction of Merrifield Resin With tert-Butylamine

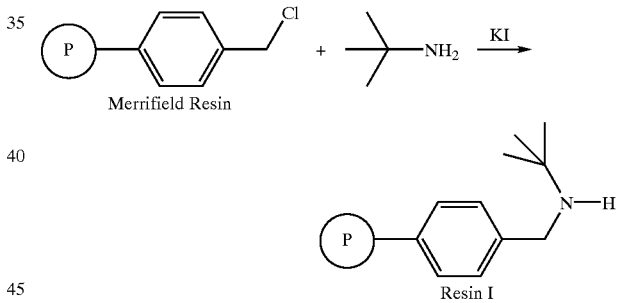

A solution of t-butylamine (70 g, 0.95 moles) and KI (0.3 g, 2 mmol) in 800 mL of THF was treated with Merrifield resin (chloromethylpolystyrene-divinylbenzene crosslinked with 2% divinylbenzene, 50 g, 0.89 mmol/g, 44.5 mmol) while stirring at room temperature for 30 min. The suspension was then refluxed for 48 h before the solution was filtered off. The resulting resin was washed sequentially with water (3×250 mL), THF (3×150 mL), hexane (3×200 mL). After drying in vacuo overnight, 51 g of the resin was obtained (98% yield according to N elemental analysis, anal. calculated for polymer-NHC(Me)$_3$: N, 1.25. Found: N, 1.22). The disappearance of $^1$H resonances of polymer-Ph—$CH_2$—Cl (δ$CH_2$=~4.5 ppm) and the appearance of $^1$H resonances of polymer-Ph—$CH_2$—NHC(Me)$_3$ (δ$CH_2$=~3.7 ppm) indicates the complete transformation of the chloromethyl groups to tert-butylaminomethyl groups. Hereafter, this will be referred to as Resin I.

Example 2

Reaction of Tertiary-butylaminomethyl Merrifield Resin and 1,2-bis(Dichlorophosphino)ethane

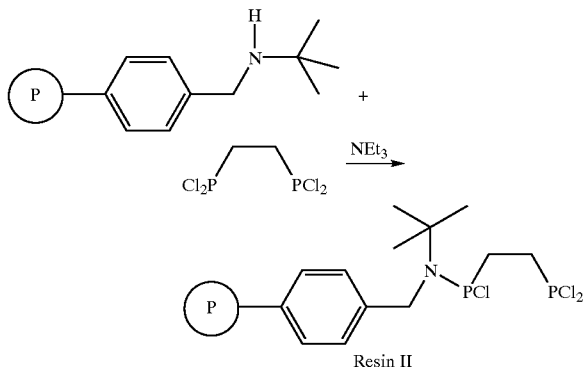

Resin II

A solution of $Cl_2PCH_2CH_2PCl_2$ (15 g, 64.7 mmol) in 200 mL of THF was treated slowly with Resin I (15 g, 0.72 mmol/g, 10.8 mmol) while stirring at room temperature for a period of 30 min. before $Et_3N$ (5 g, 49 mmol) was added. The resulting suspension was stirred at room temperature overnight before the solution was filtered off. The resin was sequentially washed with hexane (2×50 mL), $CH_2Cl_2$ (3×80 mL), and hexane (2×30 mL). The resulting resin was dried in vacuo overnight. $^{31}P$ NMR (122 MHz, $C_6D_6$): δ 195, 152 ppm. Hereafter this will be referred to as Resin II.

Example 3

Reaction of 1,2-bis(Dichlorophosphino)ethane With 1% Divinylbenzene Crosslinked Polystyrene Containing 0.80 mmol/g of Hydroxymethyl Substitution

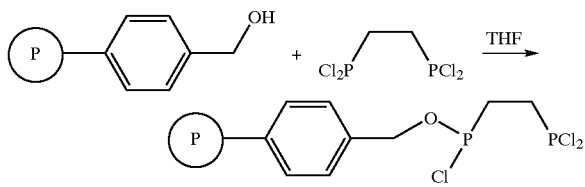

A 500 mL round bottomed flask with a magnetic stirrer was charged with 10.0 g of $Cl_2PCH_2CH_2PCl_2$ and 100 mL of tetrahydrofuran. In a 300 mL beaker was mixed 25 g of 1% divinylbenzene cross-linked polystyrene with a loading of hydroxymethyl groups of 0.80 mmol/g (NovaBiochem 01-64-0110), 150 mL of tetrahydrofuran, and 3.00 g of 8.08 g of triethylamine. The mixture was added slowly to the flask containing the $Cl_2PCH_2CH_2PCl_2$ and was stirred for 4.0 h at room temperature. The resin was isolated by filtration, was washed once with 100 mL of tetrahydrofuran, five times with 100 mL of hexane, four times with 100 mL portions of dichloromethane, and twice with 100 mL portions of hexane. The resin was then dried under high vacuum. $^{31}P\{^1H\}$ NMR (122 MHz, $C_6D_6$ solvent): δ 201 (broad singlet, 1 P), 194 (broad singlet, 1 P).

Example 4

Reaction of Merrifield Resin With 1,5-bis (Bromomagnesium)pentane Followed by Reaction with 1,2-bis(Dichlorophosphino)ethane

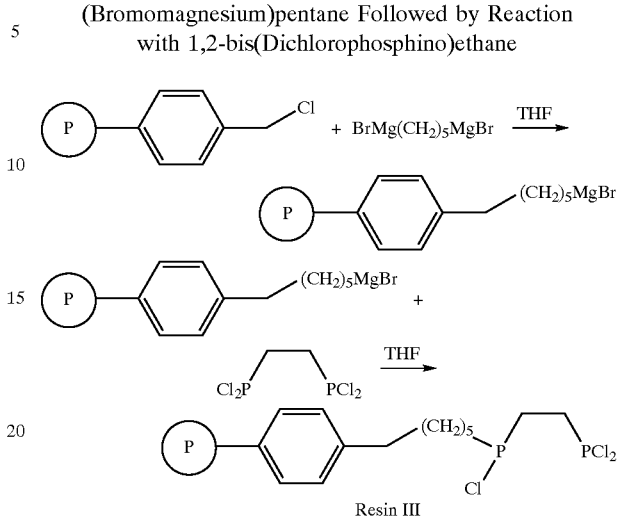

Resin III

A two-necked 2 L round-bottomed flask with magnetic stirrer was charged with 500 mL (250 mmol) of $BrMg(CH_2)_5MgBr$ (0.5 M in tetrahydrofuran) and 250 mL of tetrahydrofuran. To this was added while stirring 50 g (50 mmol) of Merrifield Resin (polystyrene 1% crosslinked with divinylbenzene, and 1.0 mmol/g of chloromethyl group substitution) in small portions over 30–40 minutes. The reaction mixture was stirred overnight at room temperature, and was then refluxed for 2 d. After cooling, the resin was isolated by filtration, was washed five times sequentially with 300 mL portions of tetrahydrofuran and 300 mL of hexane. This was then dried in vacuo. A one liter round-bottomed flask with a magnetic stirring bar was charged with 1,2-bis(dichlorophosphino)ethane (46.4 g, 200 mmol) and tetrahydrofuran 500 mL. The resin was added to this solution, and the reaction mixture was stirred at room temperature overnight. The resin was collected by filtration and was washed five times with 300 mL portions of tetrahydrofuran, and then five times with 300 mL of hexane. It was then dried in vacuo. Hereafter, this will be referred to as Resin III. $^{31}P\{^1H\}$ NMR (122 MHz, $C_6D_6$ solvent): δ 107 (broad singlet); 197 (broad singlet). In some cases integration of these two resonances indicated the phosphorus reagent crosslinked some of the alkyl linking chains of the polymer to the degree of approximately 20%.

Example 5

Reaction of Resin II With Grignard Reagents

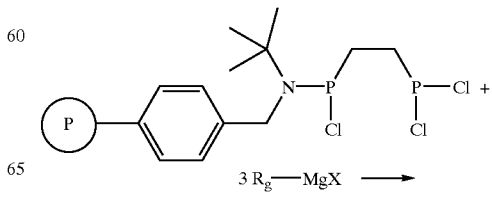

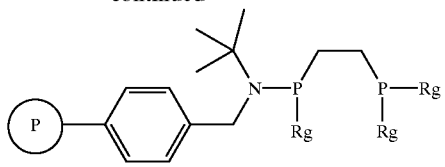

To each of sixteen 20 mL glass vials was added 1.35 g of Resin II. To each of these vials was added the Grignard solution in the amount and concentration indicated in Table 2A below, and the volume in each vial was brought up to nearly the top of the vial by addition of tetrahydrofuran. The capped vials were agitated on an orbital shaker for 24 h, and each resin was collected by filtration. Each resin was washed twice with 10 mL of tetrahydrofuran, twice with 10% water/tetrahydrofuran, twice with 10 mL of tetrahydrofuran, and twice with 10 mL of hexane. The resins were then dried in vacuo and analyzed by $^{31}P$ NMR (121 MHz, $C_6D_6$). Table 2A indicates the Grignard reagent and the molarity used, solvent, volume of reagent, yield, and NMR analysis of resulting products.

TABLE 2A

| Ex. | $R_g$-MgX | MOLARITY | SOLVENT | VOL. (mL) | YIELD (g) | $^{31}P$ δ |
|---|---|---|---|---|---|---|
| 5-A | (4-methylphenyl)MgBr | 1.0 | Ether | 9 | 1.42 | 46 |
| 5-B | (4-chlorophenyl)MgBr | 1.0 | Ether | 9 | 1.54 | 45 |
| 5-C | (4-tert-butylphenyl)MgBr | 2.0 | Ether | 4.5 | 1.57 | 46 |
| 5-D | (ethynyl)MgBr | 0.5 | THF | 18 | 1.74 | 46 |
| 5-E | (propynyl)MgBr | 0.5 | THF | 18 | 1.33 | 46 |
| 5-F | (4-fluorophenyl)MgBr | 2.0 | Ether | 4.5 | 1.52 | 45 |
| 5-G | (vinyl)MgBr | 1.0 | THF | 9 | 1.21 | 46 |
| 5-H | (cyclopentyl)MgBr | 2.0 | Ether | 4.5 | 1.37 | 59 |
| 5-I | (decyl)MgBr | 1.0 | Ether | 9 | 1.51 | 47 |
| 5-J | (3,4-difluorophenyl)MgBr | 0.5 | THF | 18 | 1.52 | 46 |
| 5-K | (4-n-butylphenyl)MgBr | 0.5 | THF | 18 | 1.51 | 46 |
| 5-L | (3-fluoro-2-methylphenyl)MgBr | 0.5 | THF | 18 | 1.63 | 37 |
| 5-M | (4-methylthiophenyl)MgBr | 0.5 | THF | 18 | 1.53 | 46 |
| 5-N | (3-methoxyphenyl)MgBr | 0.5 | THF | 18 | 1.52 | 48 |
| 5-O | (3-fluoro-4-methylphenyl)MgBr | 0.5 | THF | 18 | 1.51 | 46 |
| 5-P | (4-methoxyphenyl)MgBr | 0.5 | THF | 18 | 1.49 | 44 |

Example 6

Reaction of Resin II With bis(Cyclopentadienyl)-1,2,3,4-tetramethylbuta-1,4-dienylzirconium(IV)

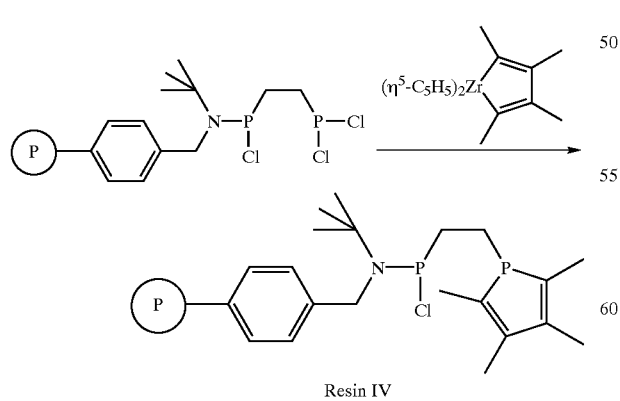

Resin IV

Resin II (5 g) was reacted with 2.0 g of bis(cyclopentadienyl)-1,2,3,4-tetramethylbuta-1,4-dienylzirconium(IV) in anhydrous dichloromethane at room temperature. The resin was collected by filtration, was washed twice with 100 mL of hexane, and then three times with 100 mL of dichloromethane. It was then dried in vacuo. Hereafter, this will be referred to as Resin IV. $^{31}P\{^1H\}$ NMR (122 MHz, $CDCl_3$ solvent): δ 14 (broad singlet); 160 (broad singlet).

Example 7

Reaction of Resin II With bis(Cyclopentadienyl)-dimethyl-1,4-dienylzirconium(IV)

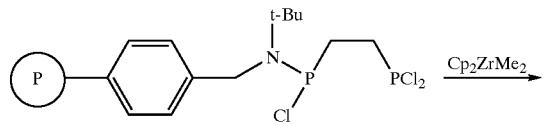

A suspension of Resin II (0.9 g, ~1.24 mmol/g, 1.1 mmol) in 100 mL of THF was treated with ($\eta^5$-$C_5H_5$)$_2$ZrMe$_2$ (0.70 g, 2.8 mmol) at room temperature for 8 h before the solution was filtered off. The resulting resin was washed with THF (3×30 mL), $CH_2Cl_2$ (2×30 mL) and hexane (2×20 mL). The resin was dried in vacuo overnight. The polymer-supported 1-(1,1-dimethylphosphino)-2-chlorophosphinoethane, 0.9 g, was obtained. $^{31}P$ NMR (122 MHz, $C_6D_6$): δ 155, −47 ppm.

Example 8

Reaction of Resin IV With 2,4,6-Trimethylphenylmagnesium Bromide

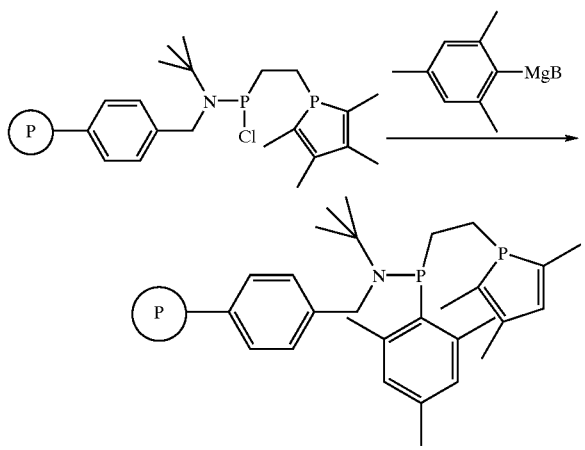

Resin IV was reacted with an excess of 1.0 M solution of 2,4,6-trimethylphenylmagnesium bromide in ether. The resin was collected by filtration, and was washed twice with 100 mL portions of tetrahydrofuran, twice with 100 mL portions of hexane, twice with 150 mL portions of dichloromethane, once with 5% water/tetrahydrofuran, and finally twice with 100 mL portions of dichloromethane. $^{31}\{^1H\}$ NMR (122 MHz, CDCl$_3$ solvent): δ 17 (broad singlet); 49 (broad singlet).

Example 9

Reaction of Resin III With Grignard Reagents

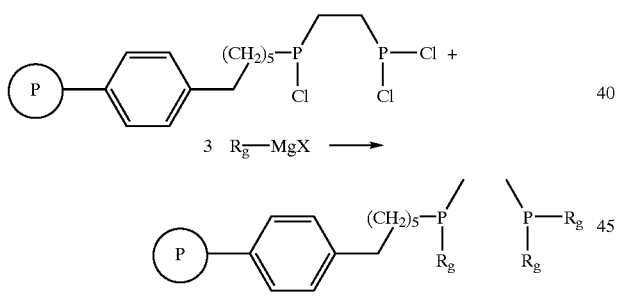

Thirty-two 20 mL glass vials were charged 1.0 g (1.0 mmol) of Resin III. To each vial was added 9.0 mmol of a Grignard reagent as listed in the Table 3A below. The reactions were shaken overnight. Then the resin in each vial was collected by filtration, and washed with in order with the following solvents: tetrahydrofuran (2×10 mL), hexane (2×10 mL), 10% water/tetrahydrofuran (12 mL), tetrahydrofuran (2×10 mL), hexane (2×10 mL), tetrahydrofuran (2×10 mL), and hexane (2×10 mL). Each sample was then dried by flushing with nitrogen. The yield of each isolated resin was in the range 1.02–1.110 g. All of the resins had $^{31}$P NMR peaks in the range 50 to −50 ppm relative to external phosphoric acid which indicated the expected products. Table 3A indicates the Grignard reagent, molarity used, and volume of reagent.

Example 9-FF was prepared using the above procedure, except that (2-thiophenyl)Li was used in place of a Grignard reagent.

TABLE 3A

| Ex. | R$_g$-MgX | MOLARITY | VOL. (mL) |
|---|---|---|---|
| 9-A | (methyl)MgBr | 3 | 3 |
| 9-B | (ethyl)MgBr | 2 | 4.5 |
| 9-C | (n-propyl)MgBr | 2 | 4.5 |
| 9-D | (isopropyl)MgBr | 2 | 4.5 |
| 9-E | (butyl)MgBr | 2 | 4.5 |
| 9-F | (iso-butyl)MgBr | 2 | 4.5 |
| 9-G | (2-butyl)MgCl | 2 | 4.5 |
| 9-H | (cyclopentyl)MgBr | 2 | 4.5 |
| 9-I | (cyclohexyl)MgBr | 2 | 4.5 |
| 9-J | (dodecyl)MgBr | 1 | 9 |
| 9-K | (pentadecyl)MgBr | 0.5 | 18 |
| 9-L | (phenyl)MgBr | 3 | 3 |
| 9-M | (2-methyl-2-phenylpropyl)MgCl | 0.5 | 18 |
| 9-N | (ortho-tolyl)MgCl | 1 | 9 |
| 9-O | (meta-tolyl)MgCl | 1 | 9 |
| 9-P | (para-tolyl)MgBr | 1 | 9 |
| 9-Q | (4-tert-butylphenyl)MgBr | 2 | 4.5 |
| 9-R | (4-fluorophenyl)MgBr | 2 | 4.5 |
| 9-S | (3-bis(trimethylsilyl)aminophenyl)MgCl | 1 | 9 |
| 9-T | (2,6-dimethylphenyl)MgBr | 1 | 9 |
| 9-U | (3,4-difluorophenyl)MgBr | 0.5 | 18 |
| 9-V | (3-fluoro-2-methylphenyl)MgBr | 0.5 | 18 |
| 9-W | (4-methylthiophenyl)MgBr | 0.5 | 18 |
| 9-X | (3-methoxyphenyl)MgBr | 0.5 | 18 |
| 9-Y | (3-fluoro-4-methylphenyl)MgBr | 0.5 | 18 |
| 9-Z | (2-methoxyphenyl)MgBr | 0.5 | 18 |
| 9-AA | (4-methoxyphenyl)MgBr | 0.5 | 18 |
| 9-BB | (4-phenoxyphenyl)MgBr | 0.5 | 18 |
| 9-CC | (2,4-difluorophenyl)MgBr | 0.5 | 18 |
| 9-DD | (2-naphthyl)MgBr | 0.25 | 36 |
| 9-EE | (4-dimethylaminophenyl)MgBr | 0.5 | 18 |
| 9-FF | (2-thiophenyl)Li | 1 | 9 |

Example 10

Reaction of Resin I With 1,2-bis(Dichlorophosphino)benzene

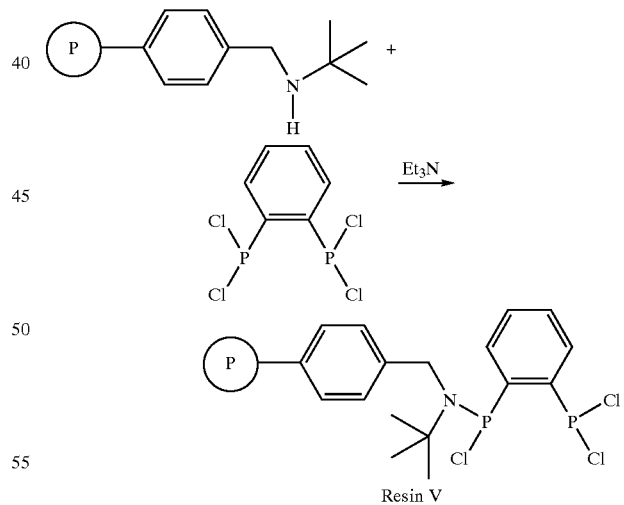

Polymer-supported 1-(1,1-dichlorophosphino)-2-chlorophosphinobenzene was prepared using the procedure for Resin II with 1,2-bis(dichlorophosphino)benzene used in place of 1,2-bis(dichlorophosphino)ethane. 1,2-bis(dichlorophosphino)benzene (12 g, 42.9 mmol) in 300 mL of THF was treated slowly with Resin I (10 g, 0.72 mmol/g, 7.2 mmol) and Et$_3$N (4.4 g, 43.5 mmol). $^{31}$P NMR (122 MHz, C$_6$D$_6$): δ 162, 124 ppm. Hereafter this will be referred to as Resin V.

Example 11

Reaction of Resin V With 4-Methylphenylmagnesium Bromide

A suspension of Resin V (0.6 g, ~0.72 mmol, 0.43 mmol) in 15 mL of THF was treated with 4-methylphenylmagnesium bromide (0.5 M solution in diethylether, 5.1 mmol) at room temperature for 5 min. The resulting mixture was stirred for 2 h before the solution was filtered off and the resin was washed with $H_2O$ (2×10 mL), $CH_2Cl_2$ (2×20 mL) and hexane (3×20 mL). After drying in vacuo, ca. 0.6 g of the polymer-bound 1-[1,1-di(4-methylphenyl)phosphino]-2-(4-methylphenyl)phosphinobenzene was obtained. $^{31}P$ NMR (122 MHz, $C_6D_6$): δ 43, −13 ppm.

Example 12

Reaction of Resin II With 3,5-Difluorophenylmagnesium Bromide

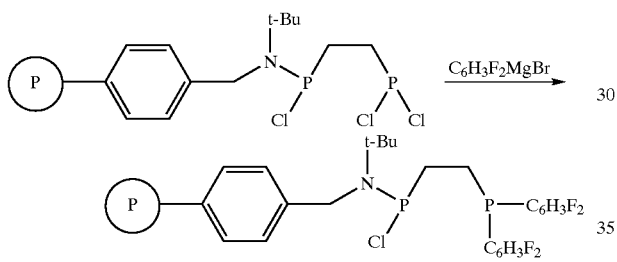

A suspension of Resin II (2 g, ~0.72 mmol/g, 1.44 mmol) in 100 mL of THF was treated with 3,5-difluorophenylmagnesium bromide (0.5 M in diethyl ether, 4.3 mmol) at room temperature for 8 h before the solution was filtered off. The resulting resin was washed with THF (3×15 mL), $CH_2Cl_2$ (2×20 mL) and hexane (2×20 mL). The resin was dried in vacuo overnight. The polymer-supported 1-[di(3,5-difluorophenyl)phosphino]-2-(chlorophosphino)ethane, 2.0 g, was obtained. $^{31}P$ NMR (122 MHz, $C_6D_6$): δ 155, −7.4 ppm.

Example 13

Reaction of Resin I With Mono-substituted 1,2-bis(Dichlorophosphino)ethane

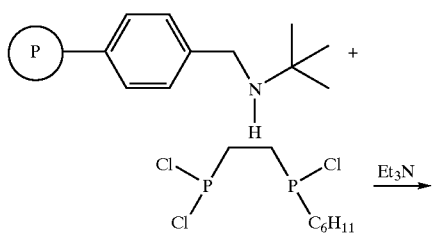

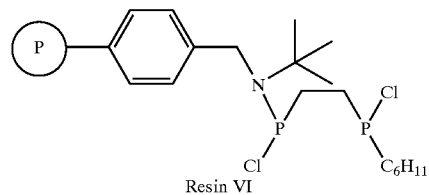
Resin VI

A solution of $Cl_2PCH_2CH_2PCl_2$ (3.0 g, 12.6 mmol) in 200 mL of THF was treated slowly with cyclohexylzinc bromide (0.5 M in diethyl ether, 12.5 mmol) while stirring at 0° C. for a period of 30 min. before the resulting solution was warmed to room temperature and stirred overnight. The resulting mixture of cyclohexyl-substituted diphosphines were treated slowly with Resin I (2.0 g, 0.72 mmol/g, 1.44 mmol) for 10 min. before $Et_3N$ (0.73 g, 7.2 mmol) was added. The resulting suspension was stirred at room temperature overnight before the solution was filtered off. The resin was washed sequentially with hexane (2×30 mL), $CH_2Cl_2$ (3×30 mL), hexane (2×20 mL), and dried in vacuo overnight. $^{31}P$ NMR (122 MHz, $C_6D_6$): δ 155, 120 ppm. Hereafter this will be referred to as Resin VI.

Example 14

Reaction of Resin II With $Zr(OCH_2CH_2CH_3)_4$

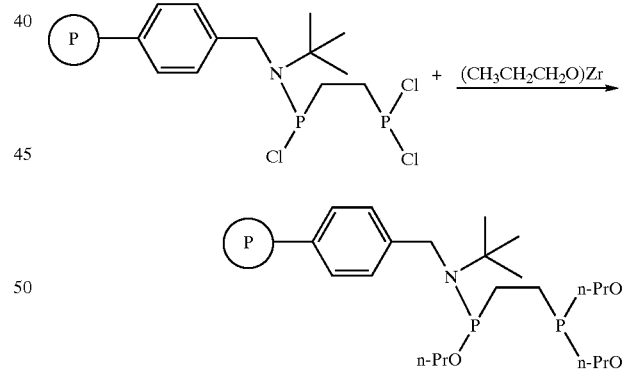

A suspension of Resin II (10 g, 1.24 mmol/g, 12.4 mmol) in 250 mL of THF was treated slowly with $Zr(OCH_2CH_2CH_3)_4$ (6.7 g, 20.5 mmol). The resulting mixture was stirred at room temperature for 4 h before the solution was filtered off and the resin was washed with THF (3×50 mL), $H_2O$ (2×10 mL), hexane (3×30 mL). The polymer-bound $—P(OCH_2CH_2CH_3)CH_2CH_2P(OCH_2CH_2CH_3)_2$ 10 g, was obtained. $^{31}P$ NMR (122 MHz, $C_6D_6$): δ 183, 138 ppm.

Example 15

Reaction of Chloromethylated Resin II With Lithium Phenoxide

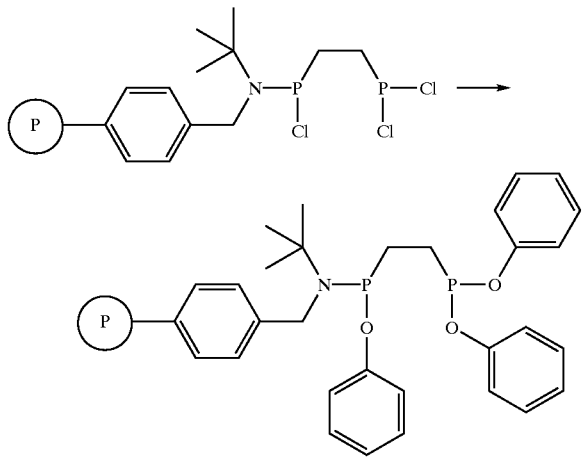

A resin analogous to Resin II was prepared as follows. To 10 g of 2% divinylbenzene cross-linked chloromethylated polystyrene (1.25 mmol of chloromethyl groups per gram) in 300 mL of tetrahydrofuran was added to a solution of tert-butylamine (14 g, 190 mmol). The reaction mixture was refluxed overnight and the resin was filtered, washed with H$_2$O (200 mL), tetrahydrofuran (200 mL), hexane (200 mL), H$_2$O (100 mL), and diethyl ether (200 mL). The resulting resin was dried in vacuo overnight. The resin was slowly added to a solution of Cl$_2$PCH$_2$CH$_2$PCl$_2$ (7.4 g, 31.9 mmol) and Et$_3$N (6.5 g, 64.2 mmol) in tetrahydrofuran (300 mL) at room temperature, and the resulting mixture was stirred overnight before filtration and washing with tetrahydrofuran (2×100 mL), hexane (2×100 mL), CH$_2$Cl$_2$ (2×100 mL), and hexane (2×100 mL). The resin was added to tetrahydrofuran (150 mL), and then at room temperature treated with a mixture of tetrahydrofuran (50 mL) and lithium phenoxide (62.0 mmol). After the mixture was stirred for 4 hr, the solvents were filtered off and the resulting resin was washed with tetrahydrofuran (3×100 mL), H$_2$O (2×100 mL), and hexane (3×200 mL), dried in vacuo to give ca. 10 g of the title polymer-bound compound.

$^{31}$P NMR (122 MHz, C$_6$D$_6$): δ 182, 137.

Example 16

Reaction of Resin VI With Lithium Phenoxide

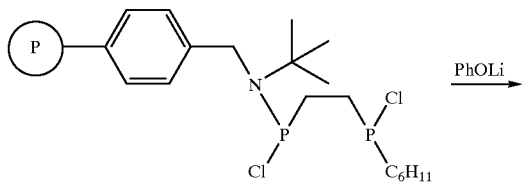

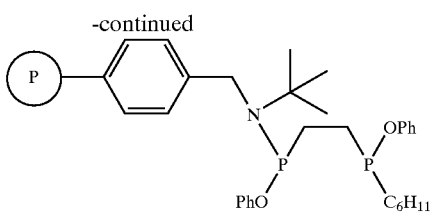

A suspension of Resin VI (2 g, ~0.72 mmol/g, 1.44 mmol) in 100 mL of THF was treated with PhOLi (1.0 M in diethyl ether, 7.2 mmol) at room temperature for 2 h before the solution was filtered off. The resulting resin was washed with H$_2$O (5 mL), THF (2×20 mL) and hexane (2×20 mL). The resin was dried in vacuo overnight. $^{31}$P NMR (122 MHz, C$_6$D$_6$): δ 182, 139 ppm.

COMBINATORIAL SYNTHESES

Example 17

Reaction of Resin II With a Mixture of Grignard Reagents

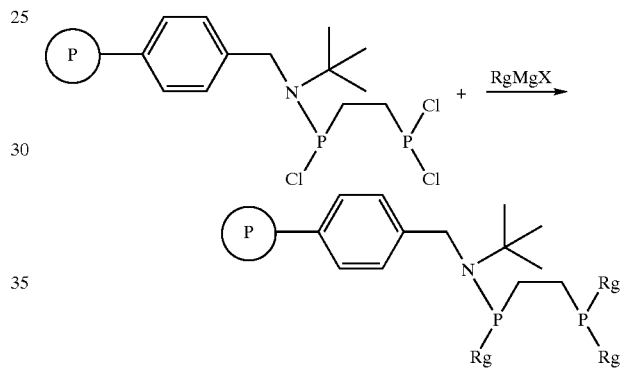

A suspension of Resin II (1.0 g, ~0.88 mmol/g, 0.88 mmol) in 15 mL of THF was treated slowly with a mixture of n-propylmagnesium bromide (2.0 M in diethyl ether, 0.44 mmol) and 3,5-difluorophenylmagnesium bromide (0.5 M in diethyl ether, 0.44 mmol) over a period of 5 min. at room temperature. The resulting suspension was stirred at room temperature for 30 min. before the solution was filtered off and the resin was washed with THF (2×20 mL). The procedures above were successively repeated 4 times with the same amount of RMgBr mixture before the solution was filtered off and the resin was washed with H$_2$O (2×3 mL), THF (2×10 mL) and hexane (2×15 mL). After drying in vacuo, a polymer-supported mixture of six components, 1.0 g, was obtained.

The resulting mixture resin with six components, and EtOH (0.28 g, 6.1 mmol) in 5 mL of THF was refluxed overnight. After cooling to room temperature, the resin was filtered off and washed with THF (2×5 mL). The combined filtrates were dried in vacuo. By $^{31}$P-NMR and mass spectrum analysis it was shown that the mixture contained 6 compounds. $^{31}$P NMR (122 MHz, C$_6$D$_6$): δ 133.5, −27.4 ppm; 132.8, −16.6 ppm, 132.5, −16.9 ppm (cis- and trans-isomers); 132.1, −8.0 ppm; 120.4, −27.7 ppm; 119.3, −17.0 ppm, 119.1, −17.4 ppm (cis- and trans-isomers); 118.1, −8.5 ppm.

A polymer-supported mixture of 936 components (ligands) was produced according to the procedure above except that the resin was treated with a mixture of 12 $R_g$MgX reagents ($R_g$=n-propyl, cyclopentyl, t-butyl, phenyl, 4-t-butylphenyl, 2,4,6-trimethylphenyl, 4-anisole, 3-anisole, 2-anisole, 4-fluorophenyl, 3,4-difluorophenyl, 3,5-difluorophenyl) instead of 2 $R_g$MgX reagents.

CLEAVAGE OF LIGANDS FROM THE RESIN

Example 18

Synthesis of 1-[di(3,5-Diflurophenyl)phosphino]-2-(chloro-3,5-diflurophenylphosphino)ethane

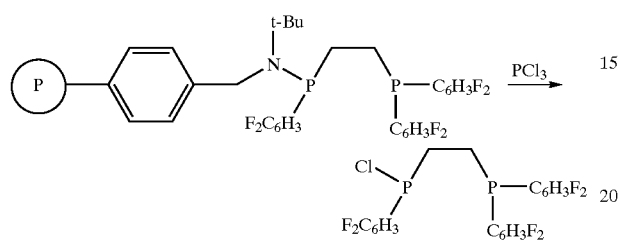

A suspension of Resin II (4.0 g, ~0.96 mmol/g, 3.84 mmol) in 150 mL of THF was treated with 3,5-difluorophenylmagnesium bromide (0.5 M in diethyl ether, 38.4 mmol, 10 eq) at room temperature for 20 min, then the mixture was stirred overnight before the solution was filtered off. The resulting resin was washed with THF (2×50 mL), H$_2$O (20 mL), THF (4×50 mL), and hexane (3×50 mL). The resin was dried in vacuo overnight. The polymer-supported 1-[di(3,5-difluorophenyl)phosphino]-2-[chloro-3,5-difluorophenylphosphino)ethane, ~4.0 g, was obtained. $^{31}$P NMR (122 MHz, CDCl$_3$): δ 49.2, −7.3 ppm.

A suspension of the above resin (2.0 g, 0.96 mmol/g, ~1.92 mmol,) in THF (100 mL) was treated dropwise with PCl$_3$ (2.64 g, 19.2 mmol) over 5 min. at room temperature. The resulting reaction mixture was then stirred overnight before the resin was filtered off and washed with THF (2×20 mL). Removal of solvents and excess PCl$_3$ in vacuo afforded 0.34 g (38%) of 1-[di(3,5-difluorophenyl)phosphino]-2-[chloro-3,5-diflurophenylphosphino)ethane. $^{31}$P NMR (202 MHz, CDCl$_3$): 90.8 (δ, J=29.8 Hz), −9.2 (δ, J=29.9 Hz). $^1$H NMR (500 MHz, CDCl$_3$): 7.03 (3H), 6.75 (6H), 2.02 (4H). 13C NMR (125.8 MHz, CDCl$_3$): 164.1, 162.0, 141.9, 140.9, 115.1, 113.4, 106.3, 105.1, 32.4, 22.0. HRMS Calcd for C$_{20}$H$_{13}$F$_6$P$_2$Cl: 464.0085. Found: 464.0075.

Example 19

Synthesis of 1-(Diphenylphosphinite)-2-(chlorophenylphosphinite)ethane

Method A: A suspension of polymer-bound —P(PhO)CH$_2$CH$_2$P(OPh)$_2$ (from Example 15, 0.5 g, 1.25 mmol/g, ~0.62 mmol) in THF (20 mL) was treated dropwise with PCl$_3$ (0.43 g, 3.1 mmol). The resulting reaction mixture was then stirred overnight before the resin was filtered off and washed with THF (10 mL). The filtrate was dried in vacuo to remove the solvent and excess PCl$_3$, the residue was extracted with 3×20 mL of hexane. The combined hexane extracts were dried under reduced pressure to give 0.12 g (48% yield) of (PhO)ClPCH$_2$CH$_2$P(OPh)$_2$.

$^{31}$P NMR (122 MHz, C$_6$D$_6$): δ 199.5 (d, J=16.8 Hz), 178.9 (d, J=16.8 Hz) ppm.

Method B: A mixture of polymer-bound —P(PhO)CH$_2$CH$_2$P(OPh)$_2$ (from Example 15, 0.5 g, 1.25 mmol/g, ~0.62 mmol) and TMSCl (10 eq., 6.2 mmol) in THF (20 mL) was stirred at room temperature for 4 days before the resin was filtered off, the solvent and excess TMSCl were removed in vacuo. The phosphorus-31 NMR spectrum of the crude filtrate indicated the presence of the title compound (ca. 90%).

Example 20

Synthesis of 1-(Diphenylphosphino)-2-(ethoxylphenylphosphinite)ethane

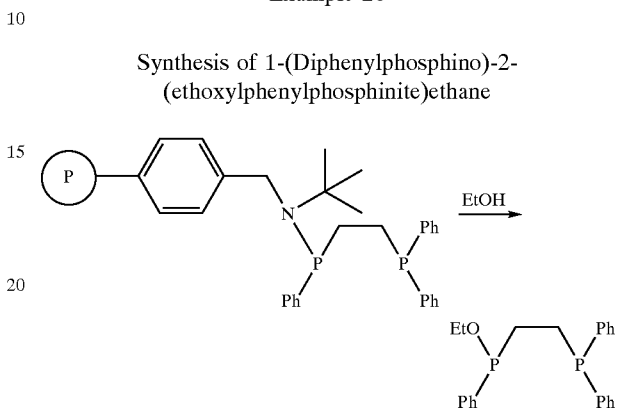

A suspension of polymer-bound —P(Ph)CH$_2$CH$_2$P(Ph)$_2$ prepared as in Example 5 using phenyl magnesium bromide (13.6 g, 0.74 mmol/g, ~10.1 mmol), and EtOH (5 g, 109 mmol) in THF (200 mL) was refluxed overnight before the resin was filtered off and washed with THF (2×10 mL). The filtrate was dried in vacuo to remove the solvent and excess EtOH, the residue was extracted with 3×20 mL of hexane. The combined hexane extracts were dried under reduced pressure to give 2.17 g (59% yield) of (Ph)(EtO)PCH$_2$CH$_2$P(Ph)$_2$. $^{31}$P NMR (122 MHz, C$_6$D$_6$): δ 120.4, −11.6 ppm.

Example 21

Preparation of Catalyst

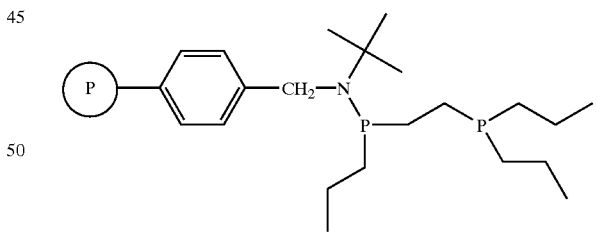

A flask was charged with 0.50 g of resin prepared as in Example 5 using n-propylmagnesium bromide and Resin II, 0.50 g (1,5-cyclooctadiene)rhodium(I) chloride dimer, and 20 mL of methylene chloride. This was allowed to stir at room temperature for 8 h. It was then filtered and the product was washed with hexane (2×15 mL), THF (2×10 mL), methylene chloride (2×10 mL), hexane (2×15 mL). To remove all excess (1,5-cyclooctadiene)rhodium(I) chloride dimer, the resin was then washed in portions with a total of 500 mL of methylene chloride until the washings were colorless. The resin was then dried in vacuo.

Example 22

Reaction of Salicylalde and Butyl Acrylate to Form Coumarin

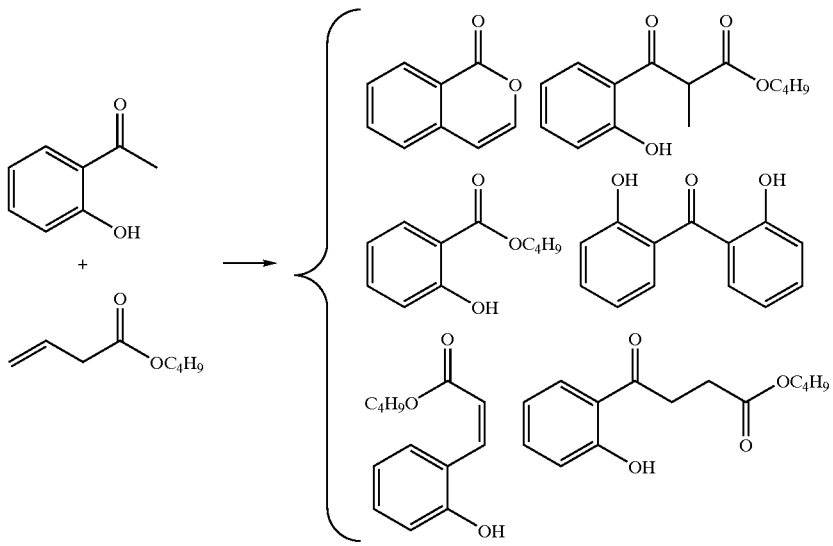

A flask was charged with 0.200 g of the complexed resin of Example 21, 1.00 g of salicylaldehyde, 2.00 g of butylacrylate, 0.122 g of sodium carbonate, and 5 mL of toluene. This was stirred at 100° C. for 48 h. The reaction mixture was filtered from the catalyst resin and then divided into two equal portions. The portions were each placed onto a 20×20 cm, 2000 micron thick silica gel preparatory chromatography plate, and each plate was eluted with 10% ethyl acetate/hexane solution.

On each of the plates, six bands were observed with the following $R_f$ values: Band 1, $R_f$ range 0.84–0.93; Band 2, $R_f$ range 0.78–0.84; Band 3, $R_f$ range 0.61–0.68; Band 4, $R_f$ range 0.50–0.59; Band 5, $R_f$ range 0.22–0.43; Band 6, $R_f$ range 0.00–0.22. Each band was scraped off the plates, and the bands from each with similar $R_f$ ranges were combined and extracted with 75 mL of ethylacetate. Solvent was removed from these extracts in vacuo. The final weight from each band is as follows: Band 1, 40 mg; Band 2, 50 mg; Band 3, 200 mg; Band 4, 90 mg; Band 5, 200 mg; Band 6, 110 mg. Proton NMR spectra and mass spectra were taken of each sample.

The product from Band 1 was identified as 2-hydroxybenzoic acid butyl ester with hydrocarbon impurities. The product from Band 2 was identified as essentially pure 2-hydroxybenzoic acid butyl ester. The product from Band 3 was identified as 3-(2-hydroxyphenyl)-2-methyl-3-oxo-propionic (~90 mol %). The product from Band 4 was identified as a mixture of 4-(2-hydroxyphenyl)-4-oxo butyric acid butyl ester and 2,2'-dihydroxybenzophenone in a 1.4:1 mole ratio, respectively. The 4-(2-hydroxyphenyl)-4-oxo-butyric acid butyl ester was further purified by elution with 1:1 methylene chloride:hexane on a preparatory silica gel chromatography plate. Two bands were partially separated. The bottom portion of the band was scraped off the plate and extracted with ethylacetate. Removal of solvent in vacuo yielded pure 4-(2-hydroxyphenyl)-4-oxo-butyric acid butyl ester. The product from Band 5 was a mixture of coumarin and Z-3-(2-hydroxyphenyl)-acrylic acid butyl ester in a 1:2 mole ratio, respectively. The products in Band 6 were a complex mixture of unidentified organic compounds. Based on the amount of starting salicylaldehyde, the following percent yields of each compound were obtained: 2-hydroxybenzoic acid butyl ester (3%), 3-(2-hydroxyphenyl)-2-methyl-3-oxo-propionic acid butyl ester (10%), 4-(2-hydroxyphenyl)-4-oxo butyric acid butyl ester (3%), 2,2'-dihydroxybenzophenone (2%), Z-3-(2-hydroxyphenyl)-acrylic acid butyl ester (8%), and coumarin (4%).

Polymer-Supported Synthesis of Diphosphine Monoxide Ligands

Method A

Example 23

Synthesis of $MePH(O)CH_2CH_2PMe_2$

A suspension of polymer-bound $(Me)PCH_2CH_2P(Me)_2$ (2.0 g, 1.0 mmol/g, 2.0 mmol, prepared using the procedure in Example 5 with methylMgBr) and $H_2O$ (0.60 g, 33.3 mmol) in THF (10 mL) was refluxed overnight, then the resin was filtered off and washed with THF (2×10 mL). Removal of solvents and excess $H_2O$ from the filtrates by vacuum afforded 100 mg (33% yield) of $MePH(O)CH_2CH_2PMe_2$. It was >95% pure by $^1H$ NMR and GC/MS. $^{31}P$ NMR (121 MHz, $CDCl_3$, $^1H$-decoupled): δ 30.3 (d, $J_{p-p}$=38.1 Hz), −44.5 (d, $J_{p-p}$=38.1 Hz). $^{31}P$ NMR (121 MHz, $CDCl_3$, $^1H$-coupled): δ 30.3 (d, $J_{p-H}$=457.6 Hz), −44.5 (s). $^1H$ NMR (500 MHz, $CDCl_3$): δ 7.00 (d, $J_{p-H}$=457.6 Hz, 1H), 1.83 (m, 3H), 1.58–1.521 (m, 4H), 0.99 (m, 6H). $^{13}C$ NMR (125 MHz, $CDCl_3$): δ 25.4 (d, $J_{p-c}$=65.9 Hz), 21.8, 13.1(d, $J_{p-c}$=65.7 Hz), 12.6. HRMS: Calcd for $C_5H_{14}P_2O(M^+)$: 152.0520. Found: 152.0527.

Example 24

Synthesis of $EtPH(O)CH_2CH_2PEt_2$

A similar procedure to that described above was used to prepare $EtPH(O)CH_2CH_2PEt_2$ using polymer-bound EtPCH$_2$CH$_2$PEt$_2$ (2.0 g, 0.96 mmol/g, 1.92 mmol, prepared using the procedure in Example 5 with ethylMgBr) and H$_2$O (0.6 g, 33.3 mmol). After the solvents were removed from the filtrates by vacuum, 160 mg (43% yield) of EtPH(O)CH$_2$CH$_2$PEt$_2$ was obtained. It was >95% pure by $^1$H NMR and GC/MS. $^{31}$P NMR (121 MHz, CDCl$_3$, $^1$H-decoupled): δ 36.2 (d, J$_{p-p}$=36.0 Hz), −16.7 (d, J$_{p-p}$=36.0 Hz). $^{31}$P NMR (121 MHz, CDCl$_3$, $^1$H-coupled): δ 39.7 (d, J$_{p-H}$=449.6 Hz), −16.6 (s). $^1$H NMR (500 MHz, CDCl$_3$): δ 6.78 (d, J$_{p-H}$=449.6 Hz, $^1$H), 1.79 (m, 4H), 1.63 (m, 1H), 1.35 (m, 3H), 1.15 (m, 3H), 1.00 (m, 6H). $^{13}$C NMR (125 MHz, CDCl$_3$): δ 24.0 (d, J$_{p-c}$=62.8 Hz), 20.9 (d, J$_{p-c}$=65.7 Hz), 18.4, 17.3, 9.3, 5.6. HRMS: Calcd for C$_8$H$_{20}$P$_2$O(M$^+$): 194.0989. Found: 194.0952.

Example 25

Synthesis of (CH$_3$CH$_2$CH$_2$)PH(O)CH$_2$CH$_2$P(CH$_2$CH$_2$CH$_3$)$_2$

A suspension of polymer-bound (CH$_3$CH$_2$CH$_2$)PCH$_2$CH$_2$P(CH$_2$CH$_2$CH$_3$)$_2$ (2.0 g, 0.92 mmol/g, 1.84 mmol, prepared using the procedure in Example 5 with n-propylMgBr) and H$_2$O (0.6 g, 33.3 mmol) in THF (10 mL) was refluxed overnight before the resin was filtered off and washed with THF (2×10 mL). Removal of solvents and excess H$_2$O from the filtrates by vacuum afforded 170 mg (39% yield) of the title compound. It was >90% pure by $^1$H NMR and GC/MS. $^{31}$P NMR (121 MHz, CDCl$_3$, $^1$H-decoupled): δ 35.8 (d, J$_{p-p}$=35.3 Hz), −26.3 (d, J$_{p-p}$=35.3 Hz). $^{31}$P NMR (121 MHz, CDCl$_3$, $^1$H-coupled): δ 35.8 (d, J$_{p-H}$=448.6 Hz), −26.3 (s). $^1$H NMR (500 MHz, CDCl$_3$): δ 6.83 (d, J$_{p-H}$=448.0 Hz, 1H), 1.78 (m, 4H), 1.61 (m, 4H), 1.50 (m, 2H), 1.49–1.35 (m, 6H), 1.02 (t, J=7.2 Hz, 3H), 0.94 (t, J=7.10 Hz, 6H). $^{13}$C NMR (125 MHz, CDCl$_3$): δ 29.5 (d, J$_{p-c}$=65.5 Hz), 28.4, 23.9 (d, J$_{p-c}$=62.8 Hz), 18.3, 17.5, 15.0, 14.8, 14.4. HRMS: Calcd for C$_{11}$H$_{26}$P$_2$O(M$^+$): 236.1459. Found: 236.1428.

Example 26

Synthesis of (Me$_2$CH)PH(O)CH$_2$CH$_2$P(CHMe$_2$)$_2$

An analogous procedure to that for (CH$_3$CH$_2$CH$_2$)PH(O)CH$_2$CH$_2$P(CH$_2$CH$_2$CH$_3$)$_2$ was used for the synthesis of title compound using polymer-bound (Me,CH)PCH$_2$CH$_2$P(CHMe$_2$)$_2$ (10.0 g, 0.92 mmol/g, 9.2 mmol, prepared using the procedure in Example 5 with i-propylMgBr) and H$_2$O (2.0 g, 111.1 mmol). After the solvents were removed from filtrates by vacuum, 912 mg (42% yield) of (Me$_2$CH)PH(O)CH$_2$CH$_2$P(CHMe$_2$)$_2$ was obtained. It was >95% pure by $^1$H NMR and GC/MS. $^{31}$P NMR (121 MHz, CDCl$_3$, $^1$H-decoupled): δ 46.8 (d, J$_{p-p}$=40.0 Hz), 10.5 (d, J$_{p-p}$=40.4 Hz). $^{31}$P NMR (121 MHz, CDCl$_3$, $^1$H-coupled): δ 46.8 (d, J$_{p-H}$=442.3 Hz), 10.5 (s). $^1$H NMR (500 MHz, CDCl$_3$): δ 6.55 (d, J$_{p-H}$=442.3 Hz, 1H), 1.94–1.82 (m, 3H), 1.76–1.65 (m, 4H), 1.51 (m, 1H), 1.69–1.10 (m, 6H), 1.04–0.98 (m, 12H). $^{13}$C NMR (125 MHz, CDCl$_3$): δ 26.3 (d, J$_{p-c}$=66.0 Hz), 24.0, 23.0, 18.5, 14.7, 12.8. HRMS: Calcd for C$_{11}$H$_{26}$P$_2$O(M$^+$): 236.1459. Found: 236.1448.

Example 27

Synthesis of (Ph)PH(O)CH$_2$CH$_2$P(Ph)$_2$

A suspension of polymer-bound (Ph)PCH$_2$CH$_2$P(Ph)$_2$ (1.5 g, 0.84 mmol/g, 1.26 mmol, prepared using the procedure in Example 5 with phenylMgBr) and H$_2$O (0.5 g, 27.8 mmol) in THF (10 mL) was refluxed overnight before the resin was filtered off and washed with THF (2×5 mL). The filtrate was dried in vacuo to remove the solvent and excess H$_2$O. The resulting residue was 200 mg (47% yield) of (Ph)PH(O)CH$_2$CH$_2$P(Ph)$_2$. It was >95% pure by $^1$H NMR and GC/MS. $^{31}$P NMR (121 MHz, CDCl$_3$, $^1$H-decoupled): δ 28.5 (d, J=46.0 Hz), −11.6 (d, J=46.0 Hz). $^{31}$P NMR (121 MHz, CDCl$_3$, $^1$H-coupled): δ 28.5 (d, J$_{p-H}$=468.9 Hz), −11.6 (s). $^1$H NMR (500 MHz, CDCl$_3$): δ 7.39 (d, J$_{p-H}$=468.9 Hz, 1H), 7.51 (m, 2H), 7.43 (m, 1H), 7.35 (m, 2H), 7.24 (m, 4H), 7.19 (m, 6H), 2.16 (m, 2H), 1.95 (m, 2H). $^{13}$C NMR (125 MHz, CDCl$_3$): δ 135.4, 135.3, 131.2, 130.9, 128.4, 128.3, 127.4, 127.0, 25.0 (d, J$_{p-c}$=65.6 Hz), 17.5. HRMS: Calcd for C$_{20}$H$_{20}$P$_2$O(M$^+$): 338.0989. Found: 338.0979.

Example 28

Synthesis of (3,5-F$_2$H$_3$C$_6$)PH(O)CH$_2$CH$_2$P(3,5-C$_6$H$_3$F$_2$)$_2$

A suspension of polymer-bound (3,5-F$_2$H$_3$C$_6$)PCH$_2$CHP(3,5-C$_6$H$_3$F$_2$)$_2$ (1.0 g, 0.77 mmol/g, 0.77 mmol, prepared using the procedure in Example 5 with (3,5-difluorophenyl)MgBr) and H$_2$O (0.60 g, 33.3 mmol) in THF (10 mL) was refluxed overnight before the resin was filtered off and washed with THF (2×5 mL). The filtrate was dried in vacuo to remove the solvent and excess H$_2$O. The resulting residue was 187 mg (54% yield) of (3,5-C$_6$H$_3$F$_2$)PH(O)CH$_2$CH$_2$P(3,5-C$_6$H$_3$F$_2$)$_2$. It was >95% pure by $^1$H NMR and GC/MS. $^{31}$P NMR (121 MHz, CDCl$_3$, $^1$H-decoupled): δ 24.1 (d, J=47.3 Hz), −8.2 (d, J=47.3 Hz). $^{31}$P NMR (121 MHz, CDCl$_3$, $^1$H-coupled): δ 24.1 (d, J$_{p-H}$=480.6 Hz), −8.2 (s). $^1$H NMR (500 MHz, CDCl$_3$): δ 7.50 (d, J$_{p-H}$=480.6 Hz, 1H), 7.19–7.10 (m, 2H), 6.95 (m, 1H), 6.79 (m, 6H), 2.19–2.10 (m, 2H), 2.0–1.88 (m, 2H). $^{13}$C NMR (125 MHz, CDCl$_3$): δ 164.4, 162.1, 140.3, 134.0, 115.1, 113.0, 108.6, 105.4, 26.0, 18.8. HRMS: Calcd for C$_{20}$H$_{24}$P$_2$OF$_6$(M$^+$): 446.0424. Found: 446.0419.

Example 29

Synthesis of (2,4,6-Me$_3$H$_2$C$_6$)PH(O)CH$_2$CH$_2$P(2,4,6-Me$_3$C$_6$H$_2$)$_2$ A suspension of polymer-bound (2,4,6-Me$_3$H$_2$C$_6$)PCH$_2$CH$_2$P(2,4,6-Me$_3$H$_2$C$_6$)$_2$ (15.0 g, 0.76 mmol/g, 11.4 mmol, prepared using the procedure in Example 5 with (2,4,6-trimethylphenyl)MgBr) and H$_2$O (6.5 g, 361 mmol) in THF (200 mL) was refluxed overnight before the resin was filtered off and washed with THF (2×50 mL). The filtrate was dried in vacuo to remove the solvent and excess H$_2$O. The resulting residue was 2.53 g (48% yield) of (2,4,6-Me$_3$H$_2$C$_6$)PH(O)CH$_2$CH$_2$P(2,4,6-Me$_3$H$_2$C$_6$)$_2$. It was >95% pure by $^1$H NMR and GC/MS. $^{31}$P NMR (121 MHz, CDCl$_3$, $^1$H-decoupled): δ 25.0 (d, J=53.4 Hz), −18.1 (d, J=53.4 Hz). $^{31}$P NMR (121 MHz, CDCl$_3$, $^1$H-coupled): δ 25.0 (d, J$_{p-H}$=470.0 Hz), −18.1 (s). $^{31}$P NMR (121 MHz, C$_6$D$_6$, $^1$H-coupled): δ 20.5 (d, J$_{p-H}$=470.0 Hz), −18.0 (s). $^1$H NMR (500 MHz, C$_6$D$_6$): δ 7.83 (d, J$_{p-H}$=470.0 Hz, 1H), 6.59 (m, 4H), 6.48 (m, 2H), 2.63 (m, 4H), 2.24 (s, 6H), 2.21 (s, 12H), 2.02 (d, J$_{P-C}$=3.96 Hz), 1.93 (s, 3H). $^{13}$C NMR (125 MHz, C$_6$D$_6$): δ 141.9, 141.2, 141.0, 137.4, 136.9, 132.4, 132.2, 129.8, 22.7, 22.5, 20.4, 20.3, 19.2, 19.0. HRMS: Calcd for C$_{29}$H$_{38}$P$_2$O(M$^+$): 464.2398. Found: 464.2395.

Example 30

A suspension of hydroxymethylpolystyrene-bound (i-C$_3$H$_7$)PCH$_2$CH$_2$P(i-C$_3$H$_7$)$_2$ (prepared using the procedure in Example 3, followed by reaction with (i-propyl)MgBr as in Example 5), 1.0 g, 0.68 mmol/g, 0.68 mmol) and H$_2$O (0.4 g, 22.2 mmol) in 8 mL of THF was refluxed for 3 h. The $^{31}$P NMR spectrum of this crude product indicated the presence of (Me$_2$CH)PH(O)CH$_2$CH$_2$P(CHMe$_2$)$_2$ (70%). Removal of solvent and excess H$_2$O afforded 40 mg (25% yield) of the title compound. $^{31}$P NMR (121 MHz, CDCl$_3$, $^1$H-decoupled): δ 46.2 (d, J$_{p-p}$=41.2 Hz), 9.1 (d, J$_{p-p}$=38.2 Hz).

Method B

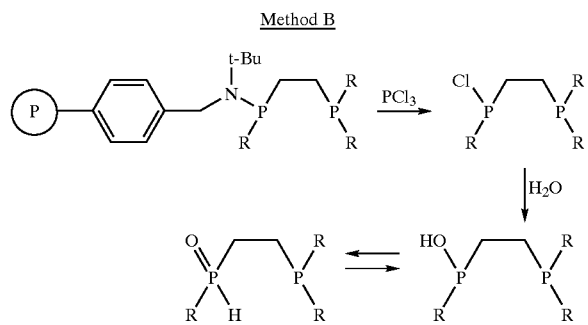

Example 31

A suspension of polymer-bound (C$_6$H$_3$F$_2$)PCH$_2$CH$_2$P (C$_6$H$_3$F$_2$)$_2$ (6.0 g, 0.77 mm/g, 4.6 mmol, prepared using the procedure in Example 5 with (3,5-difluorophenyl)MgBr) and PCl$_3$ (5.0 g, 36.4 mmol) in THF (10 mL) was stirred overnight at room temperature before the resin was filtered off and washed with THF (2×5 mL) and hexane (2×10 mL). The combined filtrates were dried in vacuo to remove the solvent and excess PCl$_3$. The resulting residue was extracted with hexane (3×30 mL). The concentration of the extracts afforded 1.58 g (74%) of the title compound (C$_6$H$_3$F$_2$)(Cl) PCH$_2$CH$_2$P(C$_6$H$_3$F$_2$)$_2$. It was >95% pure by $^1$H NMR and GC/MS. $^{31}$P NMR (202 MHz, CDCl$_3$): δ 90.8 (d, J=29.8 Hz), −9.2 (d, J=29.9 Hz). $^1$H NMR (500 MHz, CDCl$_3$): δ 7.03 (μ, 3H), 6.76 (μ, 6H), 2.02 (μ, 4H), 1.97. $^{13}$C NMR (125 MHz, C$_6$D$_6$): δ 164.1, 162.0, 141.9, 140.9, 115.1, 113.4, 106.3, 105.1, 32.4, 22.0. HRMS: Calcd for C$_{20}$H$_{13}$F$_6$P$_2$Cl: 464.0085. Found: 464.0075.

A solution of 50 mg (0.108 mmol) of (C$_6$H$_3$F$_2$)(Cl) PCH$_2$CH$_2$P(C$_6$H$_3$F$_2$)$_2$ and 0.04 g (2.2 mmol) of H$_2$O in 10 mL of THF was refluxed overnight. After filtration, the solvent and excess H$_2$O were removed in vacuo to give 38 mg (79%) of (C$_6$H$_3$F$_2$)PH(O)CH$_2$CH$_2$P(C$_6$H$_3$F$_2$)$_2$. It was >95% pure by $^1$H NMR and GC/MS. $^{31}$P NMR (121 MHz, CDCl$_3$, $^1$H-decoupled): δ 24.1 (δ, J=47.3 Hz), −8.2 (δ, J=47.3 Hz). $^{31}$P NMR (121 MHz, CDCl$_3$, $^1$H-coupled): δ 24.1 (d, J$_{p-H}$=480.6 Hz), −8.2 (s). $^1$H NMR (500 MHz, CDCl$_3$): δ 7.50 (δ, J$_{p-H}$=480.6 Hz, 1H), 7.19–7.10 (μ, 2H), 6.95 (μ, 1H), 6.79 (μ, 6H), 2.19–2.10 (μ, 2H), 2.0–1.88 (μ, 2H). $^{13}$C NMR (125 MHz, CDCl$_3$): 64.4, 162.1, 140.3, 134.0, 115.1, 113.0, 108.6, 105.4, 26.0, 18.8. HRMS: Calcd for C$_{20}$H$_{24}$P$_2$OF$_6$(M$^+$): 446.0424. Found: 446.0419.

Method C

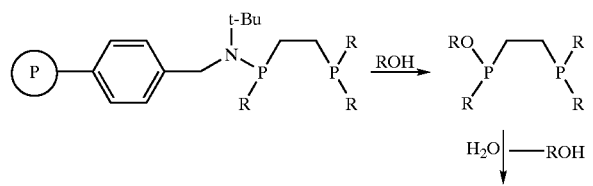

-continued

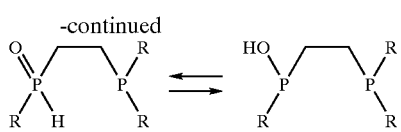

Example 32

A suspension of polymer-bound (CH$_3$CH$_2$CH$_2$) PCH$_2$CH$_2$P (CH$_2$CH$_2$CH$_3$)$_2$ (1.0 g, 0.92 mmol/g, ~0.92 mmol, prepared using the procedure in Example 5 with (n-propyl)MgBr) and MeOH (0.1 g, 3.1 mmol) in THF (5 mL) was refluxed overnight before the resin was filtered off and washed with THF (2×5 mL). The filtrates were dried in vacuo to remove the solvent and excess MeOH. The residue was crude (CH$_3$CH$_2$CH$_2$)P(OMe)CH$_2$CH$_2$P(CH$_2$CH$_2$ CH$_3$)$_2$. It was directly used for next reaction without further purification. $^{31}$P NMR (122 MHz, THF-D$_8$): δ 138.5 (d, J=19.8 Hz), −27.3 (d, J=19.8 Hz). A solution of (CH$_3$CH$_2$CH$_2$)P(OMe)CH$_2$CH$_2$P(CH$_2$CH$_2$CH$_3$)$_2$ above and 0.1 g (5.6 mmol) of H$_2$O in 1.0 mL of THF was stirred overnight at room temperature. The $^{31}$P NMR spectrum of this crude product indicated the presence of (CH$_3$CH$_2$CH$_2$) PH(O)CH$_2$CH$_2$P(CH$_2$CH$_2$CH$_3$)$_2$ (~90%). Removal of solvent and excess H$_2$O afforded 50 mg (23% yield) of the title compound. It was >90% pure by $^1$H NMR and GC/MS. $^{31}$P NMR (121 MHz, THF-D$_8$, $^1$H-decoupled): δ 37.8 (d, J$_{p-p}$= 35.1 Hz), −27.0 (d, J$_{p-p}$=35.1 Hz). $^{31}$P NMR (121 MHz, THF-D$_8$, $^1$H-coupled): δ 37.8 (d, J$_{p-h}$=453.2 Hz), −27.0 (s). $^1$H NMR (500 MHz, CDCl$_3$): δ 6.83 (d, J$_{p-h}$=448.0 Hz, 1H), 1.78 (m, 4H), 1.61 (m, 4H), 1.50 (m, 2H), 1.49–1.35 (m, 6H), 1.02 (t, J=7.2 Hz, 3H), 0.94 (t, J=7.10 Hz, 6H). $^{13}$C NMR (125 MHz, CDCl$_3$): δ 29.5 (d, J$_{p-c}$=65.5 Hz), 28.4, 23.9 (d, J$_{p-c}$=62.8 Hz), 18.3, 17.5, 15.0, 14.8, 14.4. HRMS: Calcd for C$_{11}$H$_{26}$P$_2$O(M$^+$): 236.1459. Found: 236.1428.

Solution Synthesis of Diphosphine Monoxide Ligands

Example 33

A solution of Cl$_2$PCH$_2$CH$_2$PCl$_2$ (1.0 g, 4.3 mmol) in 50 mL of THF was treated with a mixture of Et$_2$NH (0.63 g, 8.6 mmol) in THF (5 mL) dropwise over a period of 10 min. at room temperature. The resulting solution was stirred for 2 h before removal of THF in vacuo. The residue was extracted with hexane (3×30 mL). Removal of the solvents from extracts gave a mixture of Et$_2$NP(Cl)CH$_2$CH$_2$PCl$_2$ [ca. 35% by $^{31}$P NMR, $^{31}$P NMR (121 MHz, CDCl$_3$, $^1$H-decoupled): δ 193.4 (d, J$_{p-p}$=19.8 Hz), 144.6 (δ, J$_{p-p}$=18.4 Hz)], Et$_2$NP (Cl)CH$_2$CH$_2$P(Cl)(NEt$_2$) [ca. 15% by $^{31}$P NMR, $^{31}$P NMR (121 MHz, CDCl$_3$, $^1$H-decoupled): δ 148.5 (s), 148.4 (s)], and unreacted Cl$_2$PCH$_2$CH$_2$PCl$_2$ (ca. 50% by $^{31}$P NMR, $^{31}$P NMR (121 MHz, CDCl$_3$, $^1$H-decoupled): δ 191.4 (s).].

A solution of the mixture above was treated with PhMgCl (3 M solution in THF, 13 mmol) at room temperature over a period of 5 min., and the resulting solution was stirred for 30 min. before 1.0 mL of H$_2$O was used to quench the reaction. After filtration, the solvents were removed in vacuo. The residue was extracted with hexane (3×30 mL). Extracts was dried at reduced pressure to give the compounds which were used directly for the next step without further purification.

A mixture of the compounds above and H$_2$O (1.0 g, 55.5 mmol) in THF (10 mL) was refluxed overnight in a sealed reactor. After filtration, the filtrate was dried in vacuo to give 0.20 g of the residue. The $^{31}$P NMR spectrum of this crude reaction mixture indicated the presence of PhPH(O) CH$_2$CH$_2$PPh$_2$ (<5%), Ph$_2$PCH$_2$CH$_2$PPh$_2$ (ca. 80%) and two compounds (<5%) exhibiting two singlets at δ 27.5, 27.3 ppm.

Synthesis of Polymer-Bound Bisphosphines

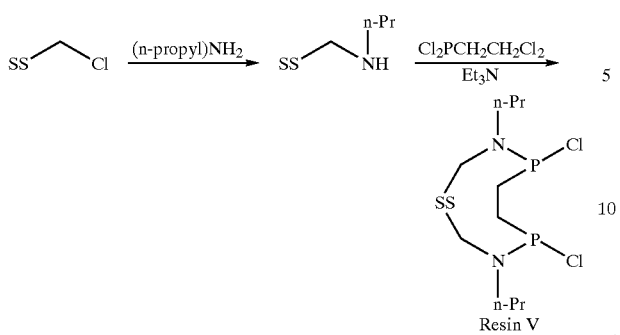

Example 34

A solution of n-propylamine (72 g, 1.22 moles) and KI (0.3 g, 2 mmol) in 800 mL of THF was treated with chloromethylpolystyrene-divinylbenzene (Merrifield resin, 2% DVB, 100 g, 0.72 mmol/g, 72 mmol) while stirring at room temperature for 30 min. The suspension was then refluxed for 24 h before the solution was filtered off. The resulting resin was washed with a mixture of $H_2O$/THF (20% $H_2O$, 3×250 mL), THF (3×150 mL), hexane (3×200 mL). After drying in vacuo overnight, 100 g of the resin were obtained. The disappearance of $^1H$ resonances of polymer-Ph—$CH_2$—Cl ($CH_2$=~4.5 ppm) and the appearance of $^1H$ resonances of polymer-Ph—$CH_2$—$NHCH_2CHMe$ indicates the complete transformation of the chloromethyl groups to n-propylaminomethyl groups.

A solution of resin above (99.0 g, 0.709 mmol/g, 70.1 mmol) in 800 mL of THF was treated slowly with $Cl_2PCH_2CH_2PCl_2$ (7.32 g, 31.58 mmol, 0.45 eq) while stirring at room temperature for a period of 30 min before $Et_3N$ (35.5 g, 350.8 mmol) was added. The resulting suspension was stirred at room temperature overnight before the solution was filtered off. The resin was washed with hexane (2×100 mL), $CH_2Cl_2$ (5×100 mL), and hexane (5×100 mL). The resulting resin was dried in vacuo overnight. $^{31}P$ NMR (122 MHz, $CDCl_3$): δ 148.6 ppm. $^{13}C$ NMR (75 MHz, THF-$d_8$): δ 41.4, 31.9, 22.9, 14.0, 11.7 for polymer-supported groups. Thereafter this will be referred to as Resin V.

A suspension of Resin V above (15.5 g, 0.67 mmol/g, 10.4 mmol) in 250 mL of THF was treated slowly with phenylmagnesium bromide (1.0 M solution in diethylether, 112 mmol). The resulting mixture was stirred at room temperature for 2 h before the solution was filtered off and the resin was washed with THF (3×50 mL), $H_2O$/THF (20% $H_2O$, 2×50 mL), hexane (3×80 mL). The resulting resin was dried in vacuo overnight to afford polymer-bound $PhPCH_2CH_2PPh$. $^{31}P$ NMR (122 MHz, $CDCl_3$): δ 62.4 (s, br.) ppm.

Synthesis of Polymer-bound Bisphosphinites

Example 35

A suspension of Resin V above (2.0 g, 0.99 mmol/g, 1.98 mmol) in 20 mL

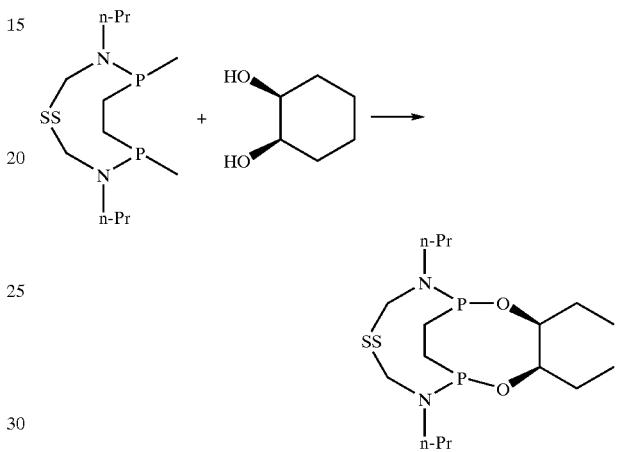

of THF was treated with (1S,2S)-trans-1,2-cyclohexanediol (0.113 g, 0.973 mmol) and $Et_3N$ (1.0 g, 9.9 mmol) over a period of 5 min. The resulting mixture was stirred at room temperature for 2 days before the solution was filtered off and the resin was washed with THF (3×30 mL), hexane (3×30 mL). The resulting resin was dried in vacuo overnight to afford the polymer-bound chiral bisphosphinite. $^{31}P$ NMR (122 MHz, $CDCl_3$): δ 148.2 (s, br.) ppm.

Examples 36A–36M

Examples 36-A to 36-M were prepared using the procedure in Examples 34–35 with the amines, phosphines, and Grignard reagents specified in Table 4A, below. Where no Grignard reagent is specified, the procedure was discontinued at addition of the phosphine.

TABLE 4A

| Ex. | Amine | Phosphine | Grignard | $^{31}P$ NMR |
|---|---|---|---|---|
| 36-A | (n-propyl)$NH_2$ | $Cl_2PCH_2CH_2PCl_2$ | (n-butyl)MgBr | 61.5 |
| 36-B | (n-propyl)$NH_2$ | $Cl_2PCH_2CH_2PCl_2$ | (t-butyl)MgBr | 35.3 |
| 36-C | (n-propyl)$NH_2$ | $Cl_2PCH_2CH_2PCl_2$ | $BrMgCH_2(CH_2)_3CH_2MgBr$ | 35.6 |
| 36-D | (n-propyl)$NH_2$ | $Cl_2PCH_2CH_2PCl_2$ | phenyl$C(CH_3)_2CH_2MgBr$ | 56.2 |
| 36-E | (n-prnpyl)$NH_2$ | $Cl_2PCH_2CH_2PCl_2$ | 4-(t-butyl)phenylMgBr | 61.5 |
| 36-F | (n-propyl)$NH_2$ | $Cl_2PCH_2CH_2PCl_2$ | 2,4,6-trimethylphenylMgBr | 66.0 |
| 36-G | (t-butyl)$NH_2$ | $Cl_2PCH_2CH_2PCl_2$ | none | 149.3 |
| 36-H | (t-butyl)$NH_2$ | $Cl_2PCH_2CH_2PCl_2$ | p-chlorophenylMgBr | 46.8 |
| 36-I | (t-butyl)$NH_2$ | $Cl_2PCH_2CH_2PCl_2$ | phenyl$CH_2CH_2MgBr$ | 49.2 |
| 36-J | (t-butyl)$NH_2$ | $Cl_2PCH_2CH_2PCl_2$ | i-propylMgBr | 62.4 |
| 36-K | (t-butyl)$NH_2$ | $Cl_2PCH_2CH_2PCl_2$ | phenoxyMgBr | 137.1 |
| 36-L | (cyclohexyl)$NH_2$ | $Cl_2PCH_2CH_2PCl_2$ | none | 146.0 |
| 36-M | (cyclohexyl)$NH_2$ | $Cl_2PCH_2CH_2PCl_2$ | $BrMgCH_2(CH_2)_3CH_2MgBr$ | 33.7 |

Cleavage of Bisphosphine Ligands From Resin

Example 37

Synthesis of cis- and trans-PhP(Cl)CH$_2$CH$_2$P(Cl)Ph

A suspension of polymer-bound (Ph)PCH$_2$CH$_2$P(Ph) from Example 34 (14.6 g, 0.29 mmol/g, 4.3 mmol) and PCl$_3$ (5.0 g, 36.4 mmol) in THF (150 mL) was stirred overnight at room temperature before the resin was filtered off and washed with hexane (2×10 mL). Removal of solvents and excess PCl$_3$ from the filtrates by vacuum afforded 1.3 g (96% yield) of cis and trans-mixture of (Ph)P(Cl)CH$_2$CH$_2$P(Cl)(Ph). It was >95% pure by $^1$H NMR. $^{31}$P NMR (121 MHz, CDCl$_3$): δ 93.9 (~45%), 93.3 (~55%) ppm. HRMS: Calcd for C$_{14}$H$_{14}$P$_2$Cl$_2$(M$^+$): 313.9948. Found: 313.9944.

Example 38

Synthesis of cis- and trans-PhP(H)CH)CH$_2$P(H)Ph

A solution of (Ph)P(Cl)CH$_2$CH$_2$P(Cl)(Ph) from Example 37 (cis- and trans-mixture, 1.0 g, 3.17 mmol) in 15 mL of THF was treated slowly with LiAlH$_4$ (1.0 M in THF, 3.17 mmol) over a period of 5 min. The resulting mixture was stirred at room temperature for 2 h before 1.0 g of H$_2$O was added to quench the reaction. After filtration, the filtrate was dried in vacuo, extracted with hexane (3×20 mL). Removal of solvent from extracts gave 290 mg (37%) of cis- and trans-PhP(H)CH$_2$CH$_2$P(H)Ph. $^{31}$P NMR (75 MHz, C$_6$D$_6$, $^1$H-decoupled): δ −45.4 (~40%), −45.8 (~60%) ppm. $^{31}$P NMR (75 MHz, C$_6$D$_6$, $^1$H-coupled): δ −45.4 (d, J$_{p\text{-}H}$=204.5 Hz), −45.8 (d, J$_{p\text{-}H}$=202.9 Hz). HRMS: Calcd for C$_{14}$H$_{16}$P$_2$ (M$^+$): 246.0727. Found: 246.0730.

Example 39

Synthesis of cis- and trans-(2,4,6-Me$_3$C$_6$H$_2$)P(Cl)CH$_2$CH$_2$P(Cl)(2,4,6-Me$_3$C$_6$H$_2$)

The procedure used in Example 34 was used to prepare the title compound using polymer-bound (2,4,6-Me$_3$C$_6$H$_2$)PCH$_2$CH$_2$P(2,4,6-Me$_3$C$_6$H$_2$) from Example 36-F (28.6 g, 0.286 mmol/g, 8.17 mmol) and PCl$_3$ (14.1 g, 130 mmol). After the solvent and excess PCl$_3$ were removed from filtrates in vacuo, 3.05 g (93% yield) of the mixture of cis- and trans-(2,4,6-Me$_3$H$_2$C$_6$)P(Cl)CH$_2$CH$_2$P(Cl)(2,4,6-Me$_3$H$_2$C$_6$) was obtained. It was ~95% pure by $^1$H and $^{31}$P NMR. $^{31}$P NMR (75 MHz, CDCl$_3$): δ 92.3, 91.4 ppm.

A mixture of cis- and trans-(2,4,6-Me$_3$C$_6$H$_2$)P(Cl)CH$_2$CH$_2$P(Cl)(2,4,6-Me$_3$C$_6$H$_2$) (1.0 g, 2.5 mmol) was sublimed at 170° C./10$^{-4}$ torr conditions overnight. 0.25 g (25%) of trans-(2,4,6-Me$_3$C$_6$H$_2$)P(Cl)CH$_2$CH$_2$P(Cl)(2,4,6-Me$_3$C$_6$H$_2$) was obtained. It was >95% pure by $^1$H and $^{31}$P NMR. $^{31}$P NMR (121 MHz, CDCl$_3$): δ 92.0 ppm. $^1$H NMR (500 MHz, CDCl$_3$): δ 6.92 (s, 4H), 2.63 (s, 12H), 2.51 (s, 4H), 2.33 (s, 6H). $^{13}$C NMR (125 MHz, CDCl$_3$): δ 144.4, 141.6, 130.4, 128.6, 28.2, 22.4, 21.0. HRMS: Calcd for C$_{20}$H$_{26}$P$_2$Cl$_2$(M$^+$): 398.0887. Found: 398.0875.

Example 40

Synthesis of cis- and trans-(4-ClC$_6$H$_4$)P(OMe)CH$_2$CH$_2$P(OMe)(4-ClC$_6$H$_4$)

A suspension of polymer-bound (4-ClC$_6$H$_4$)PCH$_2$CH$_2$P(4-ClC$_6$H$_4$) from Example 36-H (1.5 g, 0.408 mmol/g, 0.61 mmol) and MeOH (0.3 g, 9.38 mmol) in 15 mL of THF was refluxed overnight before the resin was filtered off and washed with THF (2×5 mL). After the solvent and excess MeOH were removed from filtrates by vacuum, 112 mg (49% yield) of (4-ClC$_6$H$_4$)P(OMe)CH$_2$CH$_2$P(OMe)(4-ClC$_6$H$_4$) was obtained. It was >95% pure by $^1$H NMR and GC/MS. $^{31}$P NMR (121 MHz, CDCl$_3$): δ 125.7, 125.5 ppm. $^1$H NMR (500 MHz, CDCl$_3$): δ 7.26 (m, 8H), 3.44 (m, 6H, 2CH$_3$), 1.68 (m, 2H), 1.60 (m, 2H). $^{13}$C NMR (125 MHz, CDCl$_3$): δ 141.6, 137.0, 132.9, 132.2, 132.0, 130.9, 130.3, 130.1, 58.3, 29.1. HRMS: Calcd for C$_{16}$H$_{18}$P$_2$O$_2$Cl$_2$(M$^+$): 374.0159. Found: 374.0163.

Example 41

Synthesis of cis- and trans-(MeCH$_2$CH$_2$CH$_2$CH$_2$)P(OMe)CH$_2$CH$_2$P(OMe)(CH$_2$CH$_2$CH$_2$CH$_2$Me)

A suspension of polymer-bound (Cl)PCH$_2$CH$_2$P(Cl) (Resin V, 27.0 g, 0.48 mmol/g, 13.0 mmol) in 200 mL of THF was treated slowly with an excess of ClMg(CH$_2$)$_5$MgCl (0.5 M in THF, 60 mmol) over a period of 10 min. The resulting mixture was stirred at room temperature for 2 h before the solution was filtered off. The resin was washed with THF (3×10 mL), H$_2$O/THF (20% H$_2$O, 2×10 mL), hexane (3×10 mL). The resulting resin was dried in vacuo overnight to afford polymer-bound Me(CH))$_4$PCH$_2$CH$_2$P(CH$_2$)$_4$Me. $^{31}$P NMR (122 MHz, CDCl$_3$): δ 6.15 (s, br.) ppm.

A mixture of polymer-bound Me(CH$_2$)$_4$PCH$_2$CH$_2$P(CH$_2$)$_4$ Me (20 g, 0.476 mmol/g, 9.52 mmol) and MeOH (0.77 g, 24 mmol) in 200 mL of THF was refluxed overnight before the resin was filtered off and washed with THF (2×10 mL). The combined filtrates were concentrated in vacuo to afford 850 mg (30% yield) of the title compounds Me(CH$_2$)$_4$P(OMe)CH$_2$CH$_2$P(OMe)(CH$_2$)$_4$Me. It was >95% pure by $^1$H NMR and GC/MS. $^{31}$P NMR (202 MHz, CDCl$_3$): δ 139.4, 139.1 ppm. $^1$H NMR (500 MHz, CDCl$_3$): δ 3.44 (d, J$_{p\text{-}H}$=10.6 Hz, 6H), 1.78–1.25 (m, 20H), 0.85 (t, J=7.09 Hz, 6H). $^{13}$C NMR (125 MHz, CDCl$_3$): δ 56.7, 33.3, 32.7, 26.1, 23.7, 22.3, 13.8. HRMS: Calcd for C$_{13}$H$_{29}$P$_2$O$_2$(M$^+$−CH$_3$): 279.1643. Found: 279.1616.

Example 42

Synthesis of cis- and trans-(—CH$_2$CH$_2$CH$_2$CH$_2$CH$_2$)PH(O)CH$_2$CH$_2$PH(O)—

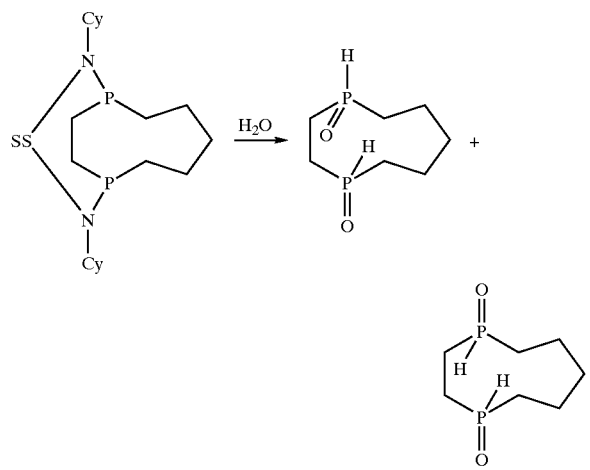

A mixture of polymer-bound (—CH$_2$CH$_2$CH$_2$CH$_2$CH$_2$)PCH$_2$CH$_2$P— (1.0 g, 0.327 mmol/g, 0.327 mmol, from Example 36-M) and H$_2$O (0.5 g, 27.8 mmol) in 5 mL of THF was refluxed overnight before the resin was filtered off and washed with THF (2×5 mL). The combined filtrates were concentrated in vacuo to afford 10 mg (16% yield) of the title compounds. It was >95% pure by $^1$H NMR and GC/MS. $^{31}$P NMR (121 MHz, CDCl$_3$, $^1$H-decoupled): δ 36.0, 35.0 ppm. $^{31}$P NMR (202 MHz, CDCl$_3$, $^1$H-coupled): δ 36.0 (d, $J_{p-H}$=460.1 Hz), 35.0 (d, $J_{p-H}$=457.1 Hz). $^1$H NMR (500 MHz, CDCl$_3$): δ 6.91 (d, $J_{p-H}$=456.4 Hz, 1H), 6.89 (d, $J_{p-H}$=465.4 Hz, 1H), 2.07 (m, 2H), 1.84–1.76 (m, 3H), 1.57 (m, 2H), 1.37–1.26 (m, 5H), 0.84 (t, J=7.21 Hz, 2H). $^{13}$C NMR (75 MHz, CDCl$_3$): δ 32.7 (t, J=7.0 Hz), 22.1, 21.3, 13.7. HRMS: Calcd. for C$_7$H$_{15}$P$_2$O$_2$(M$^+$-H): 193.0547. Found: 193.0557.

Example 43

Synthesis of cis-and trans-(—CH$_2$CH$_2$CH$_2$CH$_2$CH$_2$)P(OMe)CH$_2$CH$_2$P(OMe)—

A mixture of polymer-bound (—CH$_2$CH$_2$CH$_2$CH$_2$CH$_2$)PCH$_2$CH$_2$P— (0.5 g, 0.44 mmol/g, 0.22 mmol) and MeOH (0.20 g, 6.3 mmol) in 5 mL of THF was refluxed overnight before the resin was filtered off and washed with THF (2×5 mL). The combined filtrates were concentrated in vacuo to afford 10 mg (21% yield) of the title compounds. $^{31}$P NMR (121 MHz, CDCl$_3$): δ 137.6, 137.4 ppm. HRMS: Calcd. for C$_9$H$_{20}$P$_2$O$_2$(M$^+$): 222.0939. Found: 222.0909.

Example 44

Synthesis of [(1S,2S)-trans-1,2-C$_6$H$_{10}$O$_2$]P(Cl)CH$_2$CH$_2$P(Cl)—

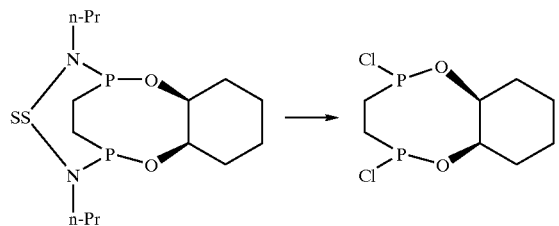

A mixture of polymer-bound [(1S,2S)-trans-1,2-OCHCH$_2$CH$_2$CH$_2$CH$_2$CHO)PCH$_2$CH$_2$P— from Example 35 (0.5 g, 0.48 mmol/g, 0.24 mmol) and PCl$_3$ (0.50 g, 3.64 mmol) in 5 mL of THF was stirred at room temperature overnight before the resin was filtered off and washed with THF (2×5 mL). The combined filtrates were concentrated in vacuo to afford 23 mg (35% yield) of the title compounds. $^{31}$P NMR (121 MHz, CDCl$_3$): δ 190.9 ppm.

Example 45

Synthesis of (PhCH$_2$CH$_2$)PH(O)CH$_2$CH$_2$PH(O)(CH$_2$CH$_2$Ph)

A mixture of polymer-bound (PhCH$_2$CH$_2$)PCH$_2$CH$_2$P(CH$_2$CH$_2$Ph) (1.5 g, 0.45 mmol/g, 0.675 mmol, from Example 36-1) and H$_2$O (0.5 g, 27.8 mmol) in 5 mL of THF was refluxed overnight before the resin was filtered off and washed with THF (2×5 mL). The combined filtrates were concentrated in vacuo to afford 65 mg (29% yield) of the title compounds. It was >95% pure by $^1$H NMR and GC/MS. $^{31}$P NMR (202 MHz, CDCl$_3$, $^1$H-decoupled): δ 34.0 ppm. $^{31}$P NMR (202 MHz, CDCl$_3$, $^1$H-coupled) δ 34.0 (d, $J_{p-H}$=465.4 Hz). $^1$H NMR (500 MHz, CDCl$_3$): δ 7.2–7.1 (m, 10H), 6.87 (d, $J_{p-H}$=465.4 Hz, 2H), 2.96–2.87 (m, 4H), 2.18–1.97 (m, 8H). $^{13}$C NMR (125 MHz, CDCl$_3$): δ 139.6, 128.8, 128.1, 126.8, 29.6, 27.7, 20.8. HRMS: Calcd. for C$_{18}$H$_{24}$P$_2$O$_2$(M$^+$): 334.1252. Found: 334.1243.

Example 46

Synthesis of cis- and trans-(PhO)P(Ph)CH$_2$CH$_2$P(Ph)(PhO)

A suspension of polymer-bound (Ph)PCH$_2$CH$_2$P(Ph) from Example 34 (2.0 g, 0.456 mmol/g, 0.913 mmol) and PhOH (0.152 g. 1.615 mmol) in 5 mL of THF was refluxed overnight before the resin was filtered off and washed with THF (2×10 mL). The combined filtrates were concentrated in vacuo to afford 126 mg (36% yield) of the title compounds (Ph)P(OPh)CH$_2$CH$_2$P(OPh)(Ph). It was >95% pure by $^1$H NMR and GC/MS. $^{31}$P NMR (202 MHz, CDCl$_3$): δ 121.8, 121.4 ppm. $^1$H NMR (500 MHz, CDCl$_3$): δ 7.71–6.99 (m, 20H), 2.34–2.18 (m, 4H). $^{13}$C NMR (125 MHz, CDCl$_3$): δ 157.0, 140.9, 129.9, 129.6, 128.7, 122.5, 120.2, 118.8, 115.7, 28.9. HRMS: Calcd. for C$_{26}$H$_{24}$P$_2$O$_2$(M$^+$): 430.1252. Found: 430.1282.

Example 47

Synthesis of cis- and trans-[3,5-(CF$_3$)$_2$C$_6$H$_3$O]P(CH$_2$CMe$_2$Ph)CH$_2$CH$_2$P[3,5-(CF$_3$)$_2$C$_6$H$_3$O](CH$_2$CMe$_2$Ph)$_2$ A suspension of polymer-bound (PhCMe$_2$CH$_2$)PCH$_2$CH$_2$P(CH$_2$CMe$_2$Ph)$_2$ from Example 36-D (10.0 g, 0.317 mmol/g, 3.17 mmol) and 3,5-(CF$_3$)$_2$C$_6$H$_3$OH (1.10 g, 4.78 mmol) in THF (100 mL) was refluxed overnight before the resin was filtered off and washed with THF (2×10 mL). The filtrates were dried in vacuo to give 1.2 g (62% yield) of the title compounds. It was >95% pure by $^1$H NMR and GC/MS. $^{31}$P NMR (121 MHz, C$_6$D$_6$): δ 136.3, 135.3 ppm. $^1$H NMR (500 MHz, C$_6$D$_6$): δ 7.40–6.84 (m, 16H), 2.15 (m, 1H), 1.60 (m, 1H), 1.52 (m, 1H), 1.36–1.21 (m, 17H). $^{13}$C NMR (125 MHz, C$_6$D$_6$): δ 158.9, 147.8, 133.2, 133.1, 132.9, 126.6, 126.2, 125.0, 122.8, 118.7, 116.6, 115.5, 51.0, 37.1, 31.6, 29.8, 29.7, 28.1. HRMS: Calcd. for C$_{38}$H$_{36}$P$_2$O$_2$F$_{12}$ (M$^+$): 814.1999. Found: 814.1954.

Example 48

Synthesis of cis- and trans-(CH$_3$CH$_2$CH$_2$S)P(Ph)CH$_2$CH$_2$P(Ph)(SCH$_2$CH$_2$CH$_3$)

A suspension of polymer-bound (Ph)PCH$_2$CH$_2$P(Ph) from Example 34 (20.0 g, 0.456 mmol/g, 9.13 mmol) and CH$_3$CH$_2$CH$_2$SH (1.83 g, 23.6 mmol) in THF (200 mL) was refluxed overnight before the resin was filtered off and washed with THF (2×20 mL). The filtrates were dried in vacuo to remove the solvent and excess CH$_3$CH$_2$CH$_2$SH. The resulting residue was 2.69 g (78% yield) of the title compounds. It was >95% pure by $^1$H NMR and GC/MS. $^{31}$P NMR (202 MHz, C$_6$D$_6$): δ 29.55, 29.52 ppm. $^1$H NMR (500 MHz, C$_6$D$_6$): δ 7.57 (m, 4H), 7.08–7.03 (m, 6H), 2.46 (m, 4H), 2.20 (m, 4H), 1.47 (m, 4H), 0.75 (t, J=7.13 Hz, 6H). $^{13}$C NMR (125 MHz, C$_6$D$_6$): δ 138.1, 130.5, 127.6, 126.7, 34.0, 26.0 (m, $J_{P-C}$=8.75 Hz), 24.1, 12.0. HRMS: Calcd. for C$_{20}$H$_{29}$P$_2$S$_2$(M$^+$+H): 395.1186. Found: 395.1107.

Example 49

Preparation of Dichloro[cis and trans-1,2-bis[(1-propylthio)-(1-phenyl)phosphino]ethane] Palladium(II)

A solution of (CH$_3$CH$_2$CH$_2$S)P(Ph)CH$_2$CH)P(Ph)(SCH$_2$CH$_2$CH$_3$) from Example 106 (cis/trans 50%, 0.300 g, 0.76 mmol) in 20 mL of $CH_2Cl_2$ was added dropwise to a solution of $PdCl_2(COD)$ (0.217 g, 0.76 mmol) in 25 mL of $CH_2Cl_2$ at room temperature and the solution was stirred overnight. The resulting reaction mixture was concentrated in vacuo to give solid compounds. After washed with hexane (2×5 mL) and dried in vacuo, 0.40 g (92% yield) of the title compounds were obtained. Recrystallization from dichloromethane/hexane (1:1 volume ratio) gives the Dichloro[trans-1,2-bis[(1-propylthio)-(1-phenyl)phosphino]ethane]Palladium(II) as yellow crystals. The molecular structure of [trans-$(CH_3CH_2CH_2S)P(Ph)CH_2CH_2P(Ph)$ $(SCH_2CH_2CH_3)][PdCl_2]$ has been determined by X-ray diffraction. [trans-$(CH_3CH_2CH_2S)P(Ph)CH_2CH_2P(Ph)$ $(SCH_2CH_2CH_3)][PdCl_2]$ is triclinic, P-1 (No. 2), a=11.414(2) Å, b=12.952(2) Å, c=8.221(1) Å, alpha=92.75(1)°, beta=97.25(1)°, gamma=98.10(1)°, T=−100° C., Vol=1190.9 Å$^3$, Z=2, Formula weight=571.83, Density=1.594 g/cc, $\mu$(Mo)=13.02 cm$^{-1}$. Anal. Calcd. for $C_{20}H_{28}P_2S_2PdCl_2$: C, 42.01; H, 4.94; Cl, 12.40. Found: C, 42.55; H, 4.57; Cl, 11.82.

Synthesis of Polymer-bound Monophosphines

Example 50

A solution of $PCl_3$ (26 g, 189 mmol) in 400 mL of THF was treated slowly with Resin I (25 g, 1.21 mmol/g, 30.3 mmol) while stirring at room temperature for a period of 30 min. before $Et_3N$ (16 g, 157.5 mmol) was added. The resulting suspension was stirred at room temperature overnight before the solution was filtered off. The resin was washed with hexane (2×50 mL), $CH_2Cl_2$ (5×80 mL), and hexane (5×30 mL). The resulting resin was dried in vacuo overnight. $^{31}$P NMR (122 MHz, $CDCl_3$): δ 179.1 ppm.

A suspension of the resin above (5.0 g, 1.12 mmol/g, 5.6 mmol) in 150 mL of THF was treated slowly with phenylmagnesium bromide (2 M solution in diethylether, 64 mmol). The resulting mixture was stirred at room temperature for 30 min. before the solution was filtered off and the resin was washed with THF (3×50 mL), $Me_2CHOH$/THF (20% $Me_2CHOH$, 10 mL), hexane (3×30 mL). The resulting resin was dried in vacuo overnight to afford polymer-bound $PPh_2$. $^{31}$P NMR (122 MHz, $CDCl_3$): δ 52.3 ppm.

Example 51

A solution of $Cl_2PPh$ (33.8 g, 189 mmol) and $Et_3N$ (16.0 g, 157.5 mmol) in 500 mL of THF was treated slowly with Resin I (25.0 g, 1.21 mmol/g, 30.3 mmol) while stirring at room temperature for a period of 10 min. The resulting suspension was stirred at room temperature overnight before the solution was filtered off. The resin was washed with THF (50 mL), hexane (3×50 mL), $CH_2Cl_2$ (4×50 mL), and hexane (2×50 mL). The resulting resin was dried in vacuo overnight. $^{31}$P NMR (122 MHz, $CDCl_3$): δ 135.4 ppm.

A suspension of the resin (5.0 g, 1.03 mmol/g, 5.2 mmol) in 150 mL of THF was treated slowly with i-propylmagnesium chloride (0.5 M solution in diethylether, 32.0 mmol). The resulting mixture was stirred at room temperature for 2 h before the solution was filtered off and the resin was washed with THF (3×10 mL), $Me_2CHOH$/THF (20% $Me_2CHOH$, 5 mL), hexane (3×30 mL). The resulting resin was dried in vacuo overnight to afford polymer-bound (i-$C_3H_7$)PPh. $^{31}$P NMR (122 MHz, $CDCl_3$): δ 55.5 ppm.

Example 52

Example 52 was performed using the same techniques described in Examples 50 and 51. Results are shown in Table 5A below.

TABLE 5A $$S-L-Z-P\begin{array}{c}R_1\\R_2\end{array}$$

| | L | Z | $R_1$ | $R_2$ | $^{31}$P NMR |
|---|---|---|---|---|---|
| 52-A | —$CH_2$— | -N(n-propyl)- | allyl | allyl | 56.9 |
| 52-B | —$CH_2$— | -N(n-propyl)- | allyl | phenyl | 59.4 |
| 52-C | —$CH_2$— | -N(n-propyl)- | chloro | chloro | 161.5 |
| 52-D | —$CH_2$— | -N(n-propyl)- | chloro | phenyl | 140.3 |
| 52-E | —$CH_2$— | -N(n-propyl)- | phenyl | vinyl | 60.7 |
| 52-F | —$CH_2$— | -N(n-propyl)- | vinyl | vinyl | 56.1 |
| 52-G | —$CH_2$— | -N(phenyl)- | chloro | chloro | 156.6 |
| 52-H | —$CH_2$— | -N(phenyl)- | chloro | ethyl | 149.8 |
| 52-I | —$CH_2$— | -N(phenyl)- | cyclohexyl | cyclohexyl | 75.2 |
| 52-J | —$CH_2$— | -N(phenyl)- | chloro | phenyl | 133.4 |
| 52-K | —$CH_2$— | -N(phenyl)- | isopropyl | isopropyl | 84.5 |
| 52-L | —$CH_2$— | -N(t-butyl)- | allyl | phenyl | 44.9 |
| 52-M | —$CH_2$— | -N(t-butyl)- | chloro | chloro | 179.1 |
| 52-N | —$CH_2$— | -N(t-butyl)- | chloro | phenyl | 135.4 |
| 52-O | —$CH_2$— | -N(t-butyl)- | ethyl | phenyl | 48.4 |
| 52-P | —$CH_2$— | -N(t-butyl)- | isopropyl | isopropyl | 70.4 |
| 52-Q | —$CH_2$— | -N(t-butyl)- | mesityl | mesityl | 32.9 |
| 52-R | —$CH_2$— | -N(t-butyl)- | mesityl | phenyl | 42.7 |
| 52-S | —$CH_2$— | -N(t-butyl)- | phenyl | vinyl | 47.8 |
| 52-T | —$CH_2$— | -N(t-butyl)- | vinyl | vinyl | 43.8 |
| 52-U | —$CH_2$— | -N(t-butyl)- | H | phenyl | 14.5 |

Cleavage of Ligands From the Polymer-Supported Monophosphines

Example 53

Synthesis of $ClPPh_2$

A suspension of polymer-bound $PPh_2$ from Example 50 (1.25 g, 0.98 mmol/g, 1.23 mmol) and $PCl_3$ (0.66 g, 4.8 mmol) in THF (10 mL) was stirred overnight at room temperature before the resin was filtered off and washed with THF (2×10 mL). Removal of solvents and excess $PCl_3$ from the filtrates by vacuum afforded 110 mg (41% yield) of crude $ClPPh_2$, of which the $^1$H, $^{13}$C and $^{31}$P NMR spectra obtained matched exactly those for authentic sample. $^{31}$P NMR (121 MHz, $CDCl_3$): δ 83.4 ppm. $^1$H NMR (500 MHz, $CDCl_3$): δ 7.49–7.46 (m, 4H), 7.31–7.26 (m, 6H). $^{13}$C NMR (125 MHz, $CDCl_3$): δ 138.8 (d, $J_{p-c}$=32.6 Hz), 131.7 (d, $J_{p-c}$=24.5 Hz), 130.4, 128.6 (d, $J_{p-c}$=6.91 Hz). HRMS: Calcd. for $C_{12}H_{10}PCl(M^+)$: 220.0209. Found: 220.0216.

Example 54

Synthesis of $ClPCy_2$

A suspension of polymer-bound $PCy_2$ from Example 52 (1.0 g, 1.1 mmol/g, 1.1 mmol) and $PCl_3$ (0.66 g, 4.8 mmol) in THF (10 mL) was stirred overnight at room temperature before the resin was filtered off and washed with THF (2×5 mL). Removal of solvents and excess $PCl_3$ from the filtrates by vacuum afforded 208 mg (82% yield) of crude $ClPCy_2$, of which the $^1$H, $^{13}$C and $^{31}$P NMR spectra obtained matched exactly those for authentic sample. $^{31}$P NMR (121 MHz, $CDCl_3$): δ 128.8 ppm. $^1$H NMR (500 MHz, $CDCl_3$): δ 1.74 (m, 12H), 1.20,(m, 10H). $^{13}$C NMR (125 MHz, $CDCl_3$): δ 38.4 (d, $J_{p-c}$=31.4Hz), 27.8 (d, $J_{p-c}$=11.5 Hz), 26.9 (d, $J_{p-c}$=9.53 Hz), 26.4.

Example 55

Synthesis of $CH_3CH_2CH_2SPPh_2$

A suspension of polymer-bound $PPh_2$ from Example 50 (1.25 g, 0.98 mmol/g, 1.23 mmol) and $CH_3CH_2CH_2SH$ (0.37 g, 4.8 mmol) in THF (10 mL) was refluxed overnight in a sealed reactor before the resin was filtered off and washed with THF (2×10 mL). After the solvent and excess $CH_3CH_2CH_2SH$ were removed from filtrates by vacuum, 200 mg (62% yield) of $CH_3CH_2CH_2SPPh_2$ was obtained. It was >95% pure by $^1H$ NMR and GC/MS. $^{31}P$ NMR (202 MHz, $CDCl_3$): δ 28.8 ppm. $^1H$ NMR (500 MHz, $CDCl_3$): δ 7.45 (m, 4H), 7.21 (m, 6H), 2.62 (m, 2H), 1.59 (m, 2H), 0.86 (t, J=7.24 Hz, 3H). $^{13}C$ NMR (125 MHz, $CDCl_3$): δ 138.3, 132.4, 129.1, 128.3, 35.7, 25.0, 13.2. HRMS: Calcd. for $C_{15}H_{17}PS(M^+)$: 260.0789. Found: 260.0793.

Example 56

Synthesis of $ClP(Ph)CH=CH_2$

A suspension of polymer-bound $P(Ph)CH=CH_2$ from Example 52-E (1.0 g, 0.94 mmol/g, 0.94 mmol) and $PCl_3$ (0.66 g, 4.8 mmol) in THF (10 mL) was stirred overnight at room temperature before the resin was filtered off and washed with THF (2×10 mL). Removal of solvents and excess $PCl_3$ from the filtrates by vacuum afforded 127 mg (79% yield) of crude $ClP(Ph)CH=CH_2$. $^{31}P$ NMR (121 MHz, $CDCl_3$): δ 79.9 ppm. $^1H$ NMR (500 MHz, $CDCl_3$): δ 7.59–7.35 (m, 5H), 6.58 (m, 1H), 5.91 (m, 2H). $^{13}C$ NMR (125 MHz, $CDCl_3$): δ 139.3, 138.3, 131.7, 130.9, 130.0, 128.9. HRMS: Calcd. for $C_8H_8PCl(M^+)$: 170.0052. Found: 170.0041.

Example 57

Synthesis of $EtOP(CHMe_2)$

A suspension of polymer-bound $P(CHMe_2)_2$ from Example 51 (1.25 g, 1.06 mmol/g, 1.32 mmol, $^{31}P$ NMR (121 MHz, $CDCl_3$): δ 70.4 ppm) and EtOH (0.22 g, 4.8 mmol) in THF (10 mL) was refluxed overnight before the resin was filtered off and washed with THF (2×10 mL). After the solvents were removed from filtrates by vacuum, 55 mg (26% yield) of $EtOP(CHMe_2)$ was obtained. It was >95% pure by $^1H$ NMR and GC/MS. $^{31}P$ NMR (202 MHz, $CDCl_3$): δ 151.4 ppm. $^1H$ NMR (500 MHz, $CDCl_3$): δ 3.71 (m, 2H), 1.15 (m, 3H), 1.00 (m, 12H). $^{13}C$ NMR (125 MHz, $CDCl_3$): δ 67.9, 27.8, 17.7, 16.9. HRMS: Calcd. for $C_8H_{19}PO(M^+)$: 162.1174. Found: 162.1175.

Example 58

Synthesis of $CH_3CH_2CH_2SP(CHMe_2)_2$

An analogous procedure to that for $EtOP(CHMe_2)$ was used for the synthesis of title compound using polymer-bound $P(CHMe_2)_2$ from Example 51 (1.25 g, 1.06 mmol/g, 1.32 mmol) and $CH_3CH_2CH_2SH$ (0.37 g, 4.8 mmol). After the solvents were removed from filtrates by vacuum, 250 mg (98% yield) of $CH_3CH_2CH_2SP(CHMe_2)$ was obtained. It was >95% pure by $^1H$ NMR and GC/MS. $^{31}P$ NMR (202 MHz, $CDCl_3$): δ 65.7 ppm. $^1H$ NMR (500 MHz, $CDCl_3$): δ 2.48 (m, 2H), 1.81 (m, 2H), 1.59 (m, 2H), 1.07 (m, 12H), 0.90 (t, J=7.33 Hz, 3H). $^{13}C$ NMR (125 MHz, $CDCl_3$): δ 36.3, 25.1, 19.2, 18.2, 12.9.

Example 59

Synthesis of $(Me_2CH)PH(O)(CHMe_2)$

A suspension of polymer-bound $P(CHMe_2)_2$ from Example 51 (1.25 g, 1.06 mmol/g, 1.32 mmol) and $H_2O$ (0.1 g, 4.8 mmol) in THF (10 mL) was refluxed overnight before the resin was filtered off and washed with THF (2×5 mL). The filtrate was dried in vacuo to remove the solvent and excess $H_2O$. The resulting residue was 50 mg (28% yield) of $(Me_2CH)PH(O)(CHMe_2)$. It was >95% pure by $^1H$ NMR and GC/MS. $^{31}P$ NMR (121 MHz, $CDCl_3$, $^1H$-decoupled): δ 56.9 ppm. $^{31}P$ NMR (121 MHz, $CDCl_3$, $^1H$-coupled): δ 24.1 (d, $J_{P-H}$=429.7 Hz). $^1H$ NMR (500 MHz, $CDCl_3$): δ 6.30 (d, $J_{P-H}$=434.1 Hz, 1H), 1.92 (m, 2H), 1.15 (m, 12H). $^{13}C$ NMR (125 MHz, $CDCl_3$): δ 25.0 (d, $J_{P-C}$=63.9 Hz), 16.0, 14.8. HRMS: Calcd. for $C_6H_{15}PO(M^+)$: 134.0861. Found: 134.0856.

Example 60

Synthesis of $CH_3CH_2CH_2SP(Ph)(2,4,6-Me_3H_2C_6)$

A suspension of polymer-bound $PPh(2,4,6-Me_3H_2C_6)$ from Example 52-R (1.25 g, 0.95 mmol/g, 1.18 mmol, $^{31}P$ NMR (121 MHz, $CDCl_3$): δ 42.7 ppm) and $CH_3CH_2CH_2SH$ (0.37 g, 4.8 mmol) in THF (10 mL) was refluxed overnight before the resin was filtered off and washed with THF (2×5 mL). The filtrate was dried in vacuo to remove the solvent and excess $CH_3CH_2CH_2SH$. The resulting residue was 350 mg (98% yield) of $CH_3CH_2CH_2SP(Ph)(2,4,6-Me_3H_2C_6)$. It was >95% pure by $^1H$ NMR and GC/MS. $^{31}P$ NMR (121 MHz, $CDCl_3$): δ 20.6 ppm. $^1H$ NMR (500 MHz, $CDCl_3$): δ 7.31 (m, 2H), 7.13 (m, 3H), 6.79 (s, 2H), 2.72 (m, 2H), 2.26 (s, 6H), 2.17 (s, 3H), 1.67 (m, 2H), 0.92 (t, J=7.31 Hz, 3H). $^{13}C$ NMR (125 MHz, $CDCl_3$): δ 144.0, 140.9, 140.2, 132.0, 129.7, 129.4, 128.2, 127.1, 38.0, 25.5, 23.3, 21.2, 13.4. Calcd for $C_{18}H_{23}Ps(M^+)$: 302.1258. Found: 302.1266.

Example 61

Synthesis of $(2,4,6-Me_3H_2C_6)PH(O)(Ph)$

Scale-up preparation was carried out using the following procedure. A suspension of polymer-bound P(Ph)Cl from Example 52 (15.0 g, 1.03 mmol/g, 15.4 mmol) in 200 mL of THF was treated with $Me_3C_6H_2MgCl$ (98 mmol, 2M solution in THF) over a period of 10 min. The resulting mixture was stirred for an additional 2 h at ambient temperature before the solution was filtered off and the resin was washed with THF (3×20 mL), Hexane (3×20 mL), MeCHOH (2×15 mL), Hexane (2×20 mL). A suspension of the resin above (ca. 15 g) and $H_2O$ (3.6 g, 200 mmol) in 200 of THF was refluxed overnight. The mixture was cooled to room temperature, and the resulting resin was filtered off and washed with Hexane (2×20 mL). The filtrates were evaporated to dryness and the residue was sublimed at 150° C./$10^{-4}$ torr conditions to afford 2.0 g (53% yield) of the title compound. $^{31}P$ NMR (121 MHz, $CDCl_3$, $^1H$-decoupled): δ 18.0. $^{31}P$ NMR (121 MHz, $CDCl_3$, $^1H$-coupled): δ 18.0 (d, $J_{P-H}$=512.1 Hz). $^1H$ NMR (500 MHz, $CDCl_3$): δ 8.55 (d, $J_{P-H}$=512.1 Hz, 1H), 7.57 (m, 2H), 7.48 (m, 1H), 7.35 (m, 2H), 6.80 (d, $J_{P-C}$=4.0 Hz, 2H), 2.29 (s, 6H), 2.23 (s, 3H). $^{13}C$ NMR (125 MHz, $CDCl_3$): δ 144.8, 143.3, 133.5, 131.5, 131.0, 129.5, 128.0, 120.7, 22.1, 21.9. HRMS: Calcd. for $C_{15}H_{17}PO(M^+)$: 244.1017. Found: 244.1015. Anal. Calcd. for $C_9H_{13}PO$: C, 73.76; H, 7.01; P, 12.68. Found: C, 73.66; H, 6.92; P, 12.70.

Example 62

Synthesis of $CH_3CH_2CH_2SP(Ph)(CHMe_2)$

A suspension of polymer-bound $PPh(CHMe_2)$ from Example 51 (1.25 g, 1.02 mmol/g, 1.28 mmol, $^{31}P$ NMR (121 MHz, $CDCl_3$): δ 55.5 ppm) and $CH_3CH_2CH_2SH$ (0.37 g, 4.8 mmol) in THF (10 mL) was refluxed overnight before the resin was filtered off and washed with THF (2×5 mL). The filtrate was dried in vacuo to remove the solvent and excess $CH_3CH_2CH_2SH$. The resulting residue was 280 mg (97% yield) of $CH_3CH_2CH_2SP(Ph)(CHMe_2)$. It was >95% pure by $^1H$ NMR and GC/MS. $^{31}P$ NMR (121 MHz, $CDCl_3$): δ 45.2 ppm. $^1H$ NMR (500 MHz, $CDCl_3$): δ 7.55 (m, 2H), 7.28 (m, 3H), 2.58 (m, 2H), 1.99 (m, 1H), 1.58 (m, 2H), 1.04 (m, 2H), 0.97–0.81 (m, 9H). $^{13}C$ NMR (125 MHz, $CDCl_3$): δ 138.1, 132.0, 131.1, 128.2, 35.6, 34.5, 29.6, 19.0, 13.0. Calcd. for $C_{12}H_{19}PSO(MO^+)$: 242.0894. Found: 242.0883.

Example 63

Synthesis of $(Me_2CH)PH(O)(Ph)$

A suspension of polymer-bound $PPh(CHMe_2)$ from Example 51 (1.25 g, 1.02 mmol/g, 1.28 mmol, $^{31}P$ NMR (121 MHz, $CDCl_3$): δ 55.5 ppm) and $H_2O$ (0.1 g, 4.8 mmol) in THF (10 mL) was refluxed overnight before the resin was filtered off and washed with THF (2×5 mL). The filtrate was dried in vacuo to remove the solvent and excess $H_2O$. The resulting residue was 80 mg (37% yield) of $(Me_2CH)PH(O)$ (Ph). It was >95% pure by $^1H$ NMR and GC/MS. $^{31}P$ NMR (121 MHz, $CDCl_3$, $^1H$-decoupled): δ 47.8. 31P NMR (121 MHz, $CDCl_3$, $^1H$-coupled): δ 47.8 (d, $J_{P-H}$=487.7 Hz). $^1H$ NMR (500 MHz, $CDCl_3$): δ 7.44–7.53 (m, 5H), 7.25 (d, $J_{P-H}$=487.5 Hz, 1H), 2.33 (m, 1H), 1.12 (m, 6H). $^{13}C$ NMR (125 MHz, $CDCl_3$): δ 133.8, 131.1, 129.4, 125.4, 28.0, 14.7. HRMS: Calcd for $C_9H_{13}PO(M^+)$: 168.0704. Found: 168.0704.

Synthesis of Polymer-bound Bidentate Ligands

Example 64

Polymer-bound $P(Ph)CH_2CH_2P(Ph)_2$

A suspension of polymer-bound $P(Ph)CH=CH_2$ from Example 52-E (1.0 g, 0.94 mmol), $Ph_2PH$ (2.1 g, 11.3 mmol) and NaO-tBu (0.1 g, 1.0 mmol) in 10 mL of THF was refluxed overnight before the solution was filtered off. The resulting resin was washed with hexane (2×50 mL), $CH_2Cl_2$ (5×80 mL), $Me_2CHOH$ (2×5 mL) and hexane (5×30 mL). The resin was dried in vacuo overnight. $^{31}P$ NMR (122 MHz, $CDCl_3$): δ 62.7, −11.3 ppm.

Example 65

Polymer-bound $P(Ph)CH_2CH_2P(Ph)Me$

A suspension of polymer-bound $P(Ph)CH=CH_2$ from Example 52-S (1.7 g, 1.76 mmol, 1.04 mm/g), Ph(Me)PH (2.0 g, 14.5 mmol) and NaO-tBu (0.1 g, 1.0 mmol) in 10 mL of THF was refluxed overnight before the solution was filtered off. The resulting resin was washed with hexane (2×50 mL), $CH_2Cl_2$ (5×80 mL), $Me_2CHOH$ (2×5 mL) and hexane (5×30 mL). The resin was dried in vacuo overnight. $^{31}P$ NMR (122 MHz, $CDCl_3$): δ 45.8, −31.7 ppm.

Example 66

Polymer-bound 1-P(Ph)-2-$C_6H_4$OMe

A suspension of polymer-bound P(Ph)Cl from Example 52-D (2.0 g, 1.86 mmol, 0.93 mm/g), and 1,2-$MeOC_6H_4MgBr$ (15.0 mmol, 0.5 M in THF solution) in 10 mL of THF was refluxed over 2 h before the solution was filtered off. The resulting resin was washed with hexane (2×10 mL), $CH_2Cl_2$ (5×10 mL), $Me_2CHOH$ (5 mL) and hexane (5×10 mL). The resin was dried in vacuo overnight. $^{31}P$ NMR (122 MHz, $CDCl_3$): δ 57.3 ppm.

Example 67

Polymer-bound 1-P(Ph)-2,4-$C_6H_3(OMe)_2$

A suspension of polymer-bound P(Ph)Cl Example 52-D (2.0 g, 1.86 mmol, 0.93 mm/g), and 1,2,4-$(MeO)_2C_6H_3MgBr$ (15.0 mmol, 0.5 M in THF solution) in 10 mL of THF was refluxed over 2 h before the solution was filtered off. The resulting resin was washed with hexane (2×10 mL), $CH_2Cl_2$ (5×10 mL), $Me_2CHOH$ (5 mL) and hexane (5×10 mL). The resin was dried in vacuo overnight. $^{31}P$ NMR (122 MHz, $CDCl_3$): δ 56.1 ppm.

Example 68

Polymer-bound 1-P(Ph)-3-$C_6H_4$OMe

A suspension of polymer-bound P(Ph)Cl Example 52-N (0.8 g, 0.88 mmol, 0.95 mm/g), and 1,3-$MeOC_6H_4MgBr$ (4.0 mmol, 0.5 M in THF solution) in 10 mL of THF was stirred at room temperature over 2 h before the solution was filtered off. The resulting resin was washed with hexane (2×10 mL), $CH_2Cl_2$ (5×10 mL), $Me_2CHOH$ (5 mL) and hexane (5×10 mL). The resin was dried in vacuo overnight. $^{31}P$ NMR (122 MHz, $CDCl_3$): δ 52.8 ppm.

Example 69

Polymer-bound 1-P(Ph)-2-$C_6H_4$SMe

A suspension of polymer-bound P(PH)Cl Example 52-D (2.0 g, 1.86 mmol, 0.93 mm/g), and 1,2-$MeSC_6H_4ZnI$ (15.0 mmol, 0.5 M in THF solution) in 10 mL of THF was refluxed overnight before the solution was filtered off. The resulting resin was washed with hexane (2×10 mL), $CH_2Cl_2$ (5×10 mL), $Me_2CHOH$ (5 mL) and hexane (5×10 mL). The resin was dried in vacuo overnight. $^{31}P$ NMR (122 MHz, $CDCl_3$): δ 56.9 ppm.

Example 70

Polymer-bound 1-P(Ph)-8-N,N-Dimethylnaphthylamine

A solution of N,N,N',N'-tetramethylethylenediamine (2.04 g, 17.6 mmol) in 15 mL of hexane was treated with n-butyllithium (9.28 mmol, 1.6 M solution in Hexane) dropwise over a period of 5 min, the solution was stirred an additional 15 min before N,N-dimethyl-1-naphthylamine (4.0 g, 23.4 mmol) was added. The resulting mixture was stirred at room temperature overnight before a polymer-bound P(Ph)Cl Example 52-D (1.0 g, 0.93 mmol, 0.93 mm/g) was added to the reaction mixture. The resulting suspension was stirred overnight before solution was filtered off and resin was washed with hexane (2×10 mL), $CH_2Cl_2$ (5×10 mL), $Me_2CHOH$ (5 mL) and hexane (5×10 mL). The resin was dried in vacuo overnight. $^{31}P$ NMR (122 MHz, $CDCl_3$): δ 65.0 ppm.

Example 71

Polymer-bound P(Ph)-2-(R)-N,N-Dimethyl-1'-Ferrocenylethyl Amine

A solution of N,N,N',N'-tetramethylethylenediamine (0.22 g, 1.89 mmol) in 5 mL of hexane was treated with n-butyllithium (1.28 mmol, 1.6 M solution in Hexane)

dropwise over a period of 5 min, the solution was stirred an additional 15 min before (R)-(+)-N,N-dimethyl-1-ferrocenylethylamine (0.5 g, 1.89 mmol) was added. The resulting mixture was stirred at room temperature overnight before a polymer-bound P(Ph)Cl (0.5 g, 0.466 mmol, 0.93 mm/g, Example 52-D) was added to the reaction mixture. The resulting suspension was stirred overnight before solution was filtered off and resin was washed with hexane (2×10 mL), $CH_2Cl_2$ (5×10 mL), $Me_2CHOH$ (5 mL) and hexane (5×10 mL). The resin was dried in vacuo overnight. $^{31}P$ NMR (122 MHz, $CDCl_3$): δ 52.5 ppm.

Example 72

Polymer-bound P(Et)-2-(R)-N,N-Dimethyl-1'-Ferrocenylethyl Amine

A similar procedure to those described above was used to synthesize the title compound using N,N,N',N'-tetramethylethylenediamine (0.80 g, 6.88 mmol), n-butyllithium (4.8 mmol, 1.6 M solution in Hexane), (R)-(+)-N,N-dimethyl-1-ferrocenylethylamine (1.5 g, 5.66 mmol) and a polymer-bound P(Et)Cl from Example 52-H (2.3 g, 2.16 mmol, 0.94 mm/g). $^{31}P$ NMR (122 MHz, $CDCl_3$): δ 35.4 ppm.

Example 73

Polymer-bound P(Ph)-2-$C_4H_3S$

A suspension of polymer-bound P(Ph)Cl from Example 52-N (0.8 g, 0.82 mmol, 1.03 mm/g), and 2-thienyllithium (5.0 mmol, 2 M in THF solution) in 10 mL of THF was stirred at room temperature over 2 h before the solution was filtered off. The resulting resin was washed with hexane (2×10 mL), $CH_2Cl_2$ (5×10 mL), $Me_2CHOH$ (5 mL) and hexane (5×10 mL). The resin was dried in vacuo overnight. $^{31}P$ NMR (122 MHz, $CDCl_3$): δ 37.0 ppm.

Example 74

Polymer-bound P(Ph)-2-$C_3H_2SN$

A suspension of polymer-bound P(Ph)Cl from Example 52-D (2.0 g, 1.86 mmol, 0.93 mm/g), and 2-thiazolezinc bromide (15.0 mmol, 0.5 M in THF solution) in 10 mL of THF was refluxed overnight before the solution was filtered off. The resulting resin was washed with hexane (2×10 mL), $CH_2Cl_2$ (5×10 mL), $Me_2CHOH$ (5 mL) and hexane (5×10 mL). The resin was dried in vacuo overnight. $^{31}P$ NMR (122MHz, $CDCl_3$): δ 56.2 ppm.

Example 75

Polymer-bound P(Ph)-2-$C_5H_4N$

A suspension of polymer-bound P(Ph)Cl from Example 52-D (3.0 g, 2.79 mmol, 0.93 mm/g), and 2-pyridylmagnesium bromide (15 mmol, 0.5 M in THF solution) in 20 mL of THF was stirred at room temperature overnight before the solution was filtered off. The resulting resin was washed with hexane (2×10 mL), $CH_2Cl_2$ (5×10 mL), $Me_2CHOH$ (5 mL) and hexane (5×10 mL). The resin was dried in vacuo overnight. $^{31}P$ NMR (122 MHz, $CDCl_3$): δ 63.4 ppm.

Example 76

Polymer-bound P(Ph)$CH_2CH_2PPh_2$ by Hydrophosphinations

A suspension of polymer-bound N($CH_2CH_2Me$)P(Ph)H from Example 52-U (0.8 g, 0.80 mmol, 1.0 mm/g) and diphenylvinylphosphine (1.5 g, 7.06 mmol) in 20 mL of toluene was refluxed overnight before the solution was filtered off. The resulting resin was washed with hexane (2×10 mL), $CH_2Cl_2$ (5×10 mL), $Me_2CHOH$ (5 mL) and hexane (5×10 mL). The resin was dried in vacuo overnight. $^{31}P$ NMR (122 MHz, $CDCl_3$): δ 62.7, −11.4 ppm.

Example 77

Polymer-bound P(Ph)$CH_2CH_2SPh$

A suspension of polymer-bound N(Ph)P(Ph)CH=CH from Example 52-J (2.0 g, 2.0 mmol, 1.0 mm/g) and EtS-SEt (1.0 g, 8.18 mmol) in 20 mL of THF was refluxed for 2 days before the solution was filtered off. The resulting resin was washed with hexane (2×10 mL), $CH_2Cl_2$ (5×10 mL), $Me_2CHOH$ (5 mL) and hexane (5×10 mL). The resin was dried in vacuo overnight. $^{31}P$ NMR (122 MHz, $CDCl_3$): δ 70.9 ppm.

Cleavage of Bidentate Ligands From Resin

Example 78

Synthesis of PhP(Cl)$CH_2CH_2PPh_2$

A suspension of polymer-bound PhP$CH_2CH_2PPh_2$ (1.0 g, 0.80 mmol, prepared as in Example 5 using n-propylamine and phenylMgBr, $^{31}P$ NMR 62.7, −11.3 ppm) and $PCd_3$ (0.75 g, 5.46 mmol) in THF (10 mL) was stirred overnight at room temperature before the resin was filtered off and washed with THF (2×10 mL). Removal of solvents and excess $PCl_3$ from the filtrates by vacuum afforded 160 mg (56% yield) of crude PhP(Cl)$CH_2CH_2PPh_2$. It was >95% pure by $^1H$ NMR and GC/MS. $^{31}P$ NMR (202 MHz, $CDCl_3$): δ 93.9 (d, J=30.2 Hz), −11.8 (d, J=30.4 Hz) ppm. $^1H$ NMR (500 MHz, $CDCl_3$): δ 7.53–7.16 (m, 15H), 2.05 (m, 4H). $^{13}C$ NMR (125 MHz, $CDCl_3$): δ 138.0, 137.7, 132.9, 131.2, 131.0, 129.1, 128.9, 128.7, 32.8, 22.5. HRMS: Calcd. for $C_{20}H_{19}P_2Cl(M^+)$: 356.0651. Found: 356.0650.

Example 79

Synthesis of PhPH(O)$CH_2CH_2$PMe(Ph)

A suspension of polymer-bound PhP$CH_2CH_2$PMe(Ph) (1.0 g, 0.92 mmol, prepared as in Example 65, $^{31}p$ NMR 47.9, −31.2 ppm) and $H_2O$ (0.75 g, 41.7 mmol) in THF (10 mL) was refluxed overnight before the resin was filtered off and washed with THF (2×10 mL). Removal of solvents and excess $H_2O$ from the filtrates by vacuum afforded 100 mg (39% yield) of crude PhPH(O)$CH_2CH_2$PMe(Ph). It was >95% pure by $^1H$ NMR and GC/MS. $^{31}P$ NMR (202 MHz, $CDCl_3$): δ 29.2 (d, J=38.1 Hz), −30.0 (d, J=38.1 Hz); 29.0 (d, J=38.6 Hz), −30.3 (d, J=38.7 Hz) ppm. $^{31}P$ NMR (202 MHz, $CDCl_3$, $^1H$-coupled): δ 29.1 (d, $J_{P-H}$=440.4 Hz), −30.0; 29.1 (d, $J_{P-H}$=440.4 Hz), −30.3 ppm.

Example 80

Synthesis of 1-PhP(Cl)-2-MeO$C_6H_4$

A suspension of polymer-bound 1-PPh-2-MeO$C_6H_4$ (2.0 g, 0.873 mmol/g, 1.746 mmol, prepared as in Example 66, $^{31}P$ NMR 57.3 ) and $PCl_3$ (1.3 g, 9.49 mmol) in 15 mL of THF was stirred overnight at room temperature before the resin was filtered off and washed with THF (2×10 mL). Removal of solvents and excess $PCl_3$ from the filtrates by vacuum afforded 325 mg (74% yield) of crude 1-PhP(Cl)-2-MeO$C_6H_4$. It was >95% pure by $^1H$ NMR and GC/MS.

$^{31}$P NMR (202 MHz, CDCl$_3$): δ 78.3 ppm. $^1$H NMR (500 MHz, CDCl$_3$): δ 7.45 (m, 3H), 7.22 (m, 4H), 6.91 (m, 1H), 6.68 (m, 1H), 3.54 (s, 3H). $^{13}$C NMR (125 MHz, CDCl$_3$): δ 160.5, 139.0, 132.2, 131.7, 131.6, 130.4, 128.5, 126.3, 121.5, 110.8, 55.9. HRMS: Calcd. for C$^{13}$H$_{12}$PClO(M$^+$): 250.0314. Found: 250.0311.

Example 81

Synthesis of 1-PhP(Cl)-2,4-(MeO)$_2$C$_6$H$_3$

A suspension of polymer-bound 1-PPh-2,4-(MeO)$_2$C$_6$H$_3$ (2.0 g, 0.85 mmol/g, 1.70 mmol, prepared as in Example 57, $^{31}$P NMR 56.1) and PCl$_3$ (1.3 g, 9.49 mmol) in 15 mL of THF was stirred overnight at room temperature before the resin was filtered off and washed with THF (2×10 mL). Removal of solvents and excess PCl$_3$ from the filtrates by vacuum afforded 450 mg (94% yield) of crude 1-PhP(Cl)-2,4-(MeO)$_2$C$_6$H$_3$. It was >95% pure by $^1$H NMR and GC/MS. $^{31}$P NMR (202 MHz, CDCl$_3$): δ 78.8 ppm. $^1$H NMR (500 MHz, CDCl$_3$): δ 7.43 (m, 2H), 7.22 (m, 4H), 6.38 (m, 1H), 6.27 (m, 1H), 3.62 (s, 3H), 3.55 (s, 3H). $^{13}$C NMR (125 MHz, CDCl$_3$): δ 163.4, 162.0. 139.0, 133.2, 131.5, 129.9, 128.2, 117.4, 105.7, 98.3, 55.7, 55.3. HRMS: Calcd. for C$_{14}$H$_{14}$PClO$_2$(M$^+$): 280.0420. Found: 280.0421.

Example 82

Synthesis of 1-PhP(Cl)-3-MeOC$_6$H$_4$

A suspension of polymer-bound 1-PPh-3-MeOC$_6$H$_4$ (0.8 g, 0.95 mmol/g, 0.76 mmol, prepared as in Example 58, $^{31}$P NMR 52.8) and PCl$_3$ (0.56 g, 4.1 mmol) in 15 mL of THF was stirred overnight at room temperature before the resin was filtered off and washed with THF (2×10 mL). Removal of solvents and excess PCl$_3$ from the filtrates by vacuum afforded 80 mg (42% yield) of crude 1-PPh(Cl)-3-MeOC$_6$H$_4$. It was >95% pure by $^1$H NMR and GC/MS. $^{31}$P NMR (202 MHz, CDCl$_3$): δ 83.3 ppm. $^1$H NMR (500 MHz, CDCl$_3$): δ 7.05 (m, 2H), 7.30 (m, 3H), 7.21 (m, 1H), 7.06 (m, 2H), 6.83 (m, 1H), 3.68 (s, 3H). $^{13}$C NMR (125 MHz, CDCl$_3$): δ 159.8, 140.4, 139.0, 132.0, 130.6, 129.9, 128.8, 124.1, 117.1, 116.4, 55.5. HRMS: Calcd for C$_{13}$H$_{12}$PClO (M$^+$): 250.0314. Found: 250.0322.

Example 83

Synthesis of 2-PhP(Cl)C$_4$H$_3$S

A suspension of polymer-bound 2-PhPC$_4$H$_3$S (0.8 g, 0.98 mmol/g, 0.78 mmol, from Example 73, $^{31}$P NMR 37.0) and PCl$_3$ (0.56 g, 4.1 mmol) in 10 mL of THF was stirred overnight at room temperature before the resin was filtered off and washed with THF (2×10 mL). Removal of solvents and excess PCl$_3$ from the filtrates by vacuum afforded 80 mg (45% yield) of crude 2-PhP(Cl)C$_4$H$_3$S. It was >95% pure by $^1$H NMR and GC/MS. $^{31}$P NMR (202 MHz, CDCl$_3$): δ 66.8 ppm. $^1$H NMR (500 MHz, CDCl$_3$): δ 7.67–7.61 (m, 3H), 7.43 (m, 1H), 7.36 (m, 3H), 7.03 (m, 1H). $^{13}$C NMR (125 MHz, CDCl$_3$): δ 140.9, 138.4, 136.6, 134.2, 130.8, 130.3, 128.4, 127.7. HRMS: Calcd. for C$_{10}$H$_8$PClSO(MO$^+$): 241.9722. Found: 241.9739.

Synthesis of Polymer-bound Tridentate Ligands

Example 84

Polymer-Bound P(CH$_2$CH$_2$PPh$_2$)$_2$

A suspension of polymer-bound P(CH=CH$_2$)$_2$ (2.0 g, 0.985 mm/g, 1.97 mmol, from Example 52-F), Ph$_2$PH (5.5 g, 29.6 mmol) and NaO-tBu (0.1 g, 1.0 mmol) in 15 mL of THF was refluxed overnight before the solution was filtered off. The resulting resin was washed with hexane (2×10 mL), CH$_2$Cl$_2$ (5×10 mL), Me$_2$CHOH (2×5 mL) and hexane (5×10 mL). The resin was dried in vacuo overnight. $^{31}$P NMR (122 MHz, CDCl$_3$): δ 65.6, −12.0 ppm.

Example 85

Polymer-bound P[CH$_2$CH$_2$)P(Ph)Me]$_2$

A suspension of polymer-bound P(CH=CH$_2$)$_2$ (1.0 g, 0.985 mmol, from Example 52-F), Ph(Me)PH (1.5 g, 10.9 mmol) and NaO-tBu (0.05 g, 0.5 mmol) in 10 mL of THF was refluxed overnight before the solution was filtered off. The resulting resin was washed with hexane (2×10 mL), CH$_2$Cl$_2$ (5×10 mL), Me$_2$CHOH (2×5 mL) and hexane (5×10 mL). The resin was dried in vacuo overnight. $^{31}$P NMR (122 MHz, CDCl$_3$): δ 64.8, −31.5 ppm.

Example 86

Polymer-bound P(C$_4$H$_3$O)(Br)

A solution of furan (7.0 g, 102.8 mmol) and PBr$_3$ (25.0 g, 92.4 mmol) in 30 ml of pyridine was refluxed over 5 h before the resulting mixture was cooled to room temperature and 100 mL of hexane was added. This crude products exhibit a single $^{31}$P NMR peak at 103.5 ppm. After filtered off the solids, the hexane was removed from the filtrate by vacuum, a polymer-bound NH(CH$_2$CH$_2$Me) prepared as in Example 1 (10 g, 11.0 mmol, 1.1 mm/g) was added to the solution above. The resulting suspension was stirred overnight before the solution was filtered off. The resulting resin was washed with hexane (2×30 mL), CH$_2$Cl (5×30 mL), THF (2×30 mL) and hexane (5×10 mL). The resin was dried in vacuo overnight. $^{31}$P NMR (122 MHz, CDCl$_3$): δ 113.1 ppm.

Example 87

Polymer-bound P(C$_4$H$_3$O)(C$_4$H$_3$S)

A suspension of polymer-bound P(C$_4$H$_3$O)(Br) from Example 86 (1.0 g, 1.0 mmol) in 15 mL of THF was treated slowly with 2-thienyllithium (10.0 mmol, 1.0 M solution in THF) over a period of 5 min. The resulting mixture was stirred for 2 h at room temperature before the solution was filtered off. The resulting resin was washed with hexane (2×10 mL), CH$_2$Cl$_2$ (5×10 mL), Me$_2$CHOH (2×5 mL) and hexane (5×10 mL). The resin was dried in vacuo overnight. $^{31}$P NMR (122 MHz, CDCl$_3$): δ 28.4 ppm.

Example 88

Polymer-bound P(C$_5$H$_4$N)$_2$

A suspension of polymer-bound PCd$_2$ (2.0 g, 0.968 mm/g. 1.94 mmol, from Example 52-C) in 15 mL of THF was treated slowly with 2-pyridylzinc bromide (15 mmol, 0.5 M solution in THF) over a period of 5 min. The resulting mixture was refluxed overnight before the solution was filtered off. The resulting resin was washed with hexane (2×10 mL), CH$_2$Cl$_2$ (5×10 mL), Me$_2$CHOH (2×5 mL) and hexane (5×10 mL). The resin was dried in vacuo overnight. $^{31}$P NMR (122 MHz, CDCl$_3$): δ 59.0 ppm.

Example 89

Polymer-bound P(2-C$_6$H$_4$SMe)$_2$

A suspension of polymer-bound PCl$_2$ (2.0 g, 0.968 mm/g, 1.94 mmol, from Example 52-C) in 15 mL of THF was treated slowly with 2-(thiomethyl)phenylzinc iodide (15 mmol, 0.5 M solution in THF) over a period of 5 min. The resulting mixture was refluxed overnight before the solution was filtered off. The resulting resin was washed with hexane (2×10 mL), $CH_2Cl_2$ (5×10 mL), $Me_2CHOH$ (2×5 mL) and hexane (5×10 mL). The resin was dried in vacuo overnight. $^{31}P$ NMR (122 MHz, $CDCl_3$): δ 49.6 ppm.

Example 90

Polymer-bound $P(2-C_6H_4OMe)_2$

A suspension of polymer-bound $PCl_2$ (2.0 g, 0.968 mm/g, 1.94 mmol, from Example 52-C) in 15 mL of THF was treated slowly with 2-methoxyphenylmagnesium bromide (15 mmol, 0.5 M solution in THF) over a period of 5 min. The resulting mixture was refluxed for 3 h before the solution was filtered off. The resulting resin was washed with hexane (2×10 mL), $CH_2Cl_2$ (5×10 mL), $Me_2CHOH$ (2×5 mL) and hexane (5×10 mL). The resin was dried in vacuo overnight. $^{31}P$ NMR (122 MHz, $CDCl_3$): δ 48.5 ppm.

Example 91

Polymer-bound $P(8-C_{10}H_6NMe_2)_2$

A solution of N,N,N',N'-tetramethylethylenediamine (2.1 g, 18.1 mmol) in 15 mL of hexane was treated with n-butyllithium (12.8 mmol, 1.6 M solution in Hexane) dropwise over a period of 5 min, the solution was stirred an additional 15 min before N,N-dimethyl-1-naphthylamine (5.0 g, 29.2 mmol) was added to the reaction solution. The resulting mixture was stirred at room temperature overnight before a polymer-bound $PCl_2$ (1.0 g, 0.97 mmol, from Example 52-C) was added to the reaction mixture. The resulting suspension was stirred overnight before solution was filtered off and resin was washed with hexane (2×10 mL), $CH_2Cl_2$ (5×10 mL), $Me_2CHOH$ (5 mL) and hexane (5×10 mL). The resin was dried in vacuo overnight. $^{31}P$ NMR (122 MHz, $CDCl_3$): δ 70.0 ppm.

Cleavage of Tridentate Ligands From Resin

Example 92

Synthesis of $Ph_2PCH_2CH_2PH(O)CH_2CH_2PPh_2$

A suspension of polymer-bound $P(CH_2CH_2PPh_2)_2$ (1.0 g, 0.72 mmol, from Example 84) and $H_2O$ (0.5 g, 27.8 mmol) in THF (10 mL) was refluxed overnight before the resin was filtered off and washed with THF (2×10 mL). Removal of solvents and excess $H_2O$ from the filtrates by vacuum afforded 127 mg (37% yield) of crude $Ph_2PCH_2CH_2PH(O)CH_2CH_2PPh_2$. It was >95% pure by $^1H$ NMR and GC/MS. $^{31}P$ NMR (202 MHz, $CDCl_3$): δ 36.4 (dd, J=43.5 Hz), −11.7 (d, J=43.5 Hz) ppm. $^{31}P$ NMR (202 MHz, $CDCl_3$, $^1H$-coupled): δ 36.2 (d, $J_{P-H}$=455.3 Hz), −11.7 ppm. $^1H$ NMR (500 MHz, $CDCl_3$): δ 7.68–7.19 (m, 20H), 6.81 (d, $J_{P-H}$=452.6 Hz, 1H), 2.50–1.73 (m, 8H). $^{13}C$ NMR (125 MHz, $CDCl_3$): δ 136.9, 132.7, 131.5, 128.8, 24.3, 19.5.

Example 93

Synthesis of $PhP(Me)CH_2CH_2PH(O)CH_2CH_2P(Me)Ph$

A suspension of polymer-bound $P[CH_2CH_2P(Me)Ph]_2$ (1.0 g, 0.79 mmol, from Example 85) and $H_2O$ (0.4 g, 22.2 mmol) in THF (10 mL) was refluxed overnight before the resin was filtered off and washed with THF (2×10 mL). Removal of solvents and excess $H_2O$ from the filtrates by vacuum afforded 200 mg (72% yield) of crude $PhP(Me)CH_2CH_2PH(O)CH_2CH_2P(Me)Ph$. It was >95% pure by $^1H$ NMR and GC/MS. $^{31}P$ NMR (202 MHz, $CDCl_3$): δ 37.2 (t, J=36.1 Hz), −30.2 (dd, $^3J$=36.3 Hz, $^6J$=4.7 Hz, $^6J$=4.4 Hz ), −30.5 (dd, $^3J$=36.3 Hz, $^6J$=3.2 Hz, $^6J$=3.6 Hz ) ppm. $^{31}P$ NMR (202 MHz, $CDCl_3$, $^1H$-coupled): δ 37.2 (d, $J_{P-H}$= 454.7 Hz), −30.2 (d, J=36.5 Hz), −30.5 (d, J=37.1 Hz) ppm. $^1H$ NMR (500 MHz, $CDCl_3$): δ 7.39–7.17 (m, 10H), 6.72 (d, $J_{P-H}$=453.8 Hz, 1H), 1.79–1.65 (m, 8H), 1.26 (s, 6H). $^{13}C$ NMR (125 MHz, $CDCl_3$): δ 137.9, 131.4, 128.9, 128.3, 23.9, 21.6, 10.8. HRMS: Calcd. for $C_{18}H_{25}P_3O_3(MO_2^+)$: 382.1017. Found: 382.0954.

Example 94

Synthesis of $C_4H_3O—PH(O)—C_4H_3S$

A suspension of polymer-bound $P(C_4H_3O)(C_4H_3S)$ (0.6 g, 0.54 mmol, 0.899 mm/g, from Example 87) and $H_2O$ (0.5 g, 27.7 mmol) in THF (10 mL) was refluxed overnight before the resin was filtered off and washed with THF (2×10 mL). Removal of solvents and excess $H_2O$ from the filtrates by vacuum afforded 16 mg (15% yield) of crude $C_4H_3O—PH(O)—C_4H_3S$. It was >95% pure by $^1H$ NMR and GC/MS. $^{31}P$ NMR (122 MHz, $CDCl_3$): δ −6.66 ppm. $^{31}P$ NMR (122 MHz, $^1H$-coupled, $CDCl_3$): δ −6.66 (d, $J_{P-H}$=515.5 Hz) ppm.

Example 95

Synthesis of $2-MeSC_6H_4P(Cl)-2-MeSC_6H_4$

A suspension of polymer-bound $P[C_6H_4(SMe)_2]_2$ (1.0 g, 0.83 mmol) and $PCl_3$ (0.75 g, 5.47 mmol, from Example 89) in THF (10 mL) was stirred overnight at room temperature before the resin was filtered off and washed with THF (2×10 mL). Removal of solvents and excess $PCl_3$ from the filtrates by vacuum afforded 205 mg (79% yield) of crude $2-MeSC_6H_4P(Cl)-2-MeSC_6H_4$. It was >95% pure by $^1H$ NMR and GC/MS. $^{31}P$ NMR (202 MHz, $CDCl_3$): δ 57.3 ppm. $^1H$ NMR (500 MHz, $CDCl_3$): δ 7.40 (m, 2H), 7.32 (m, 4H), 7.20 (m, 2H), 2.34 (s, 6H). $^{13}C$ NMR (125 MHz, $CDCl_3$): δ 141.7, 140.5, 132.6, 131.1, 130.0, 127.5, 19.0. HRMS: Calcd. for $C_{14}H_{14}PClS_2(M^+)$: 311.9963. Found: 311.9970.

Example 96

Synthesis of $2-MeOC_6H_4P(Cl)-2-MeOC_6H_4$

A suspension of polymer-bound $P[C_6H_4(OMe)_2]_2$ (2.0 g, 1.65 mmol, 0.83 mm/g, from Example 90) and $PCl_3$ (1.3 g, 7.30 mmol) in THF (10 mL) was stirred overnight at room temperature before the resin was filtered off and washed with THF (2×10 mL). Removal of solvents and excess $PCl_3$ from the filtrates by vacuum afforded 400 mg (86% yield) of crude $2-MeOC_6H_4P(Cl)-2-MeOC_6H_4$. It was >95% pure by $^1H$ NMR and GC/MS. $^{31}P$ NMR (202 MHz, $CDCl_3$): δ 70.8 ppm. $^1H$ NMR (500 MHz, $CDCl_3$): δ 7.30 (m, 4H), 6.90 (m, 2H), 6.80 (m, 2H), 3.73 (s, 6H). $^{13}C$ NMR (125 MHz, $CDCl_3$): δ 161.3, 132.5, 132.1, 126.3, 121.5, 110.9, 56.2. HRMS: Calcd. for $C_{14}H_{14}PClO_2(M^+)$: 280.0420. Found: 280.0429.

Example 97

Synthesis of $8-Me_2NC_{10}H_6PH(O)-8-Me_2NC_{10}H_6$

A suspension of polymer-bound $P[8-Me_2NC_8H_6]_2$ (1.0 g, 0.77 mmol, from Example 91) and $H_2O$ (0.5 g, 27.8 mmol)

in THF (10 mL) was refluxed overnight before the resin was filtered off and washed with THF (2×10 mL). Removal of solvents and excess H$_2$O from the filtrates by vacuum afforded 115 mg (38% yield) of crude 8-Me$_2$NC$_{10}$H$_6$PH(O)-8-Me$_2$NC$_{10}$H$_6$. $^{31}$P NMR (202 MHz, CDCl$_3$): δ 15.7 ppm. $^{31}$P NMR (202 MHz, CDCl$_3$, $^1$H-coupled): δ 15.7 (d, J$_{P-H}$=605.8 Hz) ppm.

Cleavage of Diphosphine Ligands From Resin

Example 98

Synthesis of 1-(Diethylphosphino)-2 (ethoxyethylphosphinite)ethane

A suspension of polymer-bound (Et)PCH$_2$CH$_2$P(Et)$_2$ (1.0 g, 0.899 mmol/g, 0.90 mmol, prepared as in Example 5) and EtOH (0.41 g, 9.1 mmol) in THF (10 mL) was refluxed overnight before the resin was filtered off and washed with THF (2×10 mL). Removal of solvents and excess EtOH from the filtrates by vacuum afforded 162 mg (81% yield) of (EtO)(Et)PCH$_2$CH$_2$P(Et)$_2$. It was >95% pure by $^1$H NMR and GC/MS. $^{31}$P NMR (202 MHz, C$_6$D$_6$): δ 135.8 (d, J=20.5 Hz), −18.2 (d, J=20.2 Hz). $^1$H NMR (500 MHz, C$_6$D$_6$): δ 3.76 (m, 2H), 1.81 (m, 2H), 1.66 (m, 4H), 1.48 (m, 2H), 1.36 (m, 4H), 1.22–1.07 (m, 12H). $^{13}$C NMR (125 MHz, C$_6$D$_6$): δ 67.2, 30.2, 27.1, 21.8, 20.5, 18.8, 11.1, 9.5. HRMS: Calcd. for C$_8$H$_{19}$P$_2$O(M$^+$−Et): 193.0911. Found: 193.0922.

Example 99

Synthesis of 1-(Diisobutylphosphino)-2-(ethoxylisobutylphosphinite)ethane

A similar procedure to that described above in Example 98 was used to prepare the title compound using polymer-bound (Me$_2$CHCH$_2$)PCH$_2$CH$_2$P(CH$_2$CHMe)$_2$ (1.17 g, 0.82 mmol/g, 0.96 mmol, prepared as in Example 5) and EtOH (0.27 g, 6.0 mmol). After the solvents were removed from filtrates by vacuum, 70 mg (24% yield) of (EtO)(Me$_2$CHCH$_2$)PCH$_2$CH$_2$P(CH$_2$CHMe)$_2$ was obtained. It was >95% pure by $^1$H NMR and GC/MS. $^{31}$P NMR (202 MHz, CDCl$_3$): δ 132.5 (d, J=20.4 Hz), −33.5 (d, J=20.4 Hz). $^1$H NMR (500 MHz, CDCl$_3$): δ 3.66 (m, 2H), 1.79 (m, 1H), 1.63 (m, 4H), 1.43 (m, 2H), 1.26–1.13 (m, 8H), 1.03–0.92 (m, 19H). $^{13}$C (125 MHz, CDCl$_3$): δ 65.6, 43.4, 38.6, 29.1, 26.3, 25.2, 24.6, 24.3, 23.8, 22.1, 17.2. MS (rel. abundance): M$^+$−Et (6), M$^+$−EtO (10), 221.1 (100). HRMS: Calcd. for C$_{14}$H$_{31}$P$_2$O (M$^+$−Et): 277.1850. Found: 277.1846.

Example 100

Synthesis of 1-(Diphenylphosphino)-2-(ethoxylphenylphosphinite)ethane

A suspension of polymer-bound (Ph)PCH$_2$CH$_2$P(Ph)$_2$ (13.6 g, ~0.74 mmol/g, ~10.1 mmol, prepared as in Example 5) and EtOH (5 g, 109 mmol) in THF (200 mL) was refluxed overnight before the resin was filtered off and washed with THF (2×10 mL). The filtrate was dried in vacuo to remove the solvent and excess EtOH, the residue was extracted with 3×20 mL of hexane. The combined hexane extracts were dried under reduced pressure to give 2.17 g (59% yield) of (Ph)(EtO)PCH$_2$CH$_2$P(Ph)$_2$. It was >95% pure by $^1$H NMR and GC/MS. $^{31}$P NMR (122 MHz, C$_6$D$_6$): δ 120.4, −11.6 ppm. $^1$H NMR (500 MHz, C$_6$D$_6$): δ 7.59–7.13 (m, 15H), 3.69 (m, 2H), 2.3–2.0 (m, 2H), 1.1 (t, J=7.0 Hz). $^{13}$C NMR (125 MHz, C$_6$D$_6$): δ 145.4, 141.5, 131.8, 131.5, 131.0, 130.9, 130.7, 130.5, 67.9, 34.1, 24.3, 19.5 HRMS: Calcd. for C$_{22}$H$_{24}$P$_2$O: 366.1302. Found: 366.1306.

Example 101

Synthesis of 1-[di(4-Fluorophenyl)phosphino]-2-[ethoxyl(4-fluorophenyl)phosphinite)ethane An analogous procedure to that for (Et)(EtO)PCH$_2$CH)P(Et)$_2$ was used for the synthesis of title compound using polymer-bound (4-FC$_6$H$_5$)PCH$_2$CH$_2$P(4-FC$_6$H$_5$)$_2$ (1.28 g, ~0.75 mmol/g, ~0.96 mmol, prepared as in Example 5) and EtOH (0.27 g, 6.0 mmol). After the solvents were removed from filtrates by vacuum, 110 mg (27% yield) of (EtO)(4-FC$_6$H$_5$)PCH$_2$CH$_2$P(4-FC$_6$H$_5$)$_2$ was obtained. It was >95% pure by $^1$H NMR and GC/MS. $^{31}$P NMR (202 MHz, CDCl$_3$): δ 119.2 (d, J=28.5 Hz), −14.0 (d, J=28.5 Hz). $^{19}$F (377 MHz CDCl$_3$): δ 112.0, 112.6. $^1$H NMR (500 MHz, CDCl$_3$): δ 7.36 (m, 2H), 7.19 (m, 4H), 7.00 (m, 2H), 6.92 (m, 4H), 3.66 (m, 2H), 1.90 (m, 2H), 1.70 (m, 1H), 1.58 (m, 1H), 1.14 (t, J=6.99 Hz, 3H). $^{13}$C (125 MHz, CDCl$_3$): δ 164.6, 164.3, 162.6, 162.2, 134.3, 133.5, 131.3, 115.9, 65.7, 30.9, 21.6, 17.1. HRMS: Calcd. for C$_{22}$H$_{21}$P$_2$OF$_3$: 420.1020. Found: 420.1028.

Example 102

Synthesis of 1-[di(4-Chlorophenyl)phosphino]-2-[methoxyl(4-chlorophenyl)phosphinite)ethane An analogous procedure to that for (Et)(EtO)PCH$_2$CH$_2$P(Et)$_2$ was used for the synthesis of title compound using polymer-bound (4-ClC$_6$H$_5$)PCH$_2$CH$_2$P(4-ClC$_6$H$_5$)$_2$ (1.2 g, ~0.80 mmol/g, ~0.96 mmol, prepared as in Example 5) and MeOH (0.27 g, 6.0 mmol). After the solvents were removed from filtrates by vacuum, 132 mg (30% yield) of (MeO)(4-ClC$_6$H$_5$)PCH$_2$CH$_2$P(4-ClC$_6$H$_5$)$_2$ was obtained. It was >95% pure by $^1$H NMR and GC/MS. $^{31}$P NMR (202 MHz, CDCl$_3$): δ 124.7 (d, J=27.9 Hz), −13.4 (d, J=27.9 Hz). $^1$H NMR (500 MHz, CDCl$_3$): δ 7.28–7.12 (m, 12H), 3.45 (d, J$_{P-H}$=13.6 Hz, 3H), 1.93(m, 2H), 1.66 (m, 2H). $^{13}$C (125 MHz, CDCl$_3$): δ 139.6, 136.2, 135.2, 135.1, 133.9, 130.7, 128.8, 128.5, 56.8, 30.5, 21.1. HRMS: Calcd. for C$_{21}$H$_{19}$P$_2$OCl$_3$: 453.9977. Found: 453.9951.

Example 103

Synthesis of 1-[di(2-Mesityl)phosphino]-2-[methoxyl(2-mesityl)phosphinite]ethane The procedure described above was employed except that polymer-bound (2,4,6-Me$_3$C$_6$H$_2$)PCH$_2$CH$_2$P(2,4,6-Me$_3$C$_6$H$_2$)$_2$ (1.33 g, ~0.72 mmol/g, ~0.96 mmol, prepared as in Example 5) and MeOH (0.21 g, 6.0 mmol) were used to prepare the title compound. After the solvents were removed from filtrates by vacuum, 136 mg (30% yield) of (MeO)(2,4,6-Me$_3$C$_6$H$_2$)PCH$_2$CH$_2$P(2,4,6-Me$_3$C$_6$H$_2$)$_2$ was obtained. It was >95% pure by $^1$H NMR and GC/MS. $^{31}$P NMR (202 MHz, CDCl$_3$): δ 131.6 (d, J=33.2 Hz), −17.7 (d, J=33.2 Hz). $^1$H NMR (500 MHz, CDCl$_3$): δ 6.75(m, 6H), 3.47 (d, J$_{P-H}$=14.3 Hz, 3H), 2.48–2.19 (m, 31H). $^{13}$C (125 MHz, CDCl$_3$): δ 142.4, 142.1, 141.6, 139.1, 137.4, 132.7, 132.6, 129.8, 67.9, 57.1, 28.0, 25.6, 23.1, 21.3, 20.7. HRMS: Calcd. for C$_{30}$H$_{40}$P$_2$O: 478.2554. Found: 478.2553.

Example 104

Synthesis of 1-[Diphenethylphosphino]-2-(methoxylphenethyl phosphinite)ethane

A similar procedure to those described above was used to prepare the title compound using polymer-bound (PhCH$_2$CH$_2$)PCH$_2$CH$_2$P(CH$_2$CH$_2$Ph)$_2$ (1.29 g, ~0.74 mmol/g, ~0.96 mmol, prepared as in Example 5) and MeOH (0.21 g, 6.0 mmol). After the solvents were removed from filtrates by vacuum, 110 mg (26% yield) of (MeO)(PhCH$_2$CH$_2$)PCH$_2$CH$_2$P(CH$_2$CH$_2$Ph)$_2$ was obtained. It was >95% pure by $^1$H NMR and GC/MS. $^{31}$P NMR (202 MHz, CDCl$_3$): δ 138.5 (d, J=21.7Hz), −23.0 (d, J=21.9Hz). $^1$H NMR (500 MHz, CDCl$_3$): δ 7.21–7.08 (m, 15H), 3.44 (d, J$_{P-H}$=12.8 Hz, 3H), 2.77–2.64 (m, 6H), 1.91 (m, 2H), 1.67 (m, 6H), 1.51 (m, 2H). $^{13}$C (125 MHz, CDCl$_3$): δ 142.8, 142.5, 128.8, 128.3, 126.7, 126.2, 126.0, 125.9, 57.1, 34.5, 32.2, 30.5, 28.2, 27.8, 20.3. HRMS: Calcd. for C$_{27}$H$_{35}$P$_2$O (M+H)$^+$: 437.2163. Found: 437.2197.

Example 105

Synthesis of 1-(Diphenylphosphino)-2-(1-propylthio-1-phenylphosphinite)ethane

A suspension of polymer-bound (Ph)PCH$_2$CH$_2$P(Ph)$_2$ (1.0 g, 0.96 mmol, prepared as in Example 5) and CH$_3$CH$_2$CH$_2$SH (0.366 g, 4.8 mmol) in THF (10 mL) was refluxed overnight before the resin was filtered off and washed with THF (2×5 mL). The filtrate was dried in vacuo to remove the solvent and excess CH$_3$CH$_2$CH$_2$SH. The resulting residue was 117 mg (31% yield) of (Ph)(CH$_3$CH$_2$CH$_2$S)PCH$_2$CH$_2$P(Ph)$_2$. It was >95% pure by $^1$H NMR and GC/MS. $^{31}$P NMR (202 MHz, CDCl$_3$): δ 30.0 (d, J=30.0 Hz), −11.8 (d, J=29.9 Hz). $^1$H NMR (500 MHz, CDCl$_3$): δ 7.45–7.20 (m, 15H), 2.52 (m, 2H), 2.13 (m, 2H), 1.89 (m, 2H), 1.53 (m, 2H), 0.84 (t, J=7.34 Hz, 3H). $^{13}$C NMR (125 MHz, CDCl$_3$): δ 138.5, 138.0, 133.3, 132.8, 131.6, 128.8, 128.6, 128.4, 35.1, 26.9, 25.1, 23.6, 13.2. HRMS: Calcd. for C$_{23}$H$_{26}$P$_2$S: 396.1230. Found: 396.1217.

Example 106

Synthesis of 1-(Diisopropylphosphino)-2-(1-propylthio-1-isopropylphosphinite)ethane A suspension of polymer-bound (i-C$_3$H$_7$)PCH$_2$CH$_2$P(i-C$_3$H$_7$)$_2$ (1.0 g, 0.92 mmol, prepared as in Example 5) and CH$_3$CH$_2$CH$_2$SH (0.46 g, 6.0 mmol) in THF (10 mL) was refluxed overnight before the resin was filtered off and washed with THF (2×5 mL). The filtrate was dried in vacuo to remove the solvent and excess CH$_3$CH$_2$CH$_2$SH. The resulting residue was 144 mg (53% yield) of (i-C$_3$H$_7$)(CH$_3$CH$_2$CH$_2$S)PCH$_2$CH$_2$P(i-C$_3$H$_7$)$_2$. It was >95% pure by $^1$H NMR and GC/MS. $^{31}$P NMR (121 MHz, CDCl$_3$): δ 51.5 (d, J=27.4 Hz), 9.9 (d, J=27.5 Hz). $^1$H NMR (500 MHz, CDCl$_3$): δ 2.54–2.49 (m, 2H), 1.75–1.57 (m, 9H), 1.03 (m, 18H), 0.92 (t, J=7.35 Hz, 3H). $^{13}$C NMR (125 MHz, CDCl$_3$): δ 35.7, 27.7, 25.1, 23.3, 19.8, 19.0, 18.9, 18.8, 13.1 HRMS: Calcd. for C$_{11}$H$_{25}$P$_2$S (M$^+$−C$_3$H$_7$): 251.1152. Found: 251.1153.

Example 107

Synthesis of 1-(di-3',4',5'-Trifluorophenylphosphino)-2-(1-propylthio-3',4',5'-trifluorophenylphosphinite)ethane A suspension of polymer-bound (F$_3$H$_2$C$_6$)PCH$_2$CH$_2$P(C$_6$H$_2$F$_3$)$_2$ (1.0 g, 0.74 mmol, prepared as in Example 5) and CH$_3$CH$_2$CH$_2$SH (0.46 g, 6.0 mmol) in THF (10 mL) was refluxed overnight before the resin was filtered off and washed with THF (2×5 mL). The filtrate was dried in vacuo to remove the solvent and excess CH$_3$CH$_2$CH$_2$SH. The resulting residue was 295 mg (71% yield) of (C$_6$H$_2$F$_3$)(CH$_3$CH$_2$CH$_2$S)PCH$_2$CH$_2$P(C$_6$H$_2$F$_3$)$_2$. It was >95% pure by $^1$H NMR and GC/MS. $^{31}$P NMR (121 MHz, CDCl$_3$): δ 31.1 (d, J=31.7 Hz), −9.1 (d, J=31.5 Hz). $^1$H NMR (500 MHz, CDCl$_3$): δ 7.12 (m, 2H), 6.87 (m, 4H), 2.57 (m, 2H), 2.01 (m, 2H), 1.76 (m, 2H), 1.54 (m, 2H), 0.86 (t, J=7.28 Hz, 3H). $^{13}$C NMR (125 MHz, CDCl$_3$): δ 152.3, 150.3, 140.9, 139.0, 135.2, 133.2, 116.3, 115.0, 35.4, 26.7, 25.1, 23.5, 12.9. HRMS: Calcd. for C$_{23}$H$_{17}$P$_2$F$_9$S: 558.0382. Found: 558.0369.

Example 108

Synthesis of 1-(Diisopropylphosphino)-2-(1-diethylamino-1-isopropylphosphinite)ethane A polymer-bound (i-C$_3$H$_7$)PCH$_2$CH$_2$P(i-C$_3$H$_7$)$_2$ (1.0 g, 0.92 mmol, prepared as in Example 5) resin was quickly washed with HCl solution (1.0 M in Et$_2$O, 10 mL) over a period of 1.0 min, and then removal of all the solution by filtration. The resulting resin and Et$_2$NH (0.45 g, 6.2 mmol) in THF (10 mL) was refluxed overnight before the resin was filtered off and washed with THF (2×5 mL). The filtrate was dried in vacuo to remove the solvent and excess Et$_2$NH. The resulting residue was 120 mg (45% yield) of (i-C$_3$H$_7$)(Et$_2$N)PCH$_2$CH$_2$P(I-C$_3$H$_7$)$_2$. It was >95% pure by $^1$H NMR and GC/MS. $^{31}$P NMR (202 MHz, CDCl$_3$): δ 47.0 (d, J=40.3 Hz), 10.4 (d, J=40.3 Hz). $^1$H NMR (500 MHz, CDCl$_3$): δ 1.98–1.95 (m, 2H), 1.88 (m, 1H), 1.78 (m, 1H), 1.70 (m, 4H), 1.50 (m, 2H), 1.19–1.12 (m, 9H), 1.06–0.96 (m, 16H). 13C NMR (125 MHz, CDCl$_3$): δ 26.5, 23.5, 23.1, 19.8, 18.7, 15.3, 14.8, 13.1. HRMS: Calcd. for C$_{11}$H$_{27}$P$_2$O$_2$ (MO$_2^+$−Et$_2$N+H$^+$): 253.1486. Found: 253.1411.

Example 109

Synthesis of 1-(di-o-Tolylphosphino)-2-(o-tolyl-chlorophosphinite)ethane

A suspension of polymer-bound (o-MeH$_4$C$_6$)PCH$_2$CH$_2$P(o-MeC$_6$H$_4$)$_2$ (1.5 g, 0.81 mm/g, 1.2 mmol, prepared as in Example 5) and PCl$_3$ (0.82 g, 6.0 mmol) in THF (10 mL) was stirred overnight at room temperature before the resin was filtered off and washed with THF (2×5 mL). The filtrate was dried in vacuo to remove the solvent and excess PCl$_3$. The resulting residue was 365 mg (75% yield) of (o-MeH$_4$C$_6$)(Cl)PCH$_2$CH$_2$P(o-MeC$_6$H$_4$)$_2$. It was >95% pure by $^1$H NMR and GC/MS. $^{31}$P NMR (121 MHz, C$_6$D$_6$): δ 89.5 (d, J=39.7 Hz), −33.0 (d, J=39.7 Hz). $^1$H NMR (500 MHz, CDCl$_3$): δ 7.4–6.7 (m, 12H), 2.17 (s, 6H), 2.10 (s, 3H), 1.97 (m 4H). $^{13}$C NMR (125 MHz, C$_6$D$_6$): δ 141.3, 141.2, 134.9, 134.8, 130.0, 129.2, 129.1, 129.0, 127.6, 127.1, 125.4, 125.2 66.4, 30.2, 24.4, 19.8. HRMS: Calcd. for C$_{23}$H$_{26}$P$_2$O (MO$^+$−Cl+H): 380.1459. Found: 380.1513.

Example 110

Synthesis of 1-(di-3,5-Difluorophenylphosphino)-2-(3,5-difluorophenyl-chlorophosphinite)ethane A suspension of polymer-bound (C$_6$H$_3$F$_2$)PCH$_2$CH$_2$P(C$_6$H$_3$F$_2$)$_2$ (6.0 g, 0.77 mm/g, 4.6 mmol, prepared as in Example 5) and PCl$_3$ (5.0 g, 36.4 mmol) in THF (10 mL) was stirred overnight at room temperature before the resin was filtered off and washed with THF (2×5 mL) and hexane (2×10 mL). The combined filtrates were dried in vacuo to remove the solvent and excess PCl$_3$. The resulting residue was extracted with hexane (3×30 mL). The concentration of the extracts afforded 1.58 g (74%) of the title compound (C$_6$H$_3$F$_2$)(Cl)PCH$_2$CH$_2$P(C$_6$H$_3$F$_2$)$_2$. It was >95% pure by $^1$H NMR and GC/MS. $^{31}$P NMR (202 MHz, CDCl$_3$): δ 90.8

(d, J=29.8 Hz), −9.2 (d, J=29.9 Hz). $^1$H NMR (500 MHz, CDCl$_3$): δ 7.03 (m, 3H), 6.76 (m, 6H), 2.02 (m, 4H), 1.97. $^{13}$C NMR (125 MHz, C$_6$D$_6$): δ 164.1, 162.0, 141.9, 140.9, 115.1, 113.4. 106.3, 105.1, 32.4, 22.0. HRMS: Calcd. for C$_{20}$H$_{13}$F$_6$P$_2$Cl: 464.0085. Found: 464.0075.

Example 111

Synthesis of 1-(di-2-Thienylphosphino)-2-(2-thienylchlorophosphinite)ethane

A suspension of polymer-bound (2-C$_4$H$_3$S)PCH$_2$CH$_2$P(2-C$_4$H$_3$S)$_2$ (1.5 g, 0.93 mm/g, 1.4 mmol, prepared as in Example 5) and PCl$_3$ (1.0 g, 7.3 mmol) in THF (10 mL) was stirred overnight at room temperature before the resin was filtered off and washed with THF (2×5 mL) and hexane (2×10 mL). The combined filtrates were dried in vacuo to remove the solvent and excess PCl$_3$. The resulting residue was 300 mg (57%) of the title compound (2-C$_4$H$_3$S)(Cl)PCH$_2$CH$_2$P(2-C$_4$H$_3$S)$_2$. It was >95% pure by $^1$H NMR and GC/MS. $^{31}$P NMR (202 MHz, CDCl$_3$): δ 76.7 (d, J=38.3 Hz), −38.3 (d, J=38.3 Hz). $^1$H NMR (500 MHz, CDCl$_3$): δ 7.63 (d, J=4.97 Hz, 1H), 7.48 (d, J=4.89 Hz, 1H), 7.44–7.42 (m, 1H), 7.30–7.28 (m, 2H), 7.02–6.98 (m, 4H), 2.27–2.16 (m, 4H). $^{13}$C NMR (125 MHz, C$_6$D$_6$): δ 139.5, 138.3, 137.0, 136.8, 135.5, 133.8, 132.8, 127.8, 33.9, 26.9. HRMS: Calcd. for C$_{14}$H$_{14}$S$_3$P$_2$ (M$^+$−Cl+H): 339.9733. Found: 339.9742.

Example 112

Synthesis of (C$_6$H$_5$O)(Cl)PCH$_2$CH$_2$P(OC$_6$H$_5$)$_2$

A solution of PhOH (3.0 g, 31.9 mmol) in THF (30 mL) was treated with n-BuLi (1.6 M solution in THF, 16 mmol) at room temperature over a period of 5 min, and stirred for 2 h before 1.0 g of polymer-bound (Cl)PCH$_2$CH$_2$P(Cl)$_2$ (1.0 g, 0.94 mm/g, 0.94 mmol, prepared as in Example 5) was added. The resulting suspension was stirred at room temperature for 2 h before the excess PhOH and PhOLi were filtered off, and the resin was washed with THF (3×20 mL), hexane (3×20 mL). The resulting resin was dried in vacuo overnight. A suspension of the resin above (0.61 g, 0.82 mm/g, 0.50 mmol) and PCl$_3$ (0.62 g, 4.5 mmol) in THF (10 mL) was stirred overnight at room temperature before the resin was filtered off and washed with THF (2×5 mL) and hexane (2×10 mL). The combined filtrates were dried in vacuo to remove the solvent and excess PCl$_3$. The resulting residue was 133 mg (56%) of the title compound (C$_6$H$_5$O)(Cl)PCH$_2$CH$_2$P(OC$_6$H$_5$)$_2$. It was >95% pure by $^1$H NMR and GC/MS. $^{31}$P NMR (121 MHz, C$_6$D$_6$): δ 199.5 (d, J=16.8 Hz), 178.9 (d, J=16.8 Hz). $^1$H NMR (500 MHz, CDCl$_3$): δ 7.25–6.93 (m, 15H), 2.40 (m, 2H), 2.16 (m, 2H). $^{13}$C NMR (125 MHz, CDCl$_3$): δ 155.4, 155.0, 129.9, 129.8, 124.7, 123.8, 119.9, 119.4, 31.1, 27.7. HRMS: Calcd. for C$_{14}$H$_{14}$O$_2$P$_2$Cl ((M$^+$−OPh): 311.0158. Found: 311.0117.

Example 113

Synthesis of 1-(di-3,5-Difluorophenylphosphino)-2-(3,5-difluorophenyl-phenylphosphinite)ethane A solution of 700 mg (1.5 mmol) of (C$_6$H$_3$F$_2$)(Cl)PCH$_2$CH$_2$P(C$_6$H$_3$F$_2$)$_2$ in 20 mL of THF was treated with PhMgCl (3 M solution in THF, 1.7 mmol, prepared as in Example 5) at room temperature over a period of 5 min, and stirred for 1 h before the reaction was quenched with MeOH (2 mL). The resulting mixture was dissolved in a mixture of H$_2$O (2 mL)/THF (10 ml), and extracted with hexane (3×20 mL). After separation, the hexane extracts were dried over MgSO$_4$, filtered, and the hexane and THF removed from the filtrate by vacuum, to afford 450 mg (59%) of (C$_6$H$_3$F$_2$)(Ph)PCH$_2$CH$_2$P(C$_6$H$_3$F$_2$)$_2$. It was >95% pure by $^1$H NMR and GC/MS. $^{31}$P NMR (202 MHz, C$_6$D$_6$): δ −8.4 (d, J=38.8 Hz), −10.3 (d, J=38.9 Hz). $^1$H NMR (500 MHz, C$_6$D$_6$): δ 7.00–61.3 (m, 14H), 1.66–1.57 (m, 3H), 1.16 (m, 1H). $^{13}$C NMR (125 MHz, C$_6$D$_6$): δ 164.6, 162.6, 136.5, 133.8, 129.4, 128.9, 128.6, 128.4, 115.6, 114.9, 105.4, 104.7. 24.2, 23.9. HRMS: Calcd. for C$_{26}$H$_{18}$F$_6$P$_2$: 506.0788. Found: 506.0794.

Examples 114–116

Synthesis of Diphosphine Ligand Array Library

A solution of 700 mg (1.5 mmol) of (C$_6$H$_3$F$_2$)(Cl)PCH$_2$CH$_2$P(C$_6$H$_3$F$_2$)$_2$ in mixture of 15 mL of THF and 5 mL of THF-d$_8$ was divided into 34 NMR tubes (0.6 mL/tube) in the dry-box. Each NMR tube above was treated with only one R$_g$MgX (1–1.2 eq) at room temperature before the NMR tube was sealed. It was >95% pure by $^{31}$P NMR and GC/MS. This was repeated using 1-(di-(2-thienylphosphino))-2-chloro-2-thienylphosphinoethane and 1-(di-(o-tolyl phosphino))-2-chloro-o-tolylphosphinoethane. The scheme and results where x=Cl are shown in Tables 6A–8A.

TABLE 6A

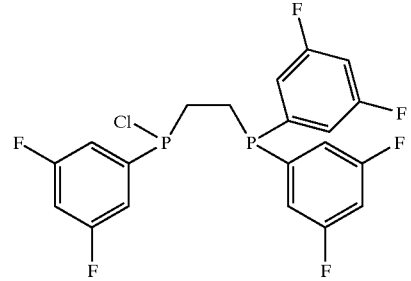

| Ex. | R$_g$ | $^{31}$P NMR ppm | Jp-p | MW (calc.) | MW (found) |
|---|---|---|---|---|---|
| 114-A | H | −6.8 | −61.9 | 26.5 | 430 | — |
| 114-B | phenyl | −7.9 | −9.8 | 38.7 | 506 | 507.6 |
| 114-C | o-tolyl | −7.6 | −20.5 | 39.9 | 520 | 521.7 |
| 114-D | m-tolyl | −7.5 | −9.6 | 38.8 | 520 | 521.7 |
| 114-E | p-tolyl | −7.7 | −10.6 | 38.3 | 520 | 521.7 |
| 114-F | 4-(t-butyl)-phenyl | −7.6 | −11.1 | 38.4 | 562 | 563.8 |
| 114-G | mesityl | −7.8 | −19.0 | 45.2 | 548 | 549.8 |
| 114-H | 2,5-dimethyl-phenyl | −7.7 | −17.7 | 44.9 | 534 | 535.7 |
| 114-I | 3-methyl-4-fluorophenyl | −7.7 | −10.7 | 40.0 | 538 | 539.7 |
| 114-J | 3,4,5-tri-fluorophenyl | −7.6 | −7.9 | 39.9 | 560 | 561.7 |
| 114-K | methyl | −7.8 | −26.3 | 29.9 | 444 | 445.5 |
| 114-L | ethyl | −7.9 | −11.8 | 31.5 | 458 | 459.5 |
| 114-M | n-propyl | −8.0 | −16.8 | 31.5 | 472 | 473.7 |
| 114-N | cyclopentyl | −4.1 | −7.8 | 30.8 | 498 | 499.6 |
| 114-O | n-heptyl | −7.9 | −16.1 | 31.4 | 500 | 501.6 |
| 114-P | cyclohexyl | −3.7 | −7.8 | 34.2 | 512 | 5137 |
| 114-Q | phenylmethyl | −7.5 | −11.2 | 33.4 | 520 | 521.6 |
| 114-R | 2-butyl | −2.6 (−2.9) | −7.7 (−7.8) | 34.2 (34.6) | 486 | 487.6 |
| 114-S | t-butyl | −11.2 | −7.7 | 38.6 | 486 | 487.6 |
| 114-T | n-pentadecyl | −7.8 | −16.1 | 31.3 | 640 | 642.1 |
| 114-U | 3,5-di-fluorophenyl | −8.1 | — | — | 542 | 543.8 |
| 114-V | i-propyl | −7.6 | 0.9 | 33.4 | 472 | 473.6 |
| 114-W | 3-chloro-4-fluorophenyl | −8.9 | −11.3 | 40.4 | 558.5 | 559.7 |
| 114-X | phenethyl | −7.6 | −15.2 | 31.7 | 534 | 535.7 |

TABLE 6A-continued

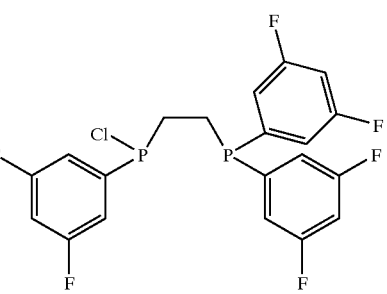

| Ex. | R_g | 31P NMR ppm | Jp-p | MW (calc.) | MW (found) |
|---|---|---|---|---|---|
| 114-Y | i-butyl | −7.7 | −19.9 | 31.6 | 486 | 487.6 |
| 114-Z | 2-methyl-2-phenylpropyl | −7.7 | −23.7 | 32.8 | 562 | 563.8 |
| 114-AA | n-decyl | −7.8 | −16.0 | 31.2 | 570 | 571.9 |
| 114-BB | 3,4-dimethoxyphenyl | −7.5 | −9.0 | 38.4 | 566 | 567.8 |
| 114-CC | 2-methoxy-4-fluorophenyl | −7.5 | −16.3 | 39.6 | 554 | 555.7 |
| 114-DD | 2-methoxy | −7.7 | −11.0 | 38.6 | 598 | 599.9 |
| 114-EE | 4-phenoxyphenyl | −7.3 | −15.6 | 38.8 | 536 | 537.7 |
| 114-FF | allyl | −7.5 | −17.2 | 33.4 | 470 | 471.5 |
| 114-GG | thiophenyl | −7.8 | 34.6 | 34.4 | 538 | 539.6 |
| 114-HH | phenoxy | −7.5 | 118.9 | 28.8 | 522 | 523.6 |

TABLE 7A

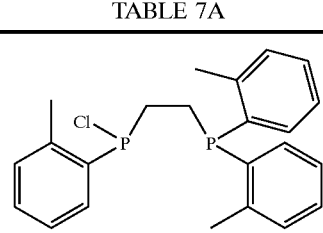

| Ex. | R_g | 31P NMR ppm | Jp-p | MW (calc.) | MW (found) |
|---|---|---|---|---|---|
| 115-A | H | −52.2 | −34.5 | 18.5 | 364 | 365.4 |
| 115-B | phenyl | −22.4 | −33 | 34.8 | 440 | 441.6 |
| 115-C | o-tolyl | −33.2 | — | — | 454 | 455.6 |
| 115-D | m-tolyl | −22.5 | −32.9 | 34.8 | 454 | 455.6 |
| 115-E | p-tolyl | −23.4 | −33.1 | 34.5 | 454 | 455.6 |
| 115-F | 4-(t-butyl)-phenyl | −24.1 | −32.8 | 34.4 | 496 | 497.8 |
| 115-G | mesityl | −29.5 | −32.6 | 44.2 | 482 | 483.7 |
| 115-H | 2,5-dimethylphenyl | −28.2 | −32.7 | 36.4 | 468 | 469.7 |
| 115-I | 3-methyl-4-fluorophenyl | −23.7 | −33.1 | 35.2 | 472 | 473.7 |
| 115-J | 3,4,5-trifluorophenyl | −20.2 | −33.4 | 37.4 | 494 | 495.7 |
| 115-K | methyl | −43.2 | −33.6 | 26.4 | 378 | 379.5 |
| 115-L | ethyl | −29.4 | −33.4 | 27.8 | 392 | 393.5 |
| 115-M | n-propyl | −34.7 | −33.4 | 28.1 | 406 | 407.6 |
| 115-N | cyclopentyl | −21.9 | −33.2 | 26.3 | 432 | 433.6 |
| 115-O | n-heptyl | −34.1 | −33.4 | 27.8 | 434 | 435.7 |
| 115-P | cyclohexyl | −23.2 | −33.1 | 30.8 | 446 | 447.7 |
| 115-Q | phenylmethyl | −26.9 | −33.3 | 30.3 | 454 | 487.7 (MO$_2^+$) |
| 115-R | 2-butyl | −22.2 (−21.7) | −33.0 (−32.9) | 30.7 (30.5) | 420 | 421.6 |
| 115-S | t-butyl | 9.9 | −32.6 | 345 | 420 | 421.6 |
| 115-T | n-pentadecyl | −34.2 | −33.4 | 40.6 | 574 | 576.1 |
| 115-U | 3,5-phenyl | −20.1 | −33.2 | 37.0 | 476 | 477.6 |
| 115-V | i-propyl | −18.1 | −33.1 | 29.8 | 406 | 407.5 |

TABLE 7A-continued

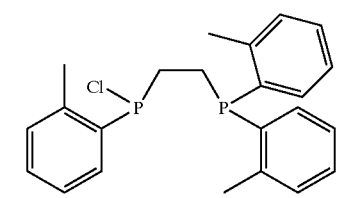

| Ex. | R_g | 31P NMR ppm | Jp-p | MW (calc.) | MW (found) |
|---|---|---|---|---|---|
| 115-W | 3-chloro-4-fluorophenyl | −22.7 | −33.1 | 35.2 | 493 | 493.7 |
| 115-X | phenethyl | −33.4 | −33.1 | 28.4 | 468 | 469.7 |
| 115-Y | i-butyl | −38.7 | −33.3 | 28.6 | 420 | 421.6 |
| 115-Z | 2-methyl-2-phenylpropyl | −43.4 | −33.2 | 30.8 | 496 | 497.8 |
| 115-AA | n-decyl | −34.1 | −33.4 | 27.8 | 504 | 505.8 |
| 115-BB | 3,4-dimethoxyphenyl | −22.2 | −32.9 | 34.4 | 500 | 501.8 |
| 115-CC | 2-methoxy-4-fluorophenyl | −31.5 | −33.2 | 35.4 | 488 | 489.7 |
| 115-DD | 4-phenoxyphenyl | −23.9 | −33.0 | 34.9 | 532 | 533.8 |
| 115-EE | 2-methoxy | −31.5 | −33.1 | 34.1 | 470 | 471.7 |
| 115-FF | allyl | −34.1 | −33.3 | 29.8 | 404 | 405.5 |
| 115-GG | thiophenyl | 21.2 | −33.4 | 35.5 | 472 | 473.6 |
| 115-HH | phenoxy | 114.6 | −33.5 | 27.0 | 456 | 457.6 |

TABLE 8A

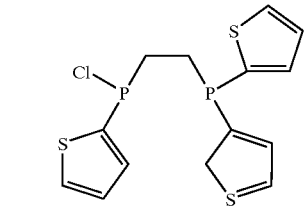

| Ex. | R_g | 31P NMR ppm | Jp-p | MW (calc.) | MW (found) |
|---|---|---|---|---|---|
| 116-A | H | −73.5 | −39.4 | 27.5 | 340 | 342 |
| 116-B | phenyl | −25.0 | −38.3 | 37.4 | 416 | 417.4 |
| 116-C | o-tolyl | −36.0 | −38.3 | 39.0 | 430 | 431.4 |
| 116-D | m-tolyl | −25.1 | −38.3 | 37.4 | 430 | 431.4 |
| 116-E | p-tolyl | −25.8 | −38.3 | 37.2 | 430 | 431.5 |
| 116-F | 4-(t-butyl)-phenyl | −26.3 | −38.3 | 37.4 | 472 | 473.5 |
| 116-G | mesityl | −26.1 | −38.2 | 43.8 | 459 | 459.5 |
| 116-H | 2,5-dimethylphenyl | −25.0 | −38.2 | 43.8 | 444 | 445.5 |
| 116-I | 3-methyl-4-fluorophenyl | −26.0 | 38.4 | 38.8 | 448 | 449.5 |
| 116-J | 3,4,5-trifluorophenyl | −23.2 | −38.6 | 39.2 | 470 | 471.5 |
| 116-K | methyl | −40.5 | −38.4 | 32.2 | 354 | 387.3 (MO$_2^+$) |
| 116-L | ethyl | −26.1 | −38.4 | 32.4 | 368 | 401.5 (MO$_2^+$) |
| 116-M | n-propyl | −31.2 | −38.4 | 32.6 | 382 | 415.4 (MO$_2^+$) |
| 116-N | cyclopentyl | −18.9 | −38.3 | 31.5 | 408 | 441.4 (MO$_2^+$) |
| 116-O | n-heptyl | −30.5 | −38.4 | 32.4 | 410 | 411.4 |
| 116-P | cyclohexyl | −18.8 | −38.3 | 33.0 | 422 | 423.4 |
| 116-Q | phenylmethyl | −24.7 | −38.2 | 33.4 | 430 | 463.5 (MO$_2^+$) |
| 116-R | 2-butyl | −17.7 (−17.6) | −38.3 (−38.2) | 33.2 (33.2) | 396 | 429.4 (MO$_2^+$) |
| 116-S | t-butyl | −2.2 | −38.1 | 37.2 | 396 | 429.4 (MO$_2^+$) |

TABLE 8A-continued

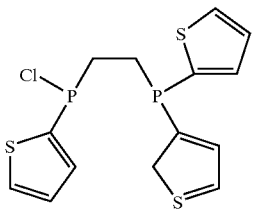

| Ex. | $R_g$ | 31P NMR ppm | Jp-p | MW (calc.) | MW (found) |
|---|---|---|---|---|---|
| 116-T | n-pentadecyl | −30.6 | −38.5 | 32.5 | 550 | 551.8 |
| 116-U | 3,5-difluorophenyl | −23.1 | −38.5 | 38.8 | 452 | 453.4 |
| 116-V | i-propyl | −14.1 | −38.3 | 32.8 | 382 | 383.3 |
| 116-W | 3-chloro-4-fluorophenyl | −25.4 | −38.5 | 38.9 | 469 | 469.4 |
| 116-X | phenethyl | −30.1 | −38.4 | 32.7 | 444 | 445.5 |
| 116-Y | i-butyl | −34.4 | −38.4 | 32.7 | 396 | 397.4 |
| 116-Z | 2-methyl-2-phenylpropyl | −38.8 | −38.5 | 33.7 | 472 | 505.7 ($MO_2^+$) |
| 116-AA | n-decyl | −30.5 | −38.4 | 32.4 | 480 | 481.6 |
| 116-BB | 3,4-dimethoxyphenyl | −24.6 | −38.2 | 37.4 | 476 | 477.5 |
| 116-CC | 2-methoxy-4-fluorophenyl | −31.1 | −38.3 | 38.0 | 464 | 465.5 |
| 116-DD | 4-phenoxyphenyl | −26.2 | −38.3 | 37.6 | 508 | 509.6 |
| 116-EE | 2-methoxy | −31.1 | −38.1 | 37.2 | 446 | 447.4 |
| 116-FF | allyl | −30.9 | −38.4 | 33.5 | 380 | 413.3 ($MO_2^+$) |
| 116-GG | thiophenyl | 20.1 | −38.6 | 37.3 | 448 | 482.4 ($MO_2^+$) |
| 116-HH | phenoxy | 110.3 | −38.1 | 36.4 | 432 | 431.0 |

Synthesis of Polymer-bound Diphosphine Monoxide Ligands

Example 117

Polymer-bound $(Me_2CH)P(O)CH_2CH_2P(CHMe_2)_2$

A solution of 160 mg (0.68 mmol) of $(Me_2CH)PH(O)CH_2CH_2P(CHMe_2)_2$ from Example 26 and 1.0 mg (0.015 mmol) of NaOEt in 10 mL of THF was stirred at room temperature over a period of 20 min before formypolystyrene (2% DVB, 0.90 g, 0.46 mmol/g, 0.41 mmol) was added to the reaction mixture. The resulting suspension was stirred overnight. After the solution was filtered off. resin was washed with THF (3×20 mL), hexane (3×20 mL). The resulting resin was dried in vacuo overnight to afford polymer-bound $(Me_2CH)PH(O)CH_2CH_2P(CHMe_2)_2$. $^{31}P$ NMR (122 MHz, $CDCl_3$): δ 53.3 (s), 10.5 (s) ppm. $^{13}C$ NMR (75 MHz, $CDCl_3$): δ 31.5, 25.5, 22.9 (d, $J_{p-c}$=55.6 Hz), 20.0, 18.9, 15.7, 14.1.

Example 118

Polymer-bound $(Ph)PCH_2CH_2PPh(O)(C_6H_2Me_3)$

A solution of 150 mg (0.614 mmol) of $PhPH(O)(2,4,6-C_6H_2Me_3)$ from Example 61 and 1.0 mg (0.01 mmol) of NaOtBu in 10 mL of THF was stirred at room temperature over a period of 10 min before polymer-bound $PhPCH=CH_2$ (2% DVB, 0.5 g, 0.938 mmol/g, 0.469 mmol, from Example 52-S) was added to the reaction solution. The resulting suspension was refluxed overnight. After the solution was filtered off, resin was washed with THF (3×20 mL), $Me_2CHOH$ (2×5 mL), hexane (3×20 mL). The resulting resin was dried in vacuo overnight to afford polymer-bound $(Ph)PCH_2CH_2PPh(O)(C_6H_2Me_3)$. $^{31}P$ NMR (122 MHz, $CDCl_3$): δ 62.4 (s), 37.8 (s) ppm.

Example 119

Synthesis of $PhPH(O)CH_2CH_2PPh(O)(C_6H_2Me_3)$

A suspension of polymer-bound $(Ph)PCH_2CH_2PPh(O)(C_6H_2Me_3)$ above (0.5 g, 0.469 mmol) and $H_2O$ (0.5g, 27.8 mmol) in 10 mL of THF was refluxed overnight. After the resin was filtered off and washed with THF (10 mL), the filtrates were dried in vacuo to remove the solvents and excess $H_2O$. The resulting residue was 50 mg (28% yield) of $PhPH(O)CH_2CH_2PPh(O)(C_6H_2Me_3)$. It was >95% pure by $^1H$ NMR and GC/MS. $^{31}P$ NMR (202 MHz, $CDCl_3$, $^1H$-decoupled): δ 39.2 (d, J=52.5 Hz), 28.2 (d, J=52.3 Hz); 39.0 (d, J=50.9 Hz), 28.0 (d, J=50.7 Hz). $^{31}P$ NMR (121 MHz, $CDCl_3$, $^1H$-coupled): δ 39.3 (d, $J_{P-P}$=48.5 Hz), 28.1 (d, $J_{P-H}$=474.7 Hz); 39.0 (d, $J_{P-P}$=48.8 Hz), 28.0 (d, $J_{P-H}$=474.7 Hz). $^1H$ NMR (500 MHz, $CDCl_3$): δ 7.51 (d, $J_{P-H}$=472.9 Hz), 7.48 (d, $J_{P-H}$=473.6 Hz), 7.65–7.30 (m, 10H), 6.82 (d, J=3.31 Hz, 1H), 6.78 (d, J=3.29 Hz, 1H), 2.55 (m, 4H), 2.33 (s), 2.28 (s), 2.22(s), 2.20 (s). $^{13}C$ NMR (125 MHz, $CDCl_3$): δ 143.3, 142.2, 135.5, 132.9, 131.7, 131.5, 130.1, 130.0, 129.2, 129.0, 124.0, 123.0, 23.6, 21.1.

Synthesis of C1 and C2-Diphosphorus-related Ligands

Example 120

Synthesis of Polymer-bound 1-(2,3,4,5-Tetraethylphospholyl)-2-chlorophosphinoethane Chloromethylpolystyrene-divinylbenzene (50 g, 44.5 mmol, 2% DVB) was added to a solution of t-butylamine (69.6 g, 950 mmol) in THF (700 mL), and the reaction mixture was refluxed overnight before the resin was filtered, washed with $H_2O$ (500 mL), THF (500 mL), hexane (500 mL), $H_2O$ (500 mL), and $Et_2O$ (500 mL). The resulting resin was dried in vacuo, and then added to THF (700 mL). The mixture was cooled to 0° C. and treated dropwise with n-butyllithium (64 mmol, 1.6 M solution in pentane) over a period of 2 h before warmed to room temperature and stirred overnight. After filtration, the resin was washed with hexane (400 mL), THF (400 mL), $Et_2O$ (400 mL). The resin was slowly added to a solution of $Cl_2PCH_2CH_2PCl_2$ (37.0 g, 159.6 mmol) in THF (800 mL) at room temperature, and the resulting mixture was stirred overnight before filtration and washing with THF (2×400 mL), hexane (2×400 mL), $CH_2Cl_2$ (2×400 mL), hexane (2×400 mL). The resin was added to $CH_2Cl_2$ (500 mL), and then at room temperature treated with a mixture of $CH_2Cl_2$ (50 mL) and $Cp_2ZrC_4Et_4$ (17.2 g, 45 mmol) generated from the reaction of $Cp_2ZrCl_2$, n-butyllithium , and EtC≡CEt. After the mixture was stirred for 4 h, the solvents were filtered off and the resulting resin was washed with CH2Cl2 (3×500 mL), THF (3×500 mL), and hexane (3×500 mL), dried in vacuo to give 50 g (96% yield with respect to the starting Merrifield resin, which was determined using N, P, and Cl elemental analysis) of the title polymer-bound compound. $^{31}P$ NMR (122 MHz, $C_6D_6$): d 154.2, 1.3.

I claim:
1. A process to prepare a combinatorial library of supported phosphine compounds selected from the group consisting of Formulae 1A, 2A, 3A, 4A, 5A, 6A, and 7A

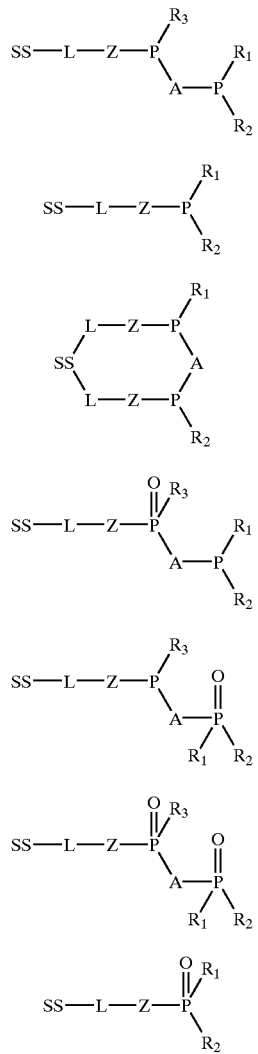

wherein:
- Z is a divalent attaching group covalently attached to at least one P in the phosphine, selected from the group consisting of an optionally-substituted carbon chain of 1–10 carbon atoms, —O—, —S—, and —NR4—, where $R_4$ is selected from the group consisting of an optionally-substituted hydrocarbyl and halogen;
- L is a divalent linking group covalently attached to Z and to SS, selected from the group consisting of optionally-substituted chains of from 1 to 12 linear, branched, and cyclic carbon atoms;
- SS is a solid support;
- A is a divalent group of 1–12 aliphatic or aromatic carbon atoms, linear or branched;
- $R_1$, $R_2$, and $R_3$ are independently selected from the group consisting of hydrogen, hydrocarbyl, substituted hydrocarbyl, heterocycle, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle, and $R_2$ and $R_3$ together, $R_1$ and $R_3$ together, or $R_1$ and $R_2$ together can optionally form a ring, the process comprising the steps of:
a) contacting (i) one or more phosphines selected from the group consisting of $XPR_1R_2$, $XR_3P$—A—$PR_1R_2$, $HP(=O)R_1R_2$, $HP(=O)R_3$—A—$PR_1R_2$, and $HP(=O)R_3$—A—$P(=O)R_1R_2$ wherein X is a halogen, with (ii) one or more solid supports, resulting in at least one P in each phosphine attached indirectly or directly to the solid support via one or more covalent bonds, and
b) optionally replacing one or more substituent of the group $R_1$, $R_2$, or $R_3$ with any other substituent of the group $R_1$, $R_2$, or $R_3$.

2. The process of claim 1 wherein SS is selected from the group consisting of polyolefins, polyacrylates, polymethacrylates, and copolymers thereof.

3. The process of claim 1 wherein the supported phosphine compounds are of Formula 1A, and the process comprises the steps of:
a) contacting at least 2 molar equivalents of one or more phosphines of the Formula $XR_3P$—A—$PR_1R_2$ wherein X is a halogen, with no more than one molar equivalent of one or more of Z, resulting in one P in each phosphine being covalently bonded to the Z; and
b) optionally replacing one or more substituent of the group $R_1$, $R_2$, and $R_3$ with any one or more of the substituent of the group of $R_1$, $R_2$, and $R_3$.

4. The process of claim 3 wherein SS is polystyrene;
L is —$CH_2$—;
A is selected from the group consisting of an optionally-substituted carbon chain of 1–3 carbon atoms and an optionally-substituted carbon ring of 6–12 carbon atoms;
Z is selected from the group consisting of an optionally-substituted carbon chain of 1–10 carbon atoms, —($NR_4$)—, and —O—;
$R_4$ is selected from the group consisting of chloro, cyclohexyl, n-propyl, i-propyl, n-butyl, phenyl, and t-butyl;
$R_1$, $R_2$, and $R_3$ are independently selected from the group consisting of hydrogen, Cl, alkyl, alkenyl, aryl, $SQ_1$, $OQ_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle, and where $R_1$ and $R_2$ together with the P form a phosphole, aryl, or alkyl ring.

5. The process of claim 1 wherein the supported phosphine compounds are of Formula 2A, and the process comprises the steps of:
a) contacting one or more phosphines of the Formula $PR_1R_2X$ wherein X is a halogen, with one or more solid supports, resulting in one P in each phosphine being covalently bonded to Z; and
b) optionally replacing one or both of $R_1$ and $R_2$ with any other $R_1$ or $R_2$.

6. The process of claim 1 wherein the supported phosphine compounds are of Formula 3A, and the process comprises the steps of:
a) contacting no more than one molar equivalent of one or more phosphines of the Formula $XR_3P$—A—$PR_1R_2$ wherein X is a halogen, with at least two molar equivalents of one or more of Z, resulting in both of the P in each phosphine being covalently bonded to the Z; and b) optionally replacing one or more substituent of the group $R_1$ and $R_2$ with any one or more of the substituent of the group $R_1$ and $R_2$.

7. The process of claim 1 wherein the supported phosphine compounds are of Formula 4A, and the process comprises the steps of:

a) contacting one or more phosphines of the Formula HP(=O) $R_3$—A—$PR_1R_2$ with one or more solid supports, resulting in one P in each phosphine being covalently bonded to Z; and b) optionally replacing one or more substituent of the group $R_1$, $R_2$, and $R_3$ with any one or more of the substituent of the group $R_1$, $R_2$, and $R_3$.

8. The process of claim 7 wherein SS is polystyrene;

L is —$CH_2$—;

Z is selected from the group consisting of optionally-substituted carbon chain of 1–10 carbon atoms, —($NR_4$)—, and —O—;

$R_4$ is selected from the group consisting of chloro, cyclohexyl, n-propyl, i-propyl, n-butyl, phenyl, and t-butyl; and $R_1$, $R_2$, and $R_3$ are independently selected from the group consisting of hydrogen, Cl, alkyl, alkenyl, aryl, $SQ_1$, $OQ_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle, and where $R_1$ and $R_2$ together with the P form a phosphole, aryl, or alkyl ring.

9. The process of claim 1 wherein the supported phosphine compounds are of Formula 5A, and the process comprises the steps of:

a) contacting one or more phosphines of the Formula HP(=O)$R_1R_2$ with one or more solid supports of the formula

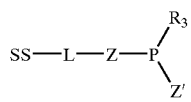

wherein the P in the solid support is covalently bonded to Z and Z' is selected from the group consisting of alkenyls, resulting in the phosphorus in each phosphine being covalently bonded to the phosphorus in the solid support via Z', and b) optionally replacing one or more of $R_1$, $R_2$, and $R_3$ with any one or more of $R_1$, $R_2$, and $R_3$.

10. The process of claim 1 wherein SS is polystyrene;

L is —$CH_2$—;

Z is selected from the group consisting of optionally-substituted carbon chain of 1–10 carbon atoms, —($NR_4$)—, and —O—;

A is selected from the group consisting of an optionally-substituted carbon chain of 1–3 carbon atoms and an optionally-substituted carbon ring of 6–12 carbon atoms;

$R_4$ is selected from the group consisting of chloro, cyclohexyl, n-propyl, i-propyl, n-butyl, phenyl, and t-butyl; and $R_1$, $R_2$, and $R_3$ are independently selected from the group consisting of hydrogen, Cl, alkyl, alkenyl, aryl, $SQ_1$, $OQ_2$, and $PQ_3Q_4$, where $Q_1$, $Q_2$, $Q_3$, and $Q_4$ are selected from the group consisting of hydrogen, hydrocarbyl, substituted hydrocarbyl, hydrocarbylamino, and heterocycle; and where $R_1$ and $R_2$ together with the P form a phosphole, aryl, or alkyl ring.

11. A combinatorial library of supported phosphine compounds selected from the group consisting of Formulae 1A, 2A, 3A, 4A, 5A, 6A, and 7A

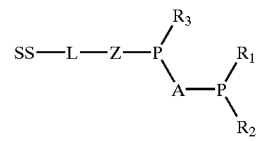

1A

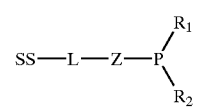

2A

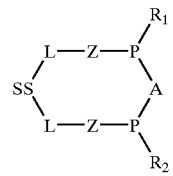

3A

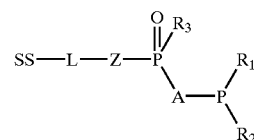

4A

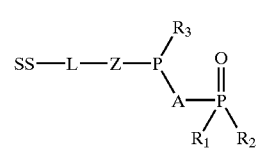

5A

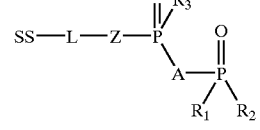

6A

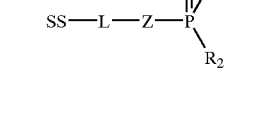

7A wherein:

SS is a solid support wherein at least one P in each phosphine is attached indirectly or directly to the solid support via one or more covalent bonds;

A is a divalent group of 1–12 aliphatic or aromatic carbon atoms, linear or branched;

$R_1$, $R_2$, and $R_3$ are independently selected from the group consisting of hydrogen, hydrocarbyl, substituted hydrocarbyl, heterocycle, organometallic, Cl, Br, I, $SQ_1$, $OQ_2$, $PQ_3Q_4$, and $NQ_5Q_6$, where $Q_1$, $Q_2$, $Q_3$, $Q_4$, $Q_5$, and $Q_6$ are independently selected from the group consisting of hydrogen, hydrocarbyl, substituted hydrocarbyl, hydrocarbylamino, alkoxy, aryloxy, and heterocycle, and $R_2$ and $R_3$ together, $R_1$ and $R_3$ together, or $R_1$ and $R_2$ together can optionally form a ring;

Z is a divalent attaching group covalently attached to at least one P in the phosphine, selected from the group consisting of an optionally-substituted carbon chain of 1–10 carbon atoms, —O—, —S—, and —NR$_4$—, where R$_4$ is selected from the group consisting of an optionally-substituted hydrocarbyl and halogen; and L is a divalent linking group covalently attached to Z and to SS, selected from the group consisting of optionally substituted chains of from 1 to 12 linear, branched, and cyclic carbon atoms.

12. The combinatorial library of claim 11 wherein SS is selected from the group consisting of polyolefins, polyacrylates, polymethacrylates, and copolymers thereof.

13. The combinatorial library of claim 11 that is Formula 1A.

14. The combinatorial library of claim 13 wherein SS is polystyrene;

L is —CH$_2$—;

A is selected from the group consisting of an optionally-substituted carbon chain of 1–3 carbon atoms and an optionally-substituted carbon ring of 6–12 carbon atoms;

Z is selected from the group consisting of an optionally-substituted carbon chain of 1–10 carbon atoms, —(NR$_4$)—, and —O—;

R$_4$ is selected from the group consisting of chloro, cyclohexyl, n-propyl, i-propyl, n-butyl, phenyl, and t-butyl;

R$_1$, R$_2$, and R$_3$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$, and Q$_4$ are selected from the group consisting of hydrogen, hydrocarbyl, substituted hydrocarbyl, hydrocarbylamino, and heterocycle, and where R$_1$ and R$_2$ together with the P form a phosphole, aryl, or alkyl ring.

15. The combinatorial library of claim 11 that is Formula 2A.

16. The combinatorial library of claim 15 wherein SS is polystyrene;

L is —CH$_2$—;

Z is selected from the group consisting of optionally-substituted carbon chain of 1–10 carbon atoms, —(NR$_4$)—, and —O—;

R$_4$ is selected from the group consisting of chloro, cyclohexyl, n-propyl, i-propyl, n-butyl, phenyl, and t-butyl; and R$_1$ and R$_2$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$, and Q$_4$ are selected from the group consisting of hydrogen, hydrocarbyl, substituted hydrocarbyl, hydrocarbylamino, and heterocycle, and where R$_1$ and R$_2$ together with the P form a phosphole, aromatic, or alkyl ring.

17. The combinatorial library of claim 11 that is Formula 3A.

18. The combinatorial library of claim 17 wherein SS is polystyrene;

L is —CH$_2$—;

A is selected from the group consisting of an optionally-substituted carbon chain of 1–3 carbon atoms and an optionally-substituted carbon ring of 6–12 carbon atoms;

Z is selected from the group consisting of an optionally-substituted carbon chain of 1–10 carbon atoms, —(NR$_4$)—, and —O—;

R$_4$ is selected from the group consisting of chloro, cyclohexyl, n-propyl, i-propyl, n-butyl, phenyl, and t-butyl;

R$_1$ and R$_2$ are independently selected from the group consisting of hydrogen, Cl, alkyl, alkenyl, aryl, SQ$_1$, OQ$_2$, and PQ$_3$Q$_4$, where Q$_1$, Q$_2$, Q$_{30}$, and Q$_4$ are selected from the group consisting of hydrogen, hydrocarbyl, substituted hydrocarbyl, hydrocarbylamino, and heterocycle, and where R$_1$ and R$_2$ together with the P form a phosphole, aryl, or alkyl ring.

19. The combinatorial library of claim 11 that is Formula 4A.

20. The combinatorial library of claim 19 wherein SS is polystyrene;

L is —CH$_2$—;

Z is selected from the group consisting of optionally-substituted carbon chain of 1–10 carbon atoms, —(NR$_4$)—, and —O—;

R$_4$ is selected from the group consisting of chloro, cyclohexyl, n-propyl, i-propyl, n-butyl, phenyl, and t-butyl; and R$_1$, R$_2$, and R$_3$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$, and Q$_4$ are selected from the group consisting of hydrogen, hydrocarbyl, substituted hydrocarbyl, hydrocarbylamino, and heterocycle, and where R$_1$ and R$_2$ together with the P form a phosphole, aryl, or alkyl ring.

21. The combinatorial library of claim 11 that is Formula 5A.

22. The combinatorial library of claim 21 wherein SS is polystyrene;

L is —CH$_2$—;

Z is selected from the group consisting of optionally-substituted carbon chain of 1–10 carbon atoms, —(NR$_4$)—, and —O—;

A is selected from the group consisting of an optionally-substituted carbon chain of 1–3 carbon atoms and an optionally-substituted carbon ring of 6–12 carbon atoms;

R$_4$ is selected from the group consisting of chloro, cyclohexyl, n-propyl, i-propyl, n-butyl, phenyl, and t-butyl; and R$_1$, R$_2$, and R$_3$ are independently selected from the group consisting of hydrogen, Cl, alkyl, alkenyl, aryl, SQ$_1$, OQ$_2$, and PQ$_3$Q$_4$, where Q$_1$, Q$_2$, Q$_3$, and Q$_4$ are selected from the group consisting of hydrogen, hydrocarbyl, substituted hydrocarbyl, hydrocarbylamino, and heterocycle; and where R$_1$ and R$_2$ together with the P form a phosphole, aryl, or alkyl ring.

* * * * *